(12) United States Patent
Xu et al.

(10) Patent No.: US 8,980,829 B2
(45) Date of Patent: Mar. 17, 2015

(54) ARYL GLYCOSIDE COMPOUND, PREPARATION METHOD AND USE THEREOF

(75) Inventors: Zusheng Xu, Shanghai (CN); Su Qian, Shanghai (CN)

(73) Assignees: Shanghai Yingli Science and Technology Co., Ltd, Shanghai (CN); Shanghai Chempartner Co., Ltd, Shanghai (CN)

( * ) Notice: Subject to any disclaimer, the term of this patent is extended or adjusted under 35 U.S.C. 154(b) by 0 days.

(21) Appl. No.: 14/000,312

(22) PCT Filed: Feb. 17, 2012

(86) PCT No.: PCT/CN2012/071243
§ 371 (c)(1),
(2), (4) Date: Aug. 19, 2013

(87) PCT Pub. No.: WO2012/109996
PCT Pub. Date: Aug. 23, 2012

(65) Prior Publication Data
US 2013/0324464 A1    Dec. 5, 2013

(30) Foreign Application Priority Data
Feb. 18, 2011    (CN) .......................... 2011 1 0040757

(51) Int. Cl.
| | |
|---|---|
| *A61K 38/28* | (2006.01) |
| *A61P 5/50* | (2006.01) |
| *C07H 15/26* | (2006.01) |
| *C07D 405/14* | (2006.01) |
| *C07D 309/10* | (2006.01) |
| *C07D 405/12* | (2006.01) |
| *C07D 407/12* | (2006.01) |
| *C07D 409/12* | (2006.01) |
| *A61K 31/7034* | (2006.01) |
| *A61K 31/7048* | (2006.01) |
| *A61K 31/7042* | (2006.01) |
| *A61K 31/7052* | (2006.01) |
| *A61K 45/06* | (2006.01) |
| *C07H 1/00* | (2006.01) |
| *C07F 5/02* | (2006.01) |

(52) U.S. Cl.
CPC .............. *C07H 15/26* (2013.01); *C07D 405/14* (2013.01); *C07D 309/10* (2013.01); *C07D 405/12* (2013.01); *C07D 407/12* (2013.01); *C07D 409/12* (2013.01); *A61K 31/7034* (2013.01); *A61K 31/7048* (2013.01); *A61K 31/7042* (2013.01); *A61K 31/7052* (2013.01); *A61K 45/06* (2013.01); *C07H 1/00* (2013.01); *C07F 5/025* (2013.01)
USPC .......................................................... 514/6.5

(58) Field of Classification Search
None
See application file for complete search history.

(56) References Cited

U.S. PATENT DOCUMENTS

| 7,579,449 B2 * | 8/2009 | Eckhardt et al. ............. 536/1.11 |
| 7,943,748 B2 | 5/2011 | Matsuoka et al. |
| 2003/0114390 A1 | 6/2003 | Washburn et al. |
| 2005/0209166 A1 | 9/2005 | Eckhardt et al. |

(Continued)

FOREIGN PATENT DOCUMENTS

| CA | 2 557 801 A1 | 10/2005 |
| CN | 1930141 A | 3/2007 |

(Continued)

OTHER PUBLICATIONS

Zhu et al; "Organocatalytic Michael Addition of Aldehydes to Protected 2-Amino-1-Nitroethenes: The Practical Syntheses of Oseltamivir (Tamiflu) and Substituted 3-Aminopyrrolidines;" Angew. Chem. Int. Ed.; 2010; vol. 49; pp. 4656-4660.

(Continued)

*Primary Examiner* — Marcela M Cordero Garcia
*Assistant Examiner* — Kaipeen Yang
(74) *Attorney, Agent, or Firm* — Oliff PLC

(57) ABSTRACT

Disclosed are an aryl glycoside compound as represented by formula I or formula I', a pharmaceutically acceptable salt thereof, optical isomer thereof or a prodrug thereof. The present invention relates to a method of preparing said aryl glycoside compound and the use thereof. The aryl glycoside compound of the present invention has an excellent ability on inhibit SGLT activity, especially SGLT2 activity, and is diabetes-fighting medicine with great potential.

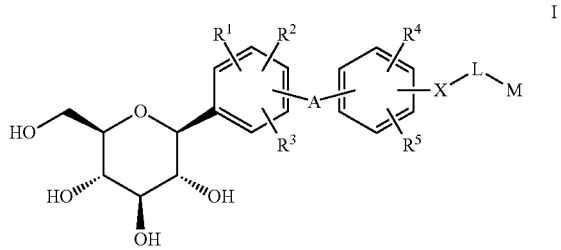

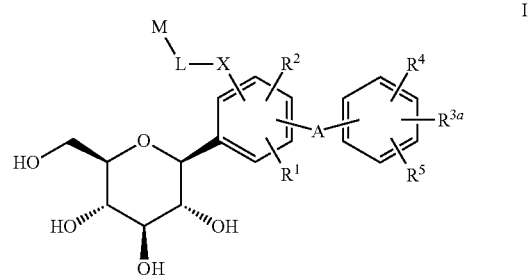

21 Claims, No Drawings

(56) References Cited

U.S. PATENT DOCUMENTS

| | | | |
|---|---|---|---|
| 2006/0122126 A1 | 6/2006 | Imamura et al. | |
| 2007/0293690 A1 | 12/2007 | Tomiyama et al. | |
| 2008/0009639 A1 | 1/2008 | Radatus et al. | |

FOREIGN PATENT DOCUMENTS

| | | |
|---|---|---|
| CN | 101503399 A | 8/2009 |
| CN | 101652377 A | 2/2010 |
| CN | 101735140 A | 6/2010 |
| CN | 101790311 A | 7/2010 |
| CN | 101812043 A | 8/2010 |
| CN | 102127003 A | 7/2011 |
| CN | 102643256 A | 8/2012 |
| EP | 2 676 965 A1 | 12/2013 |
| KR | 1020120006311 A | 1/2012 |
| WO | WO 01/27128 A1 | 4/2001 |
| WO | WO 02/083066 A2 | 10/2002 |
| WO | WO 03/099836 A1 | 12/2003 |
| WO | WO 2004/063209 A2 | 7/2004 |
| WO | WO 2005/012326 A1 | 2/2005 |
| WO | WO 2006/011502 A1 | 2/2006 |
| WO | WO 2008/034859 A1 | 3/2008 |
| WO | WO 2008/122014 A1 | 10/2008 |
| WO | WO 2009/026537 A1 | 2/2009 |
| WO | WO 2009/078813 A1 | 6/2009 |
| WO | WO 2012/025857 A1 | 3/2012 |

OTHER PUBLICATIONS

Kim et al; "Influenza Neuraminidase Inhibitors Possessing a Novel Hydrophobic Interaction in the Enzyme Active Site: Design, Synthesis, and Structural Analysis of Carbocyclic Sialic Acid Analogues with Potent Anti-Influenza Activity;" J. Am. Chem. Soc.; 1997; col. 119; pp. 681-690.

Yeung et al; "A Short Enantioselective Pathway for the Synthesis of the Anti-Influenza Neuramidase Inhibitor Oseltamivir from 1,3-Butadiene and Acrylic Acid;" J. Am. Chem. Soc.; 2006; vol. 128; pp. 6310-6311.

Trost et al; "A Concise Synthesis of (−)-Oseltamivir;" Angew. Chem. Int. Ed.; 2008; col. 47; pp. 3759-3761.

Ishikawa et al; "High-Yielding Synthesis of the Anti-Influenza Neuramidase Inhibitor (−)-Oseltamivir by Three "One Pot" Operations;" Angew. Chem. Int. Ed.; 2009; vol. 48; pp. 1304-1307.

Dalko et al; "Enantioselective Organocatalysis;" Angew. Chem. Int. Ed.; 2001; vol. 40; pp. 3726-3748.

Vicario et al; "Organocatalytic Enantioselective Michael and Hetero-Michael Reactions;" Synthesis; 2007; No. 14; pp. 2065-2092.

Enders et al; "Control of four stereocentres in a triple cascade organocatalytic reaction;" Nature; Jun. 15, 2006; vol. 441; pp. 861-863.

Moualla et al; "Voreloxin;" Drugs of the Future; 2009; vol. 34; No. 5; pp. 363-374.

Mar. 24, 2011 Search Report issued in International Patent Application No. PCT/CN2010/079936 (with translation).

Mar. 24, 2011 Written Opinion issued in International Patent Application No. PCT/CN2010/079936 (with translation).

Mar. 30, 2012 Office Action issued in Chinese Patent Application No. 201010613246.8 (with translation).

Oct. 24, 2012 Office Action issued in Chinese Patent Application No. 201010613246.8 (with translation).

Jul. 1, 2014 Extended Search Report issued in European Patent Application No. 12746875.9.

Apr. 17, 2014 Chinese Office Action issued in Chinese Patent Application No. 20120044049.8 (with translation).

Edward C. Chao et al., "SGLT2 inhibition—a novel strategy for diabetes treatment," Nature Reviews, Drug Discovery, vol. 9, pp. 551-559, Jul. 2010.

Indian Patent Application No. IN8004/DELNP/2013, filed Sep. 11, 2013.

Handlon; "Sodium glucose co-transporter 2 (SGLT2) inhibitors as potential antidiabetic agents;" Expert Opin. Ther. Patents; 2005; vol. 15; No. 11; pp. 1531-1540.

Washburn; "Development of the Renal Glucose Reabsorption Inhibitors: A New Mechanism for the Pharmacotherapy of Diabetes Mellitus Type 2;" Journal of Medicinal Chemistry; 2009; vol. 52; No. 7; pp. 1785-1794.

Chao et al; "SGLT2 inhibition—a novel strategy for diabetes treatment;" Nature Reviews; Jul. 2010; vol. 9; pp. 551-559.

Loy et al; "Enantioselective Intramolecular Openings of Oxetanes Catalyzed by (salen)Co(III) Complexes: Access to Enantioenriched Tetrahydrofurans;" J. Am. Chem. Soc.; 2009; vol. 131; pp. 2786-2787.

Burkhard et al; "Synthesis of Azaspirocycles and their Evaluation in Drug Discovery;" Angew. Chem. Int. Ed.; 2010; vol. 49; pp. 3524-3527.

Kim et al; "Novel macrocyclic C-aryl glucoside SGLT2 inhibitors as potential antidiabetic agents;" Bioorganic & Medicinal Chemistry; 2011; vol. 19; pp. 5468-5479.

Kuzuhara et al; "Syntheses with Partially Benzylated Sugars. VIII. Substitution at C-5 in an Aldose. The Synthesis of 5-$O$-Methyl-D-glucofuranose Derivatives;" J. Org. Chem. 1967; vol. 32; No. 8; pp. 2531-2534.

Asano et al; "$N$-Containing sugars from *Morus alba* and their glycosidase inhibitory activities;" Carbohydrate Research; 1994; vol. 259; pp. 243-255.

Adamczyk et al; "Synthesis of Biological Markers in Fossil Fuels, 2. Synthesis and C NMR Studies of Substituted Indans and Tetralins;" J. Org. Chem; 1984; vol. 49; No. 22; pp. 4226-4237.

Kawasaki et al.; "The effect of vinyl esters on the enantioselectivity of the lipase-catalysed transesterification of alcohols;" Tetrahedron: *Asymmetry*; 2001; vol. 12; pp. 585-596.

Zhang et al; "F-18 Stilbenes as PET Imaging Agents for Detecting β-Amyloid Plaques in the Brain;" J. Med. Chem. 2005; vol. 48; pp. 5980-5988.

Meng et al; "Discovery of Dapagliflozin: A Potent, Selective Renal Sodium-Dependent Glucose Cotransporter 2 (SGLT2) Inhibitor for the Treatment of Type 2 Diabetes;" J. Med. Chem.; 2008; vol. 51; pp. 1145-1149.

Barnett et al; Asymmetric Synthesis of Lometrexol ((6R)-5,10-Dideaza-5,6,7,8-tetrahydrofolic Acid); J. Org. Chem. 1994; vol. 59; pp. 7038-7045.

Oct. 18, 2013 Notification of the First Office Action issued in Chinese Patent Application No. 201210044049.8 (with translation).

May 24, 2012 Search Report issued in International Patent Application No. PCT/CN2012/071243 (with translation).

May 24, 2012 Written Opinion of the International Searching Authority issued in International Patent Application No. PCT/CN2012/071243 (with translation).

\* cited by examiner

ARYL GLYCOSIDE COMPOUND, PREPARATION METHOD AND USE THEREOF

TECHNICAL FIELD

This invention relates to a kind of aryl glycoside compound, its pharmaceutically acceptable salt, optical isomer or prodrug, its preparation and the use, as well as the pharmaceutical composition containing the said compounds.

BACKGROUND ART

Sodium-dependent glucose cotransporters (SGLTs) play a key role in maintaining human plasma glucose stable. SGLTs have been found in intestine (SGLT1) and kidney (SGLT1 and SGLT2). Renal SGLT reabsorbs glucose from the renal filtrate, thereby preventing the loss of glucose from urine. 98% of glucose is reabsorbed in the kidney by SGLT2, and only the remaining 2% is reabsorbed by SGLT1. Inhibition of SGLT2 can specifically inhibit the reabsorption of glucose by kidney and increase the excretion of glucose in the urine, which may normalize the plasma glucose for diabetics. Therefore, the inhibitors of SGLT, particularly SGLT2, are promising candidates for antidiabetic drugs (Handlon, A. L., Expert Opin. Ther. Patents (2005) 15 (11):1531-1540).

So far, a lot of pharmaceutical companies have developed a series of SGLT2 inhibitors, such as those described in: Handlon, A. L., Expert Opin. Ther. Patents (2005) 15 (11): 1531-1540; William N. W., Journal of Medicinal Chemistry, 2009, Vol. 52, No. 7, 1785-1794; Chao, E. C. et al., Nature Reviews Drug Discovery, 2010, Vol. 9, No. 7, 551-559. Aryl glycosides as SGLT2 inhibitors are also known by the following patent applications: WO 01/27128, WO 02/083066, WO 03/099836, US 2003/0114390, WO 04/063209, WO 2005/012326, US 2005/0209166, US 2006/0122126, WO 2006/011502, US 2007/0293690, WO 2008/034859, WO 2008/122014 and WO 2009/026537.

CONTENTS OF THE INVENTION

The technical problem to be solved by the present invention is to provide a new kind of aryl glycoside derivatives or isomers, racemates, pharmaceutically acceptable salts thereof with an excellent inhibitory effect on SGLT, especially SGLT2, the use thereof and the pharmaceutical compositions containing the said derivative. The present invention is also to provide a process for preparing the compounds provided by the invention.

The present invention relates to an aryl glycoside compound of formula I or formula I', or a pharmaceutically acceptable salt, optical isomer or prodrug thereof;

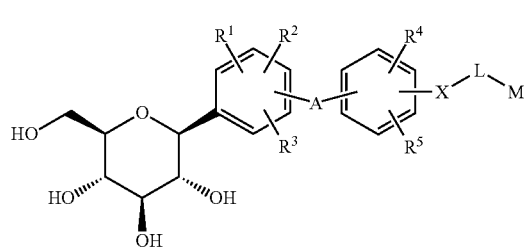

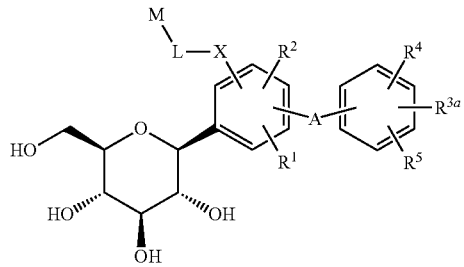

wherein, X is O, S, SO, $SO_2$, CO, $CONR^6$, NHCO, $NHSO_2$ or a single bond;

L is $C_1$-$C_6$ alkylene, ($C_1$-$C_6$ alkylene)-($C_3$-$C_{10}$ cycloalkylene) or ($C_1$-$C_6$ alkylene)-($C_3$-$C_{10}$ cycloalkylene)-($C_1$-$C_6$ alkylene), and each methylene group in said cycloalkylene is optionally replaced by O, N, or S;

M is 4-membered cycloheteroalkyl; with the proviso that when M is azetidinyl and L is linked with the nitrogen atom of M, then X-L is not $O(CH_2)_m CH(OR^{6f})CH_2$ where m is 1 to 3 and $R^{6f}$ is hydrogen, alkyl or alkylcarbonyl;

$R^1$, $R^2$ and $R^3$ are independently selected from hydrogen, OH, —$OR^7$, alkyl, —$SR^{5i}$ or halogen, or two of $R^1$, $R^2$ and $R^3$ together with the carbons to which they are attached can form an annelated five, six or seven membered carbocycle or heterocycle which may contain 1 to 4 heteroatoms in the ring which are N, O, S, SO and/or $SO_2$;

$R^{3a}$, $R^4$ and $R^5$ are independently selected from hydrogen, OH, —$OR^{5a}$, —O-Aryl, —$OCH_2$-Aryl, alkyl, cycloalkyl, halogen, —CN, —$CO_2R^{5b}$, —$CO_2H$, $COR^{6b}$, —CH(OH)$R^{6c}$, —CH($OR^{5h}$)$R^{6d}$, —$CONR^{6a}R^{6e}$, —$NHCOR^{5c}$, —$NHSO_2R^{5d}$, —$NHSO_2$-Aryl, Aryl, —$SR^{5e}$, —$SOR^{5f}$, —$SO_2R^{5g}$, —$SO_2$-Aryl, or a five, six or seven membered heterocycle which may contain 1 to 4 heteroatoms in the ring which are N, O, S, SO and/or $SO_2$; or $R^4$ and $R^5$ together with the carbons to which they are attached form an annelated five, six or seven membered carbocycle or heterocycle which may contain 1 to 4 heteroatoms in the ring which are N, O, S, SO and/or $SO_2$;

$R^7$, $R^{5a}$, $R^{5b}$, $R^{5c}$, $R^{5d}$, $R^{5e}$, $R^{5f}$, $R^{5g}$, $R^{5h}$ and $R^{5i}$ are independently selected from alkyl (such as ethyl);

$R^6$, $R^{6a}$, $R^{6b}$, $R^{6c}$, $R^{6d}$ and $R^{6e}$ are independently selected from hydrogen, alkyl, aryl, alkylaryl or cycloalkyl, or $R^{6a}$ and $R^{6e}$ together with the nitrogen to which they are attached form an annelated five, six or seven membered heterocycle which may contain 1 to 4 heteroatoms in the ring which are N, O, S, SO and/or $SO_2$;

A is O, S, 1,1-cyclopropylidene, CHF, $CF_2$ or $(CH_2)_n$ where n is 1 to 3.

wherein, ($C_1$-$C_6$ alkylene)-($C_3$-$C_{10}$ cycloalkylene) indicates the group formed by bonding $C_1$-$C_6$ alkylene with $C_3$-$C_{10}$ cycloalkylene, such as

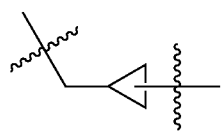

namely "methylene-cyclopropylene"; ($C_1$-$C_6$ alkylene)-($C_3$-$C_{10}$ cycloalkylene)-($C_1$-$C_6$ alkylene) indicates the group formed by bonding $C_1$-$C_6$ alkylene with $C_3$-$C_{10}$ cycloalkylene and $C_1$-$C_6$ alkylene sequentially, such as

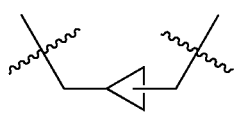

namely "methylene-cyclopropylene-methylene".

In the present invention, preferably, the substitution position of group A in said compound I is shown as follows:

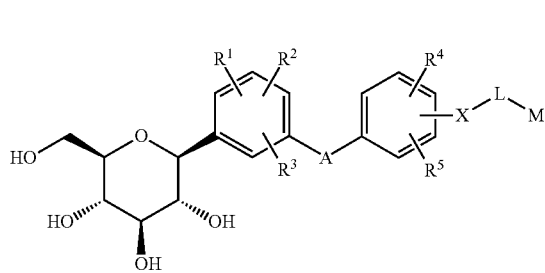

wherein the substitution position of group X is preferably para to group A;

preferably, the substitution position of group A in said compound I' is shown as follows:

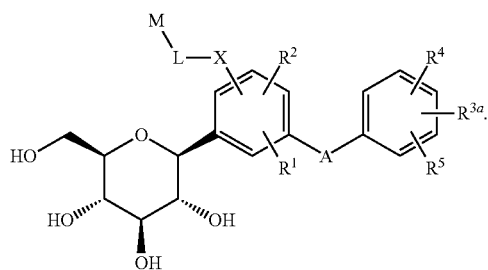

In the present invention, the substitution position of group X in said compound I, I', II, or II' is preferably para to group A.

In the present invention, said compound I has preferably the following structure IIA:

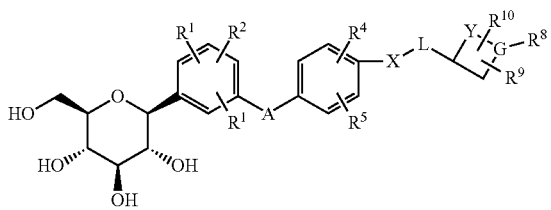

wherein, $R^1$, $R^2$, $R^3$, $R^4$, $R^5$, X, L and A have the meanings given above;

Y is carbon or oxygen, G is carbon, O, N, S, or SO, when G is O, S or SO, $R^8$ is none; Y and G can not be carbon at the same time; when G is N, $R^8$ is H, $C_1$-$C_3$ alkyl, carbonyl linked with $C_1$-$C_3$ alkyl, carbonyl linked with $C_1$-$C_6$ alkoxy (such as tert-butoxycarbonyl), $C_6$-$C_{10}$ aryl substituted by halogen (such as fluorine, chlorine, bromine or iodine), 4-membered cycloheteroalkyl having oxygen as the only one heteroatom, or $SO_2$ linked with $C_1$-$C_3$ alkyl;

$R^9$ and $R^{10}$ are independently selected from hydrogen, $C_1$-$C_6$ alkyl, halogen (such as fluorine, chlorine, bromine or iodine), OH, cycloalkyl, $C_1$-$C_6$ alkoxy, $C_1$-$C_6$ alkylcarbonyloxy, amino, $C_1$-$C_3$ alkyl substituted by halogen (with monofluoromethyl or difluoromethyl being preferred), $C_1$-$C_6$ alkylamino, or $C_1$-$C_6$ alkylcabonylamino.

In the present invention, said compound I' has preferably the following structure II'A:

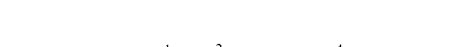

wherein, $R^1$, $R^2$, $R^{3a}$, $R^4$, $R^5$, X, L and A have the meanings given above;

G is carbon, O, N, S, or SO, when G is O, S or SO, $R^8$ is none; where G is N, $R^8$ is H, $C_1$-$C_3$ alkyl, carbonyl linked with $C_1$-$C_3$ alkyl, carbonyl linked with $C_1$-$C_6$ alkoxy or $SO_2$ linked with $C_1$-$C_3$ alkyl;

$R^9$ and $R^{10}$ are independently selected from hydrogen, $C_1$-$C_6$ alkyl, halogen (such as fluorine, chlorine, bromine or iodine), OH, cycloalkyl, $C_1$-$C_6$ alkoxy, $C_1$-$C_6$ alkylcarbonyloxy, amino, $C_1$-$C_3$ alkyl substituted by halogen, $C_1$-$C_6$ alkylamino, or $C_1$-$C_6$ alkylcabonylamino.

In the present invention, said compound IIA has preferably the following structure IIAa or IIAb:

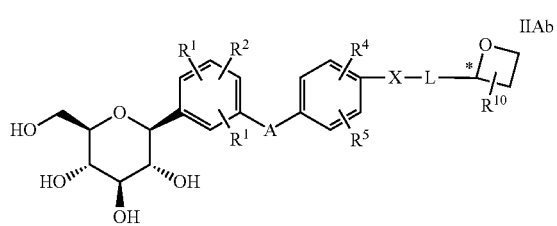

wherein, $R^1$, $R^2$, $R^3$, $R^4$, $R^5$, X, L, A, $R^8$ and $R^9$ have the meanings given above; G is O, N, S, or SO; * denotes racemic, or the absolute configuration of R or S;

wherein, $R^1$, $R^2$, $R^3$, $R^4$, $R^5$, X, L, A, and $R^{10}$ have the meanings given above; * denotes racemic, or the absolute configuration of R or S.
In the present invention, said compound I is more preferably any one of the following compounds:
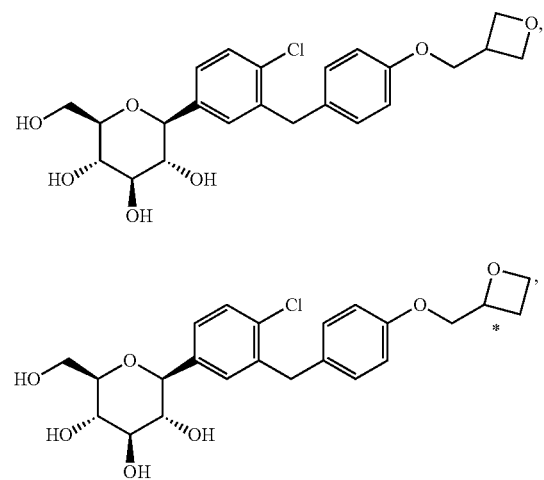
(* denotes racemic)
(* denotes optical isomerism)
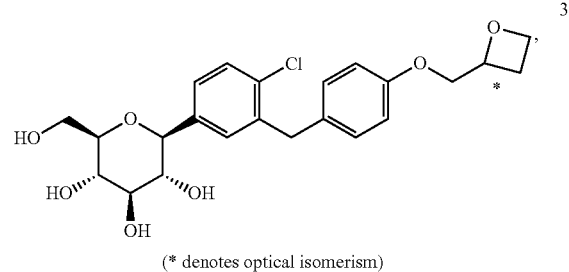
(* denotes optical isomerism)
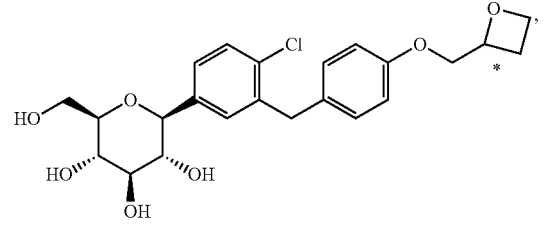
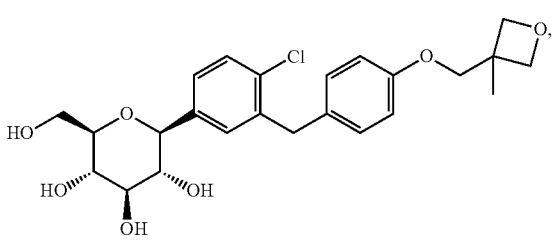
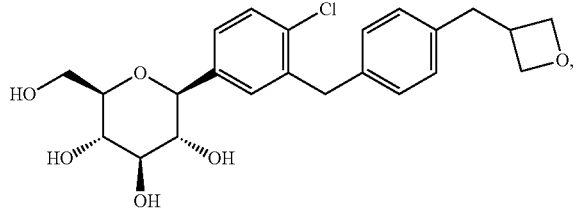
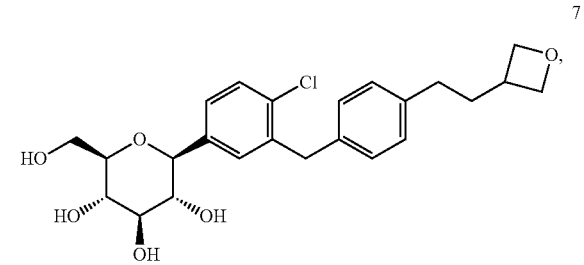
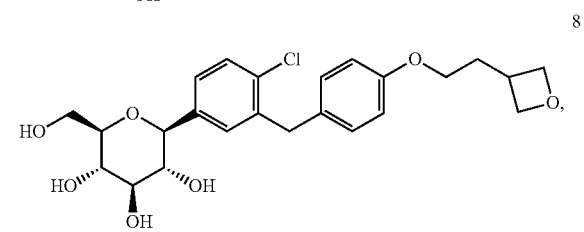
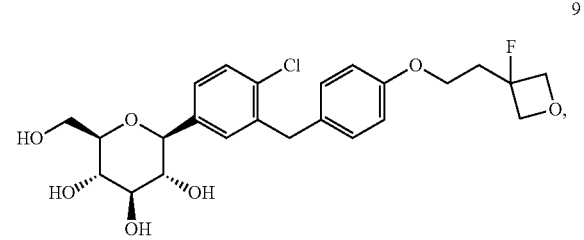
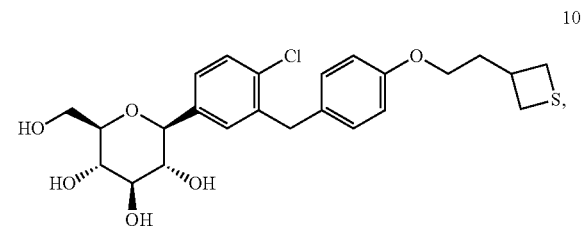
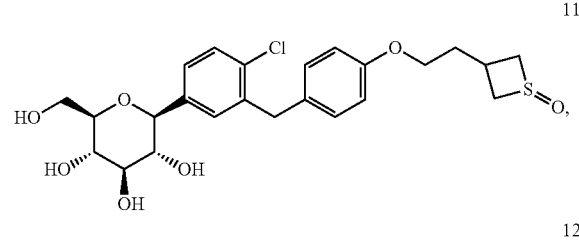
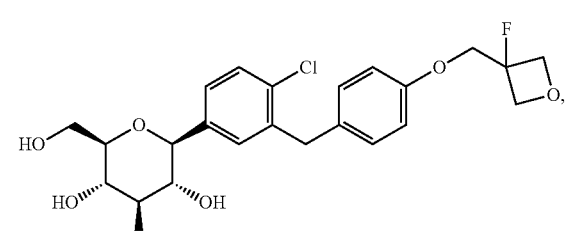

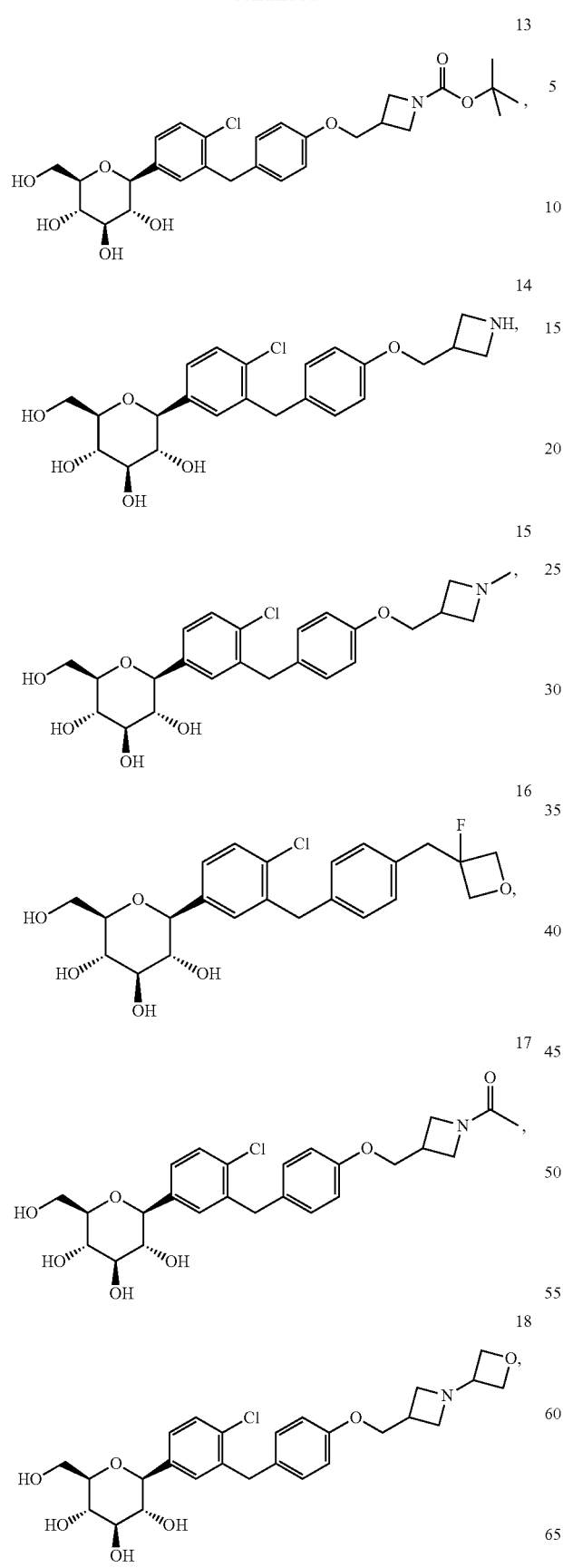
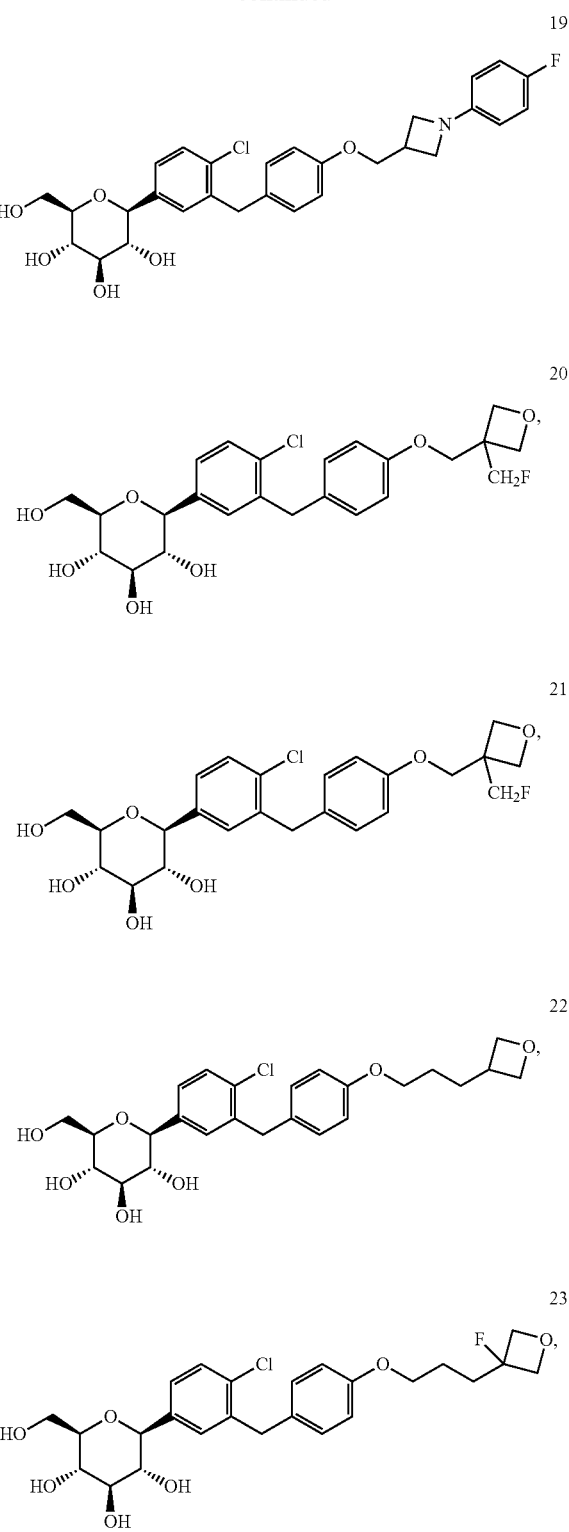
wherein, the absolute configurations of the carbon atoms labelled with * in compound 3 and 4 have enantiomeric relationship, and both compound 3 and 4 are optical isomers of compound 2.
In the present invention, said compound I' is preferably any one of the following compounds:

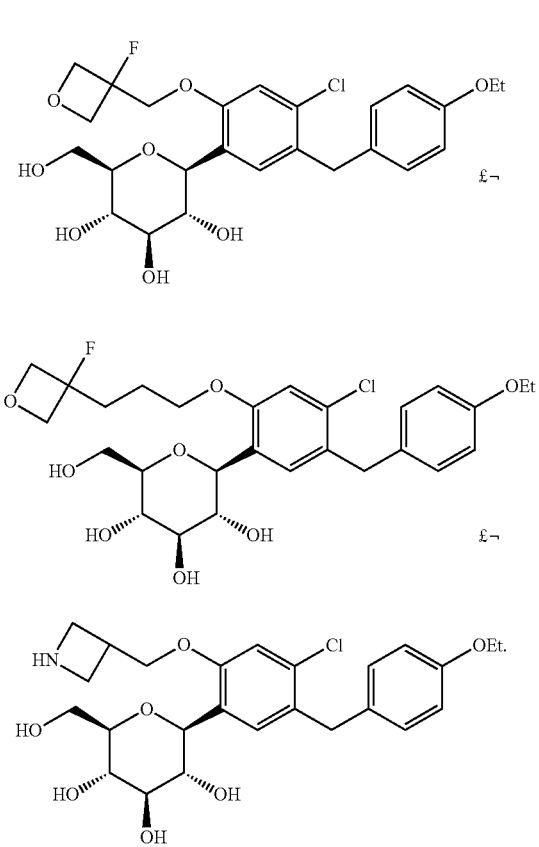

The present invention further relates to a process for preparing compound I or compound I', which is any one of the following three methods:

Method 1: compound Ia reacting with compound R'OTs or R'OMs to obtain compound I via a nucleophilic substitution reaction;

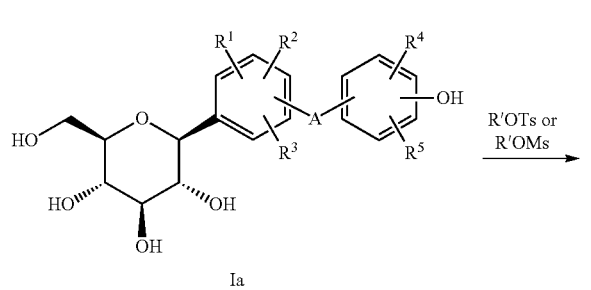

Method 2: deprotecting the acetyl protecting groups of hydroxyl groups of compound Ia' to obtain compound I;

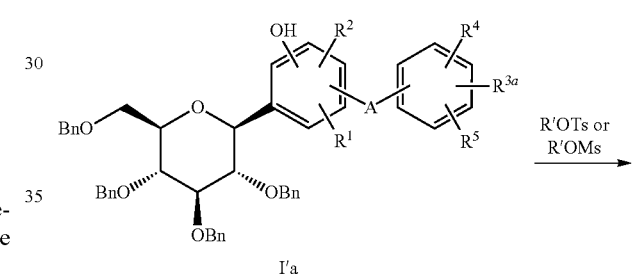

Method 3: compound I'a reacting with compound R'OTs or R'OMs via a nucleophilic substitution reaction followed by deprotecting the benzyl protecting groups of hydroxyl groups to obtain compound I';

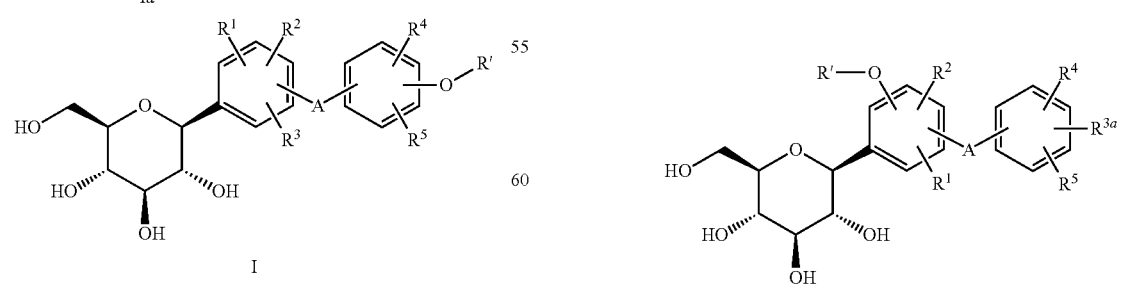

wherein, R'—OTs is

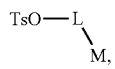

R'—OMs is

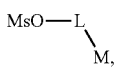

and each group and letter has the meanings given above.

In method 1, the methods and conditions used for said nucleophilic substitution reaction can be that commonly used for this kind of nucleophilic substitution reactions in this field, while the present invention uses particularly preferably the following methods and conditions: in a solvent, in the presence of base, the nucleophilic substitution reaction between compound Ia and R'OTs or R'OMs is carried out. Wherein, said solvent is preferably a polar solvent, such as dimethyl formamide or acetone, preferably dimethyl formamide. The amount of the solvent is preferably in the range from 20 to 100 mL/g relative to the mass of compound Ia. Said base is preferably one or more selected from potassium carbonate, sodium carbonate and cesium carbonate, more preferably cesium carbonate. The molar ratio of said base to compound Ia is in the range preferably from 1 to 3, more preferably from 1.5 to 2.5. The molar ratio of R'OTs or R'OMs to compound Ia is in the range preferably from 0.8 to 1.6, more preferably from 1 to 1.4. The temperature of said reaction is in the range preferably from 20 to 180° C., more preferably from 60 to 130° C. Said reaction is terminated preferably when completion is detected, which generally takes 2 to 15 hours.

In method 2, the methods and conditions used for said reaction to deprotect the acetyl protecting groups of hydroxyl groups can be that commonly used for this kind of reactions in this field, while the present invention uses particularly preferably the following methods and conditions: in a solvent, in the presence of base such as lithium hydroxide, sodium hydroxide or potassium hydroxide, preferably lithium hydroxide, the reaction to deprotect the acetyl protecting groups of hydroxyl groups of compound Ia' is carried out. Wherein, said solvent is preferably a mixed solvent of tetrahydrofuran, methanol and water, or a mixed solvent of methanol and water, more preferably a mixed solvent of tetrahydrofuran, methanol and water. The amount of solvent is preferably in the range from 50 to 200 mL/g relative to the mass of compound Ia'. The molar ratio of said base to compound Ia' is in the range preferably from 4 to 30, more preferably from 10 to 25. The temperature of said reaction is in the range preferably from –20 to 100° C., more preferably from 0 to 50° C. Said reaction is terminated preferably when completion is detected, which generally takes 0.5 to 2 hours.

In method 3, the methods and conditions used for said nucleophilic substitution reaction can be that commonly used for this kind of nucleophilic substitution reactions in this field, while the present invention uses particularly preferably the following methods and conditions: in a solvent, in the presence of base, the nucleophilic substitution reaction between compound I'a and R'OTs or R'OMs is carried out; wherein, said solvent is preferably a polar sovent; the amount of the solvent is preferably in the range from 20 to 100 mL/g relative to the mass of compound I'a; the base is preferably one or more selected from potassium carbonate, sodium carbonate and cesium carbonate, more preferably cesium carbonate; the molar ratio of said base to compound I'a is in the range preferably from 1 to 3, more preferably from 1.5 to 2.5; the molar ratio of said R'OTs or R'OMs to compound I'a is in the range preferably from 0.8 to 1.6, more preferably from 1 to 1.4; the temperature of said reaction is in the range preferably from 20 to 180° C., more preferably from 60 to 130° C.; said reaction is terminated preferably when completion is detected;

In method 3, the methods and conditions used for said reaction to deprotect the benzyl protecting groups of hydroxyl groups can be that commonly used for this kind of reactions in this field, while the present invention uses particularly preferably the following methods and conditions: under hydrogen atmosphere, in a solvent, in the presence of zinc halide such as $ZnBr_2$ or $ZnCl_2$, preferably $ZnBr_2$, the reaction catalyzed by palladium catalyst to deprotect the benzyl protecting groups of hydroxyl groups of compound I'b is carried out; wherein, said solvent is preferably methanol, ethanol or ethyl acetate, more preferably ethyl acetate; said palladium catalyst can be Pd/C or $Pd(OH)_2$/C, preferably $Pd(OH)_2$/C; the amount of solvent is preferably in the range from 20 to 200 mL/g relative to the mass of compound I'b; the molar ratio of said zinc halide to compound I'b is in the range preferably from 0.5% to 5%, more preferably from 1% to 2%; the temperature of said reaction is in the range preferably from –20 to 100° C., more preferably from 10 to 80° C.; the pressure of said hydrogen is in the range preferably from 1 to 2 atm, more preferably 1 atm; the reaction is terminated preferably when completion is detected.

In the present invention, said compound Ia' can be prepared by any one of the following methods:

(1) performing ether-forming reaction between compound Ib' and R'OH;

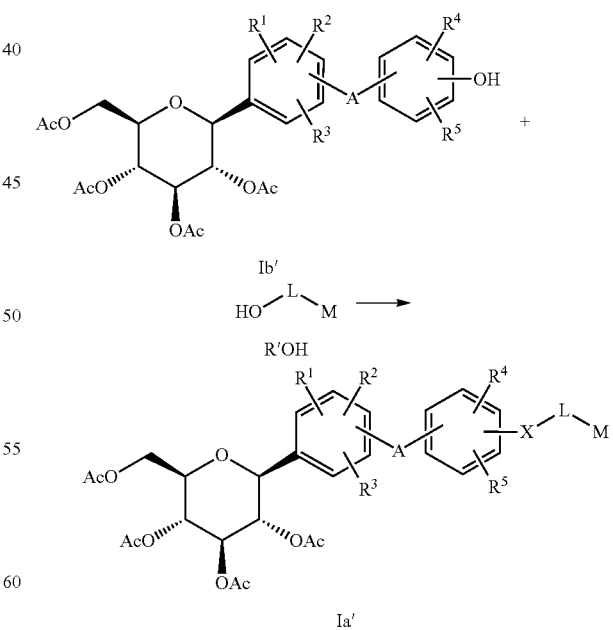

wherein, each group and letter has the meanings given above, X is O.

(2) performing coupling reaction between compound Ibb and Ib";

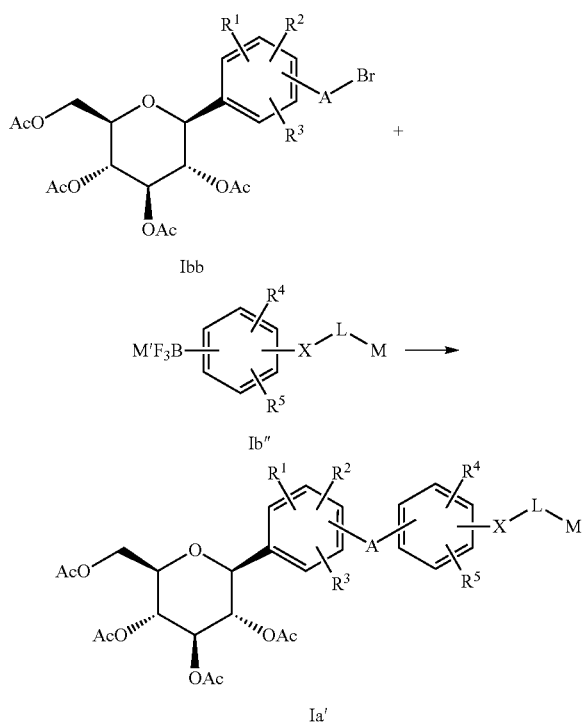

wherein, each group and letter has the meanings given above, A is preferably $CH_2$, M' is alkali metal such as potassium or sodium, preferably potassium.

The preparation of compound Ibb can refer to patent WO 2008/034859.

In method (1), the methods and conditions used for said ether-forming reaction can be that commonly used for this kind of reactions in this field, while the present invention uses particularly preferably the following methods and conditions: under the protection of nitrogen, in a solvent, in the presence of 1,1'-(azodicarbonyl)-dipiperidine (ADDP) and tri-n-butyl phosphine, the ether-forming reaction between compound Ib' and R'OH is carried out. Wherein, said solvent is preferably one or more selected from tetrohydrofuran, methylene chloride and toluene, more preferably tetrohydrofuran. The amount of solvent is preferably in the range from 20 to 200 mL/g relative to the mass of compound Ib'. The molar ratio of said R'OH to compound Ib' is in the range preferably from 0.8 to 8, more preferably from 2 to 5. The molar ratio of said 1,1'-(azodicarbonyl)-dipiperidine to compound Ib' is in the range preferably from 1 to 10, more preferably from 4 to 6. The molar ratio of said tri-n-butyl phosphine to compound Ib' is in the range preferably from 1 to 10, more preferably from 4 to 6. The temperature of said reaction is in the range preferably from –20 to 80° C., more preferably from 0 to 50° C. Said reaction is terminated preferably when completion is detected, which generally takes 2 to 15 hours.

In method (2), the methods and conditions used for said coupling reaction can be that commonly used for this kind of coupling reactions in this field, while the present invention uses particularly preferably the following methods and conditions: in a solvent, under the protection of inert gas, in the presence of base and palladium catalyst, the coupling reaction between compound Ibb and compound Ib" is carried out. Wherein, said inert gas can be argon and/or nitrogen. Said solvent is preferably one or more selected from tetrahydrofuran, toluene, 1,4-dioxane, ethylene glycol dimethyl ether and water, more preferably tetrahydrofuran and/or water, when the mixed solvent of tetrahydrofuran and water is used, the volume ratio of tetrahydrofuran to water is in the range preferably from 50:1 to 1:1, more preferably 10:1. The amount of solvent is preferably in the range from 20 to 100 mL/g relative to the mass of compound Ib". Said base is preferably one or more selected from potassium carbonate, cesium carbonate, sodium carbonate and potassium phosphate, more preferably cesium carbonate. The molar ratio of base to compound Ib" is in the range preferably from 1 to 10, more preferably from 3 to 5. Said palladium catalyst is preferably the catalyst commonly used for this type of coupling reaction, such as one or more selected from palladium acetate, tetrakis(triphenylphosphine)palladium and [1,1'-bis(diphenylphosphino)ferrocene]palladium dichloride, more preferably [1,1'-bis(diphenylphosphino)ferrocene]palladium dichloride. The molar ratio of catalyst to compound Ib" is in the range preferably from 0.005 to 0.5, more preferably from 0.01 to 0.1. The molar ratio of said reactant Ibb to reactant Ib" is in the range preferably from 0.5 to 2, more preferably from 0.9 to 1.5. The temperature of said reaction is in the range preferably from 20 to 120° C., more preferably from 70 to 90° C. Said reaction is terminated preferably when completion is detected, which generally takes 2 to 20 hours.

In the present invention, said compound I'a can be prepared by following method: the reaction to remove the silyl ether protecting group of compound I'b is carried out;

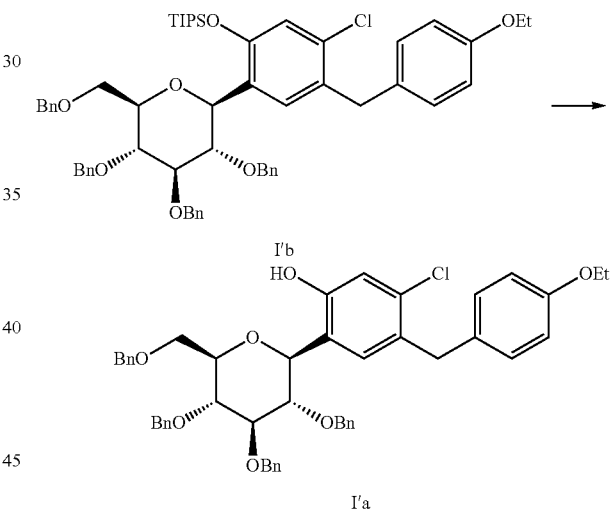

wherein, the methods and conditions used for said reaction to remove the silyl ether protecting group can be that commonly used for this kind of reactions in this field, while the present invention uses particularly preferably the following methods and conditions: in a solvent, in the presence of tetrabutyl ammonium fluoride, the silyl ether protecting group of the phenolic hydroxyl group is deprotected; wherein, said solvent is preferably tetrahydrofuran; the amount of solvent is in the range preferably from 5 to 50 mL/g relative to the mass of compound I'b; the molar ratio of said tetrabutyl ammonium fluoride to compound I'b is in the range preferably from 1 to 5, more preferably from 1 to 2; the temperature of said reaction is in the range preferably from –10 to 50° C., more preferably from 0 to 30° C.; said reaction is terminated preferably when completion is detected.

In the present invention, wherein said compound Ib' can be prepared by following method: the reaction to deprotect the acetyl protecting group of a hydroxyl group of compound Ic' is carried out;

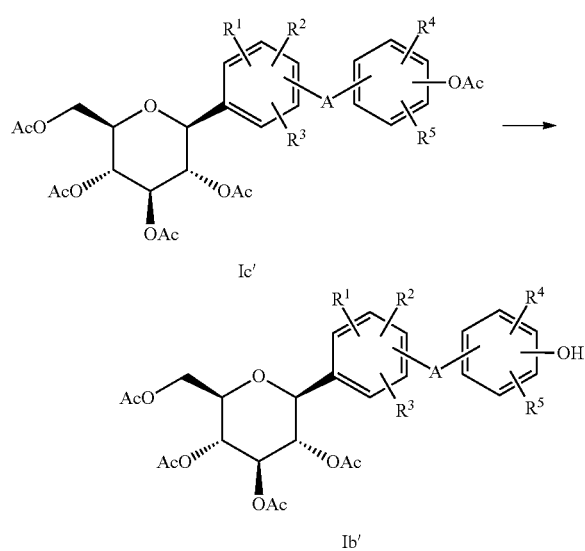

Ic′

Ib′ wherein, each group and letter has the meanings given above.

wherein, the methods and conditions used for said reaction to deprotect a acetyl protecting group of a hydroxyl group can be that commonly used for this kind of reactions to deprotect a acetyl protecting group of a hydroxyl group in this field, while the present invention uses particularly preferably the following methods and conditions: in a solvent, in the presence of ammonium acetate ($AcONH_4$), the acetyl protecting group of the phenolic hydroxyl group in compound Ic′ is deprotected selectively. Wherein, said solvent is preferably one or more selected from tetrahydrofuran, methanol and water, more preferably a mixed solvent of methanol and water. The amount of solvent is in the range preferably from 5 to 50 mL/g relative to the mass of compound Ic′. The molar ratio of said ammonium acetate to compound Ic′ is in the range preferably from 5 to 50, more preferably from 8 to 15. The temperature of said reaction is in the range preferably from 0 to 150° C., more preferably from 20 to 80° C. Said reaction is terminated preferably when completion is detected, which generally takes 5 to 20 hours.

In the present invention, said compound Ib″ can be prepared by following methods: the reaction between compound Ic″ and M′$HF_2$ (such as $KHF_2$) is carried out as follows;

Ic″

Ib″ wherein, each group and letter has the meanings given above.
wherein, said methods and conditions can be that commonly used for this kind of reactions in this field, while the present invention uses particularly preferably the following methods and conditions: in a solvent, the reaction between compound Ic″ and M′$HF_2$ is carried out. Wherein, said solvent is preferably one or more selected from acetonitrile, methanol and water, more preferably a mixed solvent of methanol and water. The amount of solvent is in the range preferably from 3 to 30 mL/g relative to the mass of compound Ic″. The molar ratio of said M′$HF_2$ to compound Ic″ is in the range preferably from 1 to 5, more preferably from 2 to 3. The temperature of said reaction is in the range preferably from 0 to 40° C., more preferably from 10 to 30° C. Said reaction is terminated preferably when completion is detected, which generally takes 1 to 5 hours.

In the present invention, said compound I′b can be prepared by following methods: the reduction reaction between compound I′c and silane is carried out;

I′c

I′b wherein, the methods and conditions used for said reduction reaction can be that commonly used for this kind of reactions in this field, while the present invention uses particularly preferably the following methods and conditions: in a solvent, in the presence of silane and trimethylsilyl trifluoromethanesulfonate, the reduction reaction is carried out, and meanwhile the phenolic hydroxyl group is protected by silyl reagent; wherein, said solvent is preferably one or more selected from methylene chloride, acetonitrile, toluene, tetrahydrofuran and diethyl ether, more preferably methylene chloride; the amount of solvent is in the range preferably from 20 to 100 mL/g relative to the mass of compound I′c; said silane is preferably triethyl silane or triisopropyl silane, more preferably triisopropyl silane; the molar ratio of said silane to compound I′c is in the range preferably from 1 to 5, more preferably from 1 to 2; the molar ratio of TMSOTf to compound I′c is in the range preferably from 0.5 to 2, more preferably from 0.9 to 1.2; the temperature of said reaction is in the range preferably from −100 to 10° C., more preferably from −80 to −20° C.; said reaction is terminated preferably when completion is detected.

In the present invention, said compound Ic′ can be prepared by following method: a hydroxyl acetylation reaction is carried out with compound Id′;

17

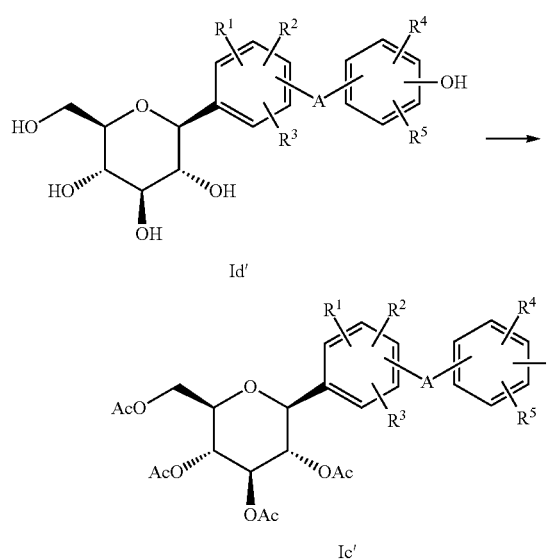

wherein, each group and letter has the meanings given above.

Wherein, the methods and conditions used for said hydroxyl acetylation reaction can be that commonly used for this kind of reactions in this field, the present invention uses particularly preferably the following methods and conditions: in a solvent, the hydroxyl acetylation reaction between compound Id' and acetic anhydride is carried out under basic condition. Wherein, said solvent is preferably one or more selected from methylene chloride, tetrahydrofuran, N,N-dimethyl formamide and pyridine, more preferably methylene chloride. The base mentioned in the "basic condition" is preferably a mixture of 4-dimethylaminopyridine and other organic bases, said "other organic bases" is preferably one or more selected from triethylamine, diisopropyl ethyl amine and pyridine, more preferably pyridine. The amount of solvent is in the range preferably from 10 to 100 mL/g relative to the mass of compound Id'. The molar ratio of said acetic anhydride to compound Id' is in the range preferably from 4 to 20, more preferably from 8 to 15. The molar ratio of said other organic bases to compound Id' is in the range preferably from 5 to 20, more preferably from 8 to 15. The molar ratio of 4-dimethylaminopyridine to compound Id' is in the range preferably from 0.01 to 1, more preferably from 0.05 to 0.2. The temperature of said reaction is in the range preferably from 0 to 100° C., more preferably from 20 to 50° C.; said reaction is terminated preferably when completion is detected, which generally takes 0.5 to 2 hours.

In the present invention, said compound Ic″ can be prepared by following method: the reaction between compound Id″ and bis(pinacolato)diboron is carried out;

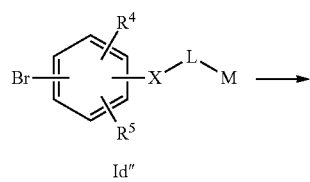

18

-continued wherein, each group and letter has the meanings given above.

Wherein, said methods and conditions can be that commonly used for this kind of reactions in this field, while the present invention uses particularly preferably the following methods and conditions: in a solvent, under the protection of inert gas, in the presence of weak base and palladium catalyst, the reaction between compound Id″ and bis(pinacolato)diboron is carried out. Wherein, said inert gas can be nitrogen or argon. Said solvent is preferably one or more selected from dimethylsulfoxide, N,N-dimethyl formamide, 1,4-dioxane and toluene, more preferably dimethylsulfoxide. The amount of solvent is in the range preferably from 10 to 100 mL/g relative to the mass of compound Id″. Said weak base is preferably triethylamine, sodium acetate and/or potassium acetate, more preferably potassium acetate. The molar ratio of said weak base to compound Id″ is in the range preferably from 1 to 5, more preferably from 1 to 3. The molar ratio of said bis(pinacolato)diboron to compound Id″ is in the range preferably from 1 to 2, more preferably from 0.9 to 1.5. Said palladium catalyst is preferably the catalyst commonly used for this type of reaction, such as one or more selected from bis(triphenylphosphine)palladium dichloride and [1,1'-bis(diphenylphosphino)ferrocene]palladium dichloride, more preferably bis(triphenylphosphine)palladium dichloride. The molar ratio of catalyst to compound Id″ is in the range preferably from 0.005 to 0.5, more preferably from 0.01 to 0.20. The temperature of said reaction is in the range preferably from 50 to 150° C., more preferably from 80 to 120° C. Said reaction is terminated preferably when completion is detected, which generally takes 5 to 20 hours.

In the present invention, said compound I'c can be prepared by following method: the condensation reaction between compound I'd and compound I'e is carried out;

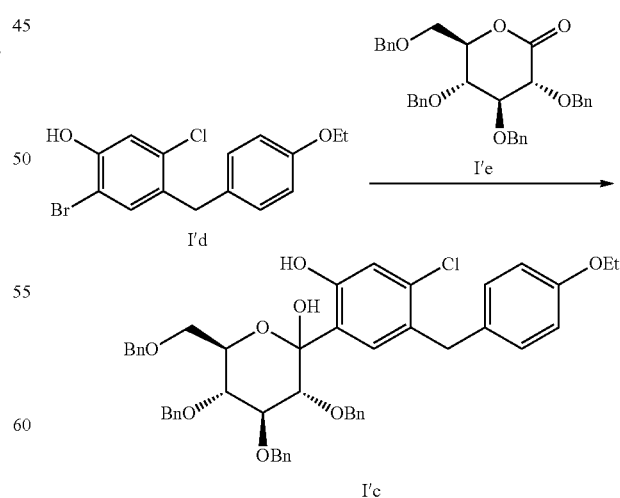

wherein, the methods and conditions used for said condensation reaction can be that commonly used for this kind of reactions in this field, while the present invention uses particularly preferably the following methods and conditions: in a solvent, treating compound I'd with NaH, followed by coupling with compound I'e in the presence of organic lithium compound; wherein, said solvent is preferably one or more selected from diethyl ether, methylene chloride, toluene, n-hexane and tetrahydrofuran, more preferably tetrahydrofuran, or the mixture of tetrahydrofuran and toluene; the amount of solvent is in the range preferably from 2 to 20 mL/g relative to the mass of compound I'd; the molar ratio of said NaH to compound I'd is in the range preferably from 0.9 to 2, more preferably from 1 to 1.5; said organic lithium compound is preferably n-butyl lithium, sec-butyl lithium or tert-butyl lithium; the molar ratio of said organic lithium compound to compound I'd is in the range preferably from 0.9 to 2, more preferably from 1 to 1.3; the molar ratio of said compound I'e to compound I'd is in the range preferably from 0.9 to 1.5, more preferably from 1 to 1.2; the reaction temperature for the reaction between compound I'd and NaH is in the range preferably from –10 to 10° C., more preferably from 0 to 10° C.; the reaction temperature for the coupling is in the range preferably from 0 to –100° C., more preferably from –10 to –80° C.; all the reactions are terminated preferably when completion is detected.

In the present invention, the preparation of compound Id" can refer to the method described in references: *J. Am. Chem Soc.*, 2009, 131, 2786-2787; *Angew. Chem. Int. Ed.*, 2010, 49, 3524-3527 and patent WO 2008/0021032, page 81-83. The preparation of compound I'd can refer to reference: *Bioorg. Med. Chem.*, 2011, 19, 5468-5479. The preparation of compound I'e can refer to reference: *J. Org. Chem.*, 1967, 32 (8), 2531-2534.

In the present invention, said compound Id' can be prepared by following method: a reaction to remove the methoxy group is carried out with compound Ie';

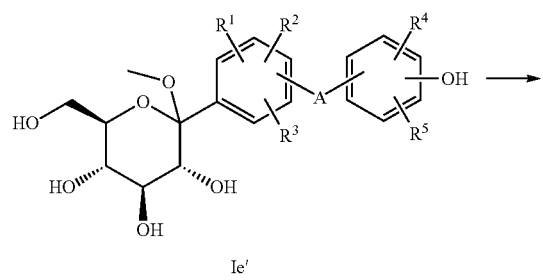

Ie'

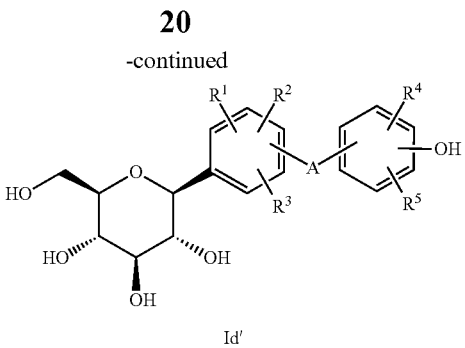

Id' wherein, each group and letter has the meanings given above.

Wherein, the methods and conditions used for said reaction to remove the methoxy group can be that commonly used for this kind of reactions in this field, while the present invention uses particularly preferably the following methods and conditions: in a solvent, in the presence of silane and boron trifluoride, the reaction to remove the methoxy group is carried out. Wherein, said solvent is preferably one or more selected from methylene chloride, acetonitrile, toluene, tetrahydrofuran and diethyl ether, more preferably methylene chloride or acetonitrile. The amount of solvent is in the range preferably from 10 to 100 mL/g relative to the mass of compound Ie'. Said silane is preferably triethyl silane or triisopropyl silane. The molar ratio of said silane to compound Ie' is in the range preferably from 1 to 5, more preferably from 2 to 3. The molar ratio of said boron trifluoride to compound Ie' is in the range preferably from 0.5 to 5, more preferably from 1 to 2. The temperature of said reaction is in the range preferably from –50 to 50° C., more preferably from –15 to 10° C. Said reaction is terminated preferably when completion is detected, which generally takes 2 to 6 hours.

In the present invention, said compound Ie' can be prepared by following method: a condensation reaction between compound If' and f' followed by a methylation reaction between the resulting material and the methanol solution of methanesulphonic acid, a reaction to deprotect the trimethylsilyl groups of the hydroxyl groups and a reaction to remove the methoxymethyl group of the phenolic hydroxyl group is carried out;

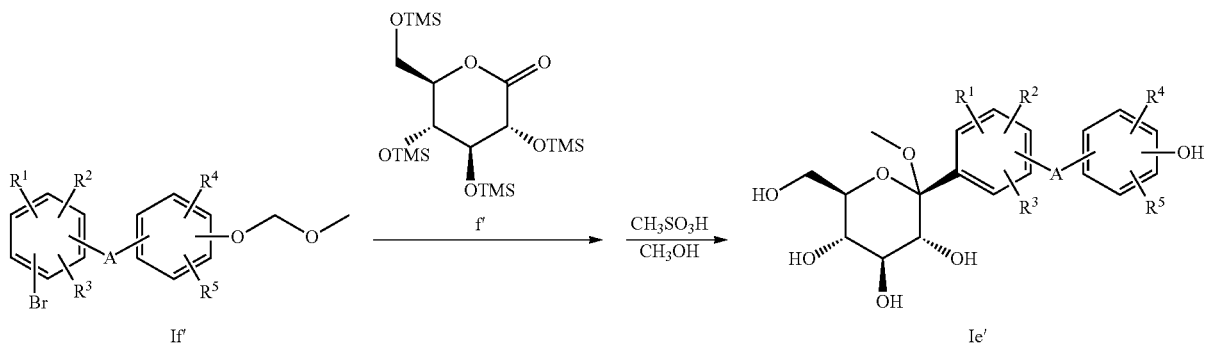

wherein, each group and letter has the meanings given above. The preparation of compound f can refer to reference: Carbohydr. Res., 1994, 260, 243-250.

Wherein, the methods and conditions used for said condensation reaction, methylation reaction, reaction to deprotect the trimethylsilyl groups of the hydroxyl groups and reaction to remove the methoxymethyl group of the phenolic hydroxyl group can be that commonly used for this kind of reactions in this field, while the present invention uses particularly preferably the following methods and conditions: in a solvent, under the protection of nitrogen, in the presence of organic lithium compound, the condensation reaction between compound If' and compound f' is carried out, then the methylation reaction between the resulting material and the methanol solution of methanesulphonic acid, the reaction to deprotect the trimethylsilyl groups of the hydroxyl groups and the reaction to remove the methoxymethyl group of the phenolic hydroxyl group are followed. Wherein, said solvent is preferably one or more selected from diethyl ether, methylene chloride, toluene, n-hexane and tetrahydrofuran, more preferably tetrahydrofuran, or the mixture of tetrahydrofuran and toluene. The amount of solvent is in the range preferably from 5 to 50 mL/g relative to the mass of compound If'. Said organic lithium compound is preferably n-butyl lithium, sec-butyl lithium or tent-butyl lithium; the molar ratio of said organic lithium compound to compound If' is in the range preferably from 0.9 to 2, more preferably from 1 to 1.3. The molar ratio of said compound f' to compound If' is in the range preferably from 0.9 to 2, more preferably from 1 to 1.3. The molar ratio of said methanesulphonic acid to compound If' is in the range preferably from 2 to 20, more preferably from 8 to 12. The temperature for said condensation reaction is in the range preferably from 0 to −100° C., more preferably from −10 to −80° C. The temperature for the methylation reaction and the reaction to deprotect the trimethylsilyl groups of the hydroxyl groups is in the range preferably from 0 to −100° C., more preferably from −30 to −80° C. All the three reactions are terminated preferably when completion is detected.

In the present invention, said compound If' can be prepared by following method: a nucleophilic substitution reaction between compound Ig' and chloromethyl ether is carried out;

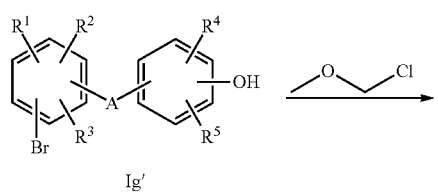

-continued wherein, each group and letter has the meanings given above.

Wherein, the methods and conditions used for said nucleophilic substitution reaction can be that commonly used for this kind of reactions in this field, while the present invention uses particularly preferably the following methods and conditions: in a solvent, in the presence of base, the nucleophilic substitution reaction between compound Ig' and chloromethyl ether is carried out. Wherein, said solvent is preferably one or more selected from N,N-dimethyl formamide, dimethylsulfoxide, methylene chloride and acetonitrile, more preferably N,N-dimethyl formamide. The amount of solvent is in the range preferably from 15 to 50 mL/g relative to the mass of compound Ig'. Said base is preferably sodium hydride or diisopropyl ethylamine, more preferably NaH. The molar ratio of the base to compound Ig' is in the range preferably from 0.9 to 2, more preferably from 1 to 1.5. The molar ratio of said chloromethyl ether to compound Ig' is in the range preferably from 0.9 to 2, more preferably from 1 to 1.5. The temperature of said reaction is in the range preferably from 0 to 70° C., more preferably from 10 to 40° C. Said reaction is terminated preferably when completion is detected, which generally takes 1 to 5 hours.

In the present invention, the preparation of compound Ig' can refer to patent WO 2009/026537. Those of skill in the art should be understood that, after knowing the structures of the compounds of the present invention, the compounds of the invention can be obtained through a variety of well-known methods in the art with the use of known materials, such as chemical synthesis or extraction method from plants, these methods are also included in the present invention. Unless otherwise stated or preparation method is provided, the raw materials used in preparing the compounds of the invention or an intermediate thereof are known in the art or can be commercially available.

In the present invention, the preferred conditions of said preparation methods can be any combination, i.e. preferred examples of the present invention is obtained.

As a preferred embodiment of the present invention, the compounds of the present invention can be prepared through the following processes and descriptions.

1. Preparation of the Intermediates
Process 1:

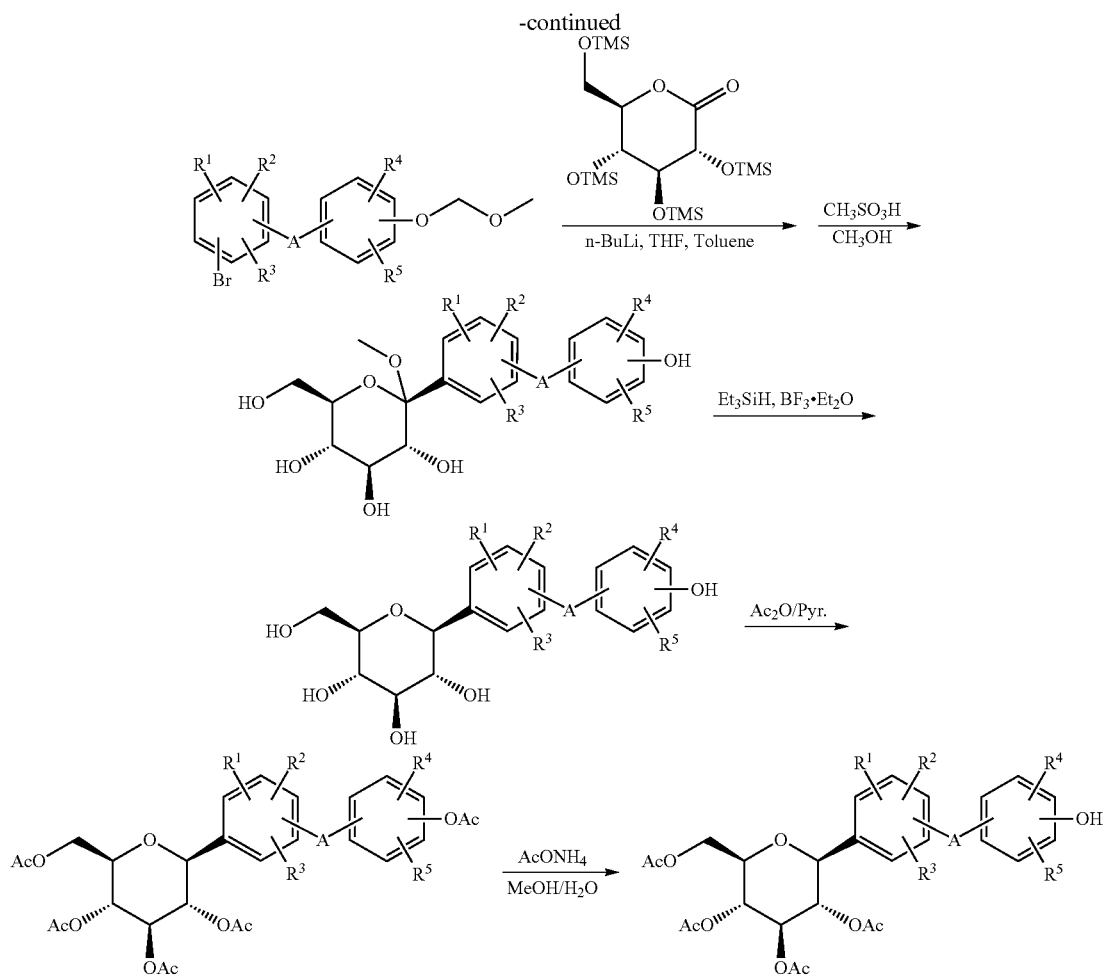
wherein, each group has the meanings given above.
Providing an example of a specific intermediate, the process is as follows:
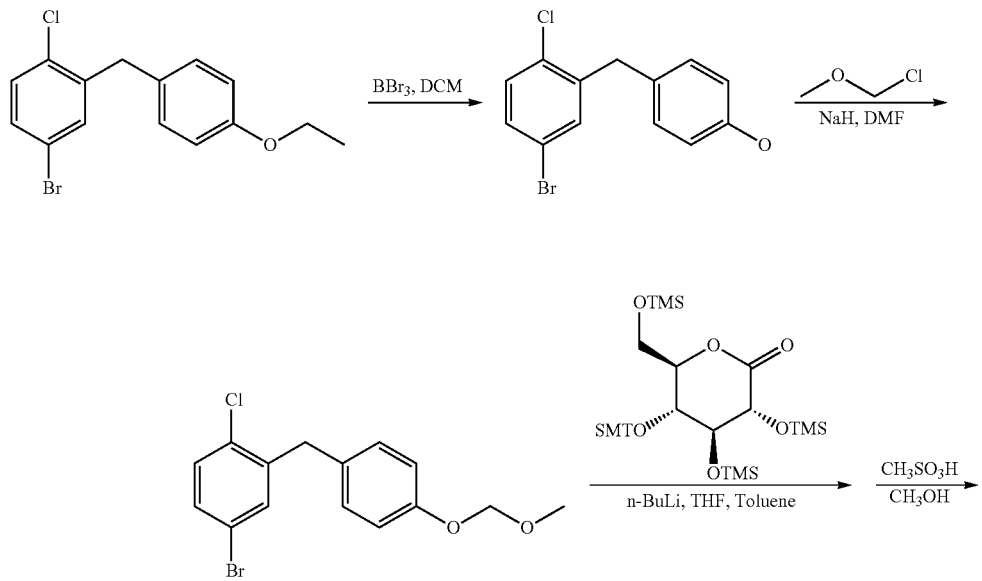

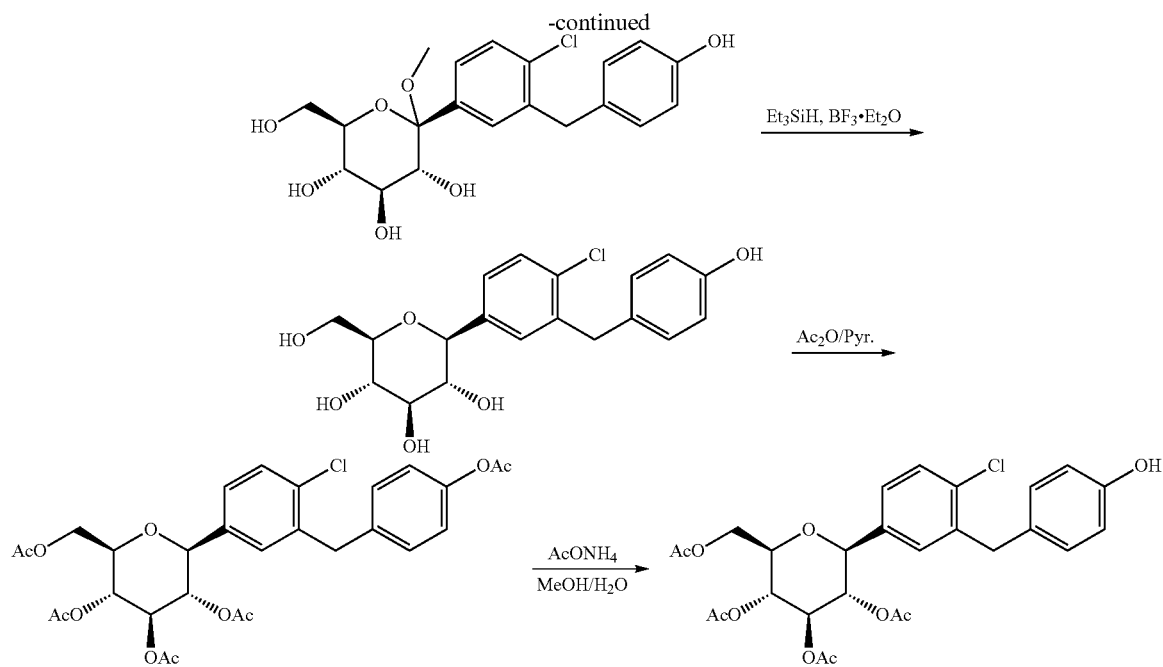
Process 2 (Preparation of Intermediates R'—OTS and R'—OMS):
Wherein, R'—OTs is
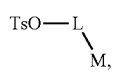
R'—OMs is
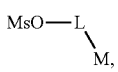
each group and letter has the meanings given above.
Example of Process 2:
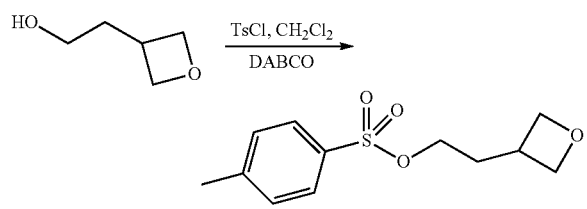
Process 3:
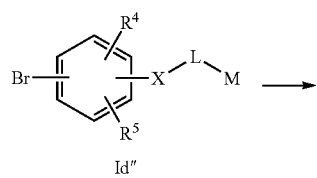
-continued
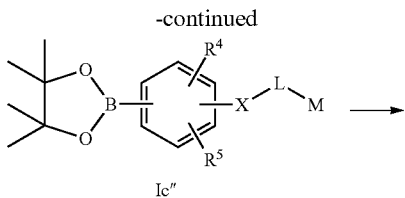
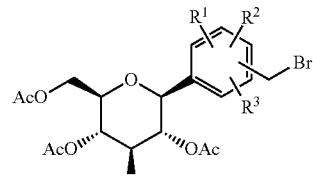
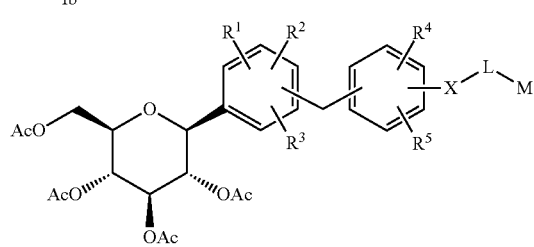
Example of Process 3:
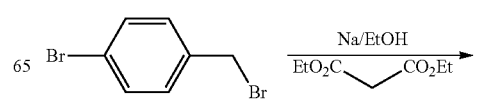

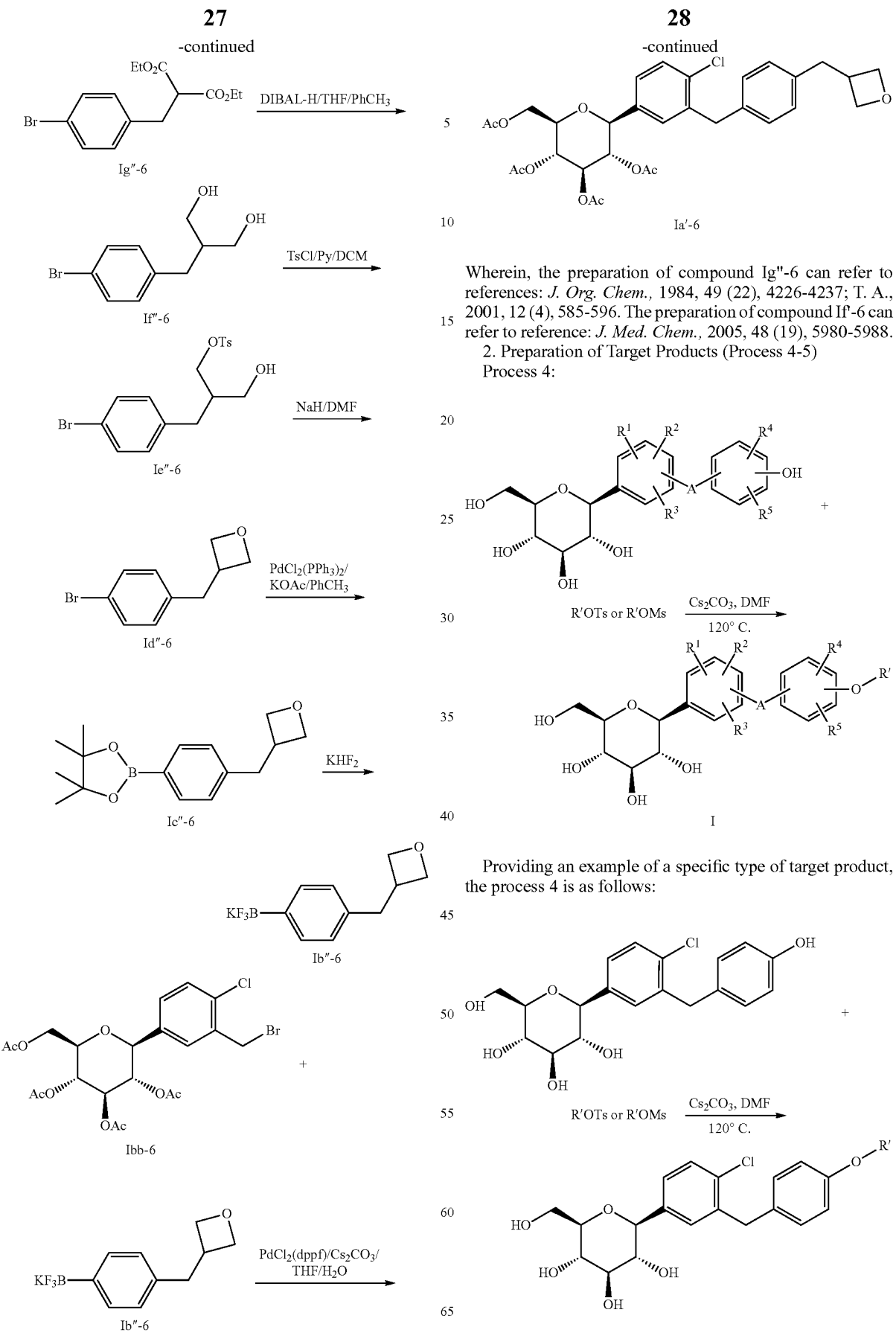
Wherein, the preparation of compound Ig″-6 can refer to references: *J. Org. Chem.*, 1984, 49 (22), 4226-4237; T. A., 2001, 12 (4), 585-596. The preparation of compound If′-6 can refer to reference: *J. Med. Chem.*, 2005, 48 (19), 5980-5988.
2. Preparation of Target Products (Process 4-5)
Process 4:
Providing an example of a specific type of target product, the process 4 is as follows:

wherein, R'—OTs is
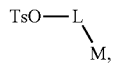
R'—OMs is
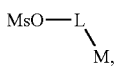
each group and letter has the meanings given above.
Process 5
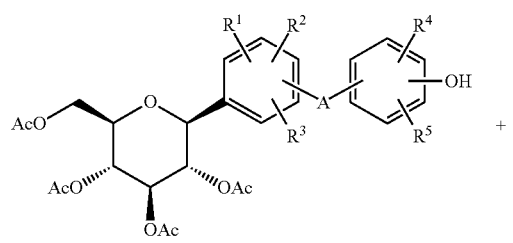
Providing an example of a specific type of target product, the process 5 is as follows:
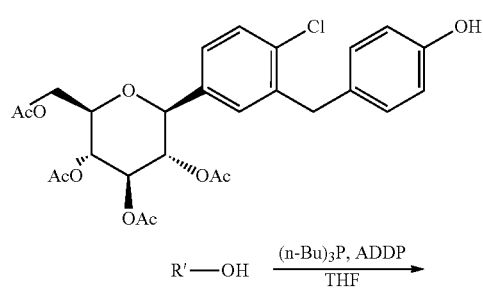
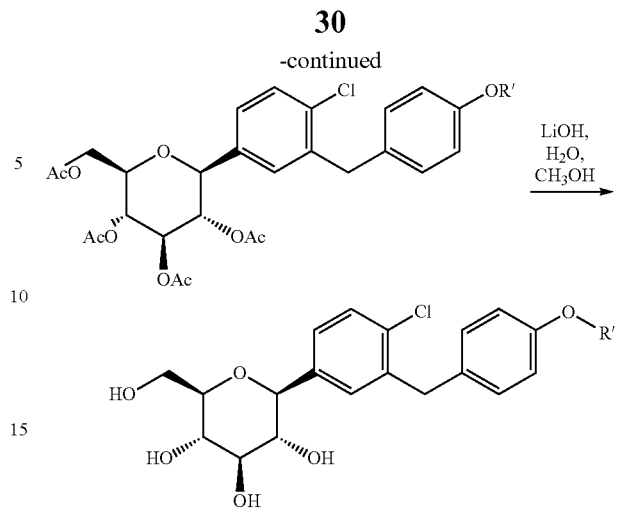
R' OH is
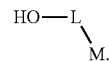
wherein, ADDP is the abbreviation of azodicarbonyl dipiperidine, each group and letter has the meanings given above.
Process 6
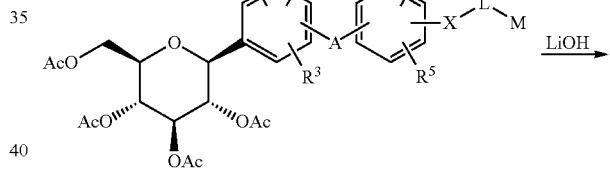
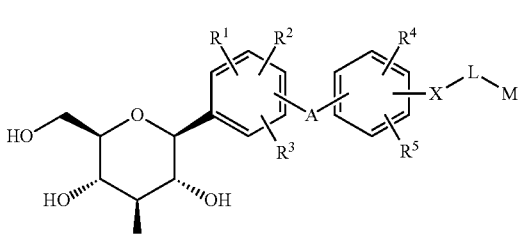
Example of Process 6:
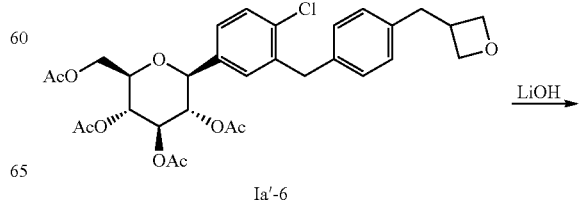

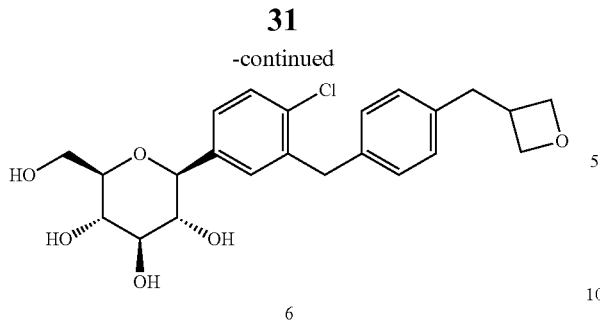

The present invention further relates to the intermediate compound shown as any one of the following structures used for preparing the aryl glucoside compound I mentioned above:

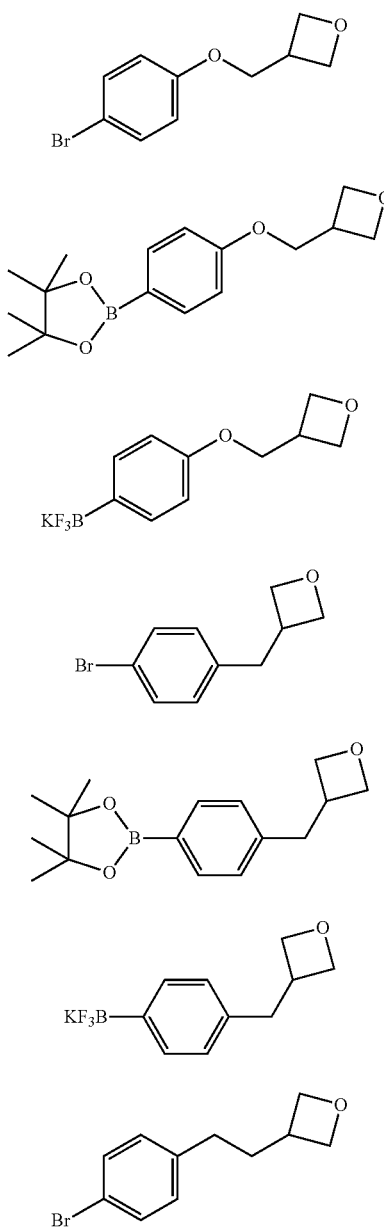

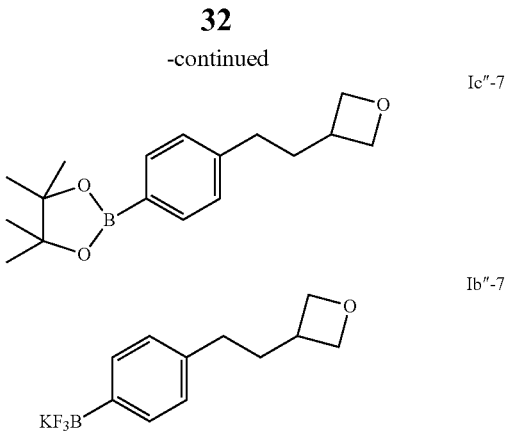

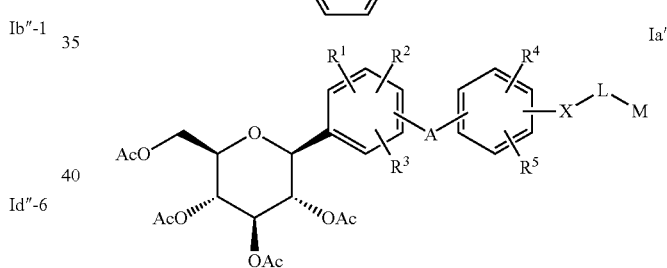

wherein, each group and letter has the meanings given above.

The present invention further relates to the use of the aryl glucoside compound I or pharmaceutically acceptable salt, optical isomer, or prodrug thereof mentioned above in preparing sodium-dependent glucose cotransporter (preferably SGLT2) inhibitor.

In addition, the present invention relates to the use of the aryl glucoside compound I or pharmaceutically acceptable salt, optical isomer, or prodrug thereof mentioned above for preparing agents used for treating or delaying the development or attack of the following diseases or for increasing the level of high density lipoprotein, wherein said disease is selected from diabetes, diabetic retinopathy, diabetic neuropathy, diabetic nephropathy, delayed wound healing, insulin resistance, hyperglycemia, hyperinsulinemia, increase of the levels of fatty acid or glycerol in blood, hyperlipidemia, obesity, hypertriglyceridemia, syndrome X, diabetic complications or artery atherosclerosis or hypertension. Wherein said diabetes is preferably the type II diabetes mellitus.

In addition, the present invention relates to a pharmaceutical composition, wherein the composition comprises an effective dose of said aryl glucoside compound I or pharmaceutically acceptable salt, optical isomer, or prodrug thereof, and a pharmaceutically acceptable carrier or excipient. The pharmaceutical composition may be used for preparing agents used for treating or delaying the development or attack of the following diseases or for increasing the level of high density lipoprotein, wherein said disease is selected from diabetes, diabetic retinopathy, diabetic neuropathy, diabetic nephropathy, delayed wound healing, insulin resistance, hyperglycemia, hyperinsulinemia, increase of the levels of fatty acid or glycerol in blood, hyperlipidemia, obesity, hypertriglyceridemia, syndrome X, diabetic complications or artery atherosclerosis or hypertension.

In another preferred embodiment, said composition may also comprise: an antidiabetic agent, an agent for treating the complications of diabetes, an anti-obesity agent, an antihypertensive agent, an antiplatelet agent, an antiatherosclerosis agent and/or a lipid-lowering agent which are non sodium-dependent glucose cotransporter inhibitors.

In another preferred embodiment, said antidiabetic agent is one or more selected from following: metformin, glyburide, glimepiride, glipizide, gliclazide, glipyride, pioglitazone, troglitazone, rosiglitazone, acarbose, miglitol, chlorpropamide, nateglinide, repaglinide, insulin, AC2993, AJ7677, AR-H039242, GI-262570, isaglitazone, JTT-501, KAD1129, KRP297, LY315902, NN-2344, NVP-DPP-728A, R-119702 or YM-440.

Unless otherwise indicated, the following terms when used in the descriptions and the claims of the present invention have the following meanings:

As used herein, the term "alkyl" (as used alone or as part of another group) refers to including branched and straight saturated aliphatic hydrocarbon radical containing 1 to 20 carbon atoms, preferably 1 to 10 carbon atoms, more preferably 1 to 8 carbon atoms, such as methyl, ethyl, n-propyl, isopropyl, n-butyl, tert-butyl, isobutyl, pentyl, hexyl, heptyl, octyl, nonyl, decyl, 4,4-dimethylpentyl, 2,2,4-trimethylpentyl, undecyl, dodecyl, and the various isomers thereof etc.; as well as such alkyl groups including 1 to 4 substituents which is selected from halogen (preferred F, Br, CI or I), alkyl, alkoxy, aryl, aryloxy, aryl substituted by aryl or diaryl, arylalkyl, arylalkoxy, alkenyl, alkynyl, cycloalkyl, cycloalkenyl, cycloalkylalkyl, cycloalkylalkoxy, optionally substituted amino, hydroxyl, hydroxyalkyl, acyl, aldehyde, heteroaryl, heteroaryloxy, cycloheteroalkyl, 4-membered cycloheteroalkyl, cycloheteroalkoxy, 4-membered cycloheteroalkoxy, arylheteroaryl, arylalkoxycarbonyl, heteroarylalkyl, heteroarylalkoxy, aryloxyalkyl, aryloxyaryl, alkylamino, acylamino, arylcarbonylamino, nitro, cyano, thiol, haloalkyl, trihaloalkyl and/or alkylthio. "$C_{x1}$-$C_{y1}$" alkyl (x1 and y1 are integer) described in the present invention with the range of the number of carbon atoms specified, such as "$C_1$-$C_3$ alkyl", except that the range of the number of carbon atoms differs from the range of the number of carbon atoms of "alkyl" defined in this paragraph, has the same definition as term "alkyl".

As used herein, the term "alkylene" (as used alone or as part of another group) refers to including branched and straight bivalent saturated aliphatic hydrocarbon radical containing 1 to 20 carbon atoms, preferably 1 to 10 carbon atoms, more preferably 1 to 8 carbon atoms, such as methylene, ethylene, n-propylene, isopropylene, n-butylene, tert-butylene, isobutylene, pentylene, hexylene, heptylene, octylene, nonylene, decylene, 4,4-dimethylpentylene, 2,2,4-trimethylpentylene, undecylene, dodecylene, and the various isomers thereof etc.; as well as such alkylene groups including 1 to 4 substituents which is selected from halogen (preferred F, Br, CI or I), alkyl, alkoxy, aryl, aryloxy, aryl substituted by aryl or diaryl, arylalkyl, arylalkoxy, alkenyl, alkynyl, cycloalkyl, cycloalkenyl, cycloalkylalkyl, cycloalkylalkoxy, optionally substituted amino, hydroxyl, hydroxyalkyl, acyl, aldehyde, heteroaryl, heteroaryloxy, cycloheteroalkyl, 4-membered cycloheteroalkyl, cycloheteroalkoxy, 4-membered cycloheteroalkoxy, arylheteroaryl, arylalkoxycarbonyl, heteroarylalkyl, heteroarylalkoxy, aryloxyalkyl, aryloxyaryl, alkylamino, acylamino, arylcarbonylamino, nitro, cyano, thiol, haloalkyl, trihaloalkyl, and/or alkylthio; one or more substituents mentioned above may form a ring together with the alkylene group, thereby forming a spiro ring.

The term "cycloalkyl" (as used alone or as part of another group) includes saturated or partially unsaturated (containing 1 or 2 double bonds) cyclic hydrocarbon radicals containing 1 to 3 rings, including monocyclic alkyl, bicyclic alkyl and tricyclic alkyl, containing a total of 3 to 20 carbons forming the rings, preferably 3 to 10 carbons, for example: cyclopropyl, cyclobutyl, cyclopentyl, cyclohexyl, cycloheptyl, cyclooctyl, cyclodecyl and cyclododecyl, cyclohexenyl; the cycloalkyl radicals may be optionally substituted by 1 to 4 substituents which is selected from halogen, alkyl, alkoxy, hydroxyl, aryl, aryloxy, arylalkyl, cycloalkyl, alkylamino, acylamino, oxo, acyl, arylcarbonylamino, amino, nitro, cyano, thiol and/or alkylthio and/or any of the alkyl substituents.

The term "cycloalkylene" (as used alone or as part of another group) includes saturated or partially unsaturated (containing 1 or 2 double bonds) cyclic hydrocarbon radicals containing 1 to 3 rings, including monocyclic alkylene, bicyclic alkylene and tricyclic alkylene, containing a total of 3 to 20 carbons forming the rings, preferably 3 to 10 carbons, for example: cyclopropylene, cyclobutylene, cyclopentylene, cyclohexylene, cycloheptylene, cyclooctylene, cyclodecylene and cyclododecylene, cyclohexenylene; the cycloalkylene radicals may be optionally substituted by 1 to 4 substituents which is selected from halogen, alkyl, alkoxy, alkylcarbonyloxy, alkoxycarbonyl, hydroxyl, aryl, aryloxy, arylalkyl, cycloalkyl, alkylamino, acylamino, acyl, arylcarbonylamino, amino, nitro, cyano, thiol and/or alkylthio and/or any of the alkyl substituents.

The term "alkoxy" refers to the cyclic or non-cyclic alkyl groups containing the indicated number of carbon atoms and having a connection through an oxygen bridge. Thus, "alkoxy" includes the definition of the alkyl group and the cycloalkyl group mentioned above.

The term "alkenyl" refers to straight chain, branched chain or cyclic non-aromatic hydrocarbon radicals having the indicated number of carbon atoms and at least one carbon-carbon double bond. Preferably there is one carbon-carbon double bond, and may have up to four non-aromatic carbon-carbon double bonds. Thus, "$C_2$-$C_{10}$ alkenyl" refers to an alkenyl group having 2 to 10 carbon atoms. "$C_2$-$C_6$ alkenyl" refers to an alkenyl group having 2 to 6 carbon atoms, including vinyl, propenyl, butenyl, 2-methyl-butenyl and cyclohexenyl. A double bond may locate at the straight-chain, branched or cyclic portion of an alkenyl group and, where specified, an alkenyl group may be substituted.

The term "alkynyl" refers to straight chain, branched chain or cyclic hydrocarbon radicals having the indicated number of carbon atoms and at least one carbon-carbon triple bond. It may have up to three carbon-carbon triple bonds. Thus, "$C_2$-$C_{10}$ alkynyl" refers to an alkynyl group having 2 to 10 carbon atoms. "$C_2$-$C_6$ alkynyl" refers to an alkynyl group having 2 to 6 carbon atoms, including ethynyl, propynyl, butynyl and 3-methyl-1-butynyl and the like.

As used herein, the term "aryl" refers to any stable monocyclic or bicyclic carbocyclic ring of up to 7 atoms in each ring, wherein at least one ring is an aromatic ring. Examples of the above-mentioned aryl group include phenyl, naphthyl, tetrahydronaphthyl, indanyl, biphenyl, phenanthryl, anthryl or acenaphthyl. It can be understood that if an aryl substituent is a bicyclic ring having one non-aromatic ring, then the connection is through the aromatic ring. It also includes the above aryl groups optionally substituted by 1 to 4 substituents which is selected from halogen (preferred F, Br, CI or I), alkyl, alkoxy, aryl, aryloxy, aryl substituted by aryl or diaryl, arylalkyl, arylalkoxy, alkenyl, alkynyl, cycloalkyl, cycloalkenyl, cycloalkylalkyl, cycloalkylalkoxy, optionally substituted amino, hydroxyl, hydroxyalkyl, acyl, aldehyde, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamino, acylamino, arylcarbonylamino, nitro, cyano, thiol, haloalkyl, trihaloalkyl, and/or alkylthio.

The term "alkylthio" refers to the cyclic or non-cyclic alkyl groups containing the indicated number of carbon atoms and having a connection through a sulfur atom. Thus, "alkylthio" includes the definition of the above alkyl group and cycloalkyl group.

The term "halogen" refers to fluorine, chlorine, bromine, iodine, or astatine.

The term "haloalkyl" refers to an alkyl group substituted by halogen at optionally position. Thus, the "haloalkyl" includes the definition of the above halogen and alkyl.

The term "haloalkoxy" refers to an alkoxy group substituted by halogen at optionally position. Thus, the "haloalkoxy" includes the definition of the above halogen and alkoxy.

The term "aryloxy" refers to aryl groups containing the indicated number of carbon atoms and having a connection through an oxygen bridge. Thus, "aryloxy" includes the definition of the above aryl group.

As used herein, the term "arylheterocycle" or "heteroaryl" refers to any stable monocyclic or bicyclic ring of up to 7 atoms in each ring, wherein at least one ring is an aromatic ring containing 1 to 4 heteroatoms selected from O, N, and S. Heteroaryl groups within the scope of this definition include, but are not limited to, acridinyl, carbazolyl, cinnolinyl, quinoxalinyl, pyrazolyl, indolyl, benzotriazolyl, furyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinolinyl. As the heterocycle defined below, "heteroaryl" should also be understood to include the N-oxide derivative of any nitrogen-containing heteroaromatic group. It can be understood that if a heteroaryl substituent is a bicyclic ring having one non-aromatic ring or one ring without heteroatom, then the connection is through the aromatic ring or the ring having heteroatom.

As used herein, the term "heterocycle" or "heterocyclic group" refers to 5 to 10 membered aromatic or non-aromatic heterocyclic ring having 1 to 4 heteroatoms selected from O, N, and S, bicyclic groups are also included. Therefore, the "heterocyclic group" includes the above heteroaryl groups, as well as their dihydro or tetrahydro analogs. Other examples of "heterocyclic group" include, but are not limited to, benzimidazolyl, benzofuranyl, benzofurazanyl, benzopyrazolyl, benzotriazolyl, benzothienyl, benzoxazolyl, carbazolyl, carbolinyl, cinnolinyl, furyl, imidazolyl, dihydroindolyl, indolyl, indazolyl, isobenzofuranyl, pseudoindolyl, isoquinoline, isothiazolyl, isoxazolyl, naphthalene pyrimidinyl, oxadiazolyl, oxazolyl, oxazolinyl, isoxazolinyl, oxetanyl, pyranyl, pyrazinyl, pyrazolyl, pyridazinyl, pyridopyridyl, pyridazinyl, pyridinyl, pyrimidinyl, pyrrolyl, quinazolinyl, quinolyl, quinoxalinyl, tetrahydropyranyl, tetrazolyl, tetrazopyridyl, thiadiazolyl, thiazolyl, thienyl, triazolyl, azetidinyl, 1,4-dioxanyl, hexahydrodiazepinyl, piperazinyl, piperidinyl, pyrrolidinyl, morpholinyl, thio-morpholinyl, dihydro-benzimidazolyl, dihydro-benzofuranyl, dihydro-benzothienyl, dihydro-benzoxazolyl, dihydro-furyl, dihydro-imidazolyl dihydro-indolyl, dihydro-isoxazolyl, dihydro-isothiazolyl, dihydro-oxadiazolyl, dihydro-oxazolyl, dihydro-pyrazinyl, dihydro-pyrazolyl, dihydropyridyl, dihydro-pyrimidinyl, dihydro-pyrrolyl, dihydro-quinolyl, dihydro-tetrazolyl, dihydro-thiadiazolyl, dihydro-thiazolyl, dihydro-thienyl, dihydro-triazolyl, dihydro-azetidinyl, methylenedioxybenzoyl, tetrahydrofuranyl and tetrahydrothienyl and its N-oxide. A heterocyclic group can be linked with other groups through a carbon atom or a heteroatom.

The term "cycloheteroalkyl" as used herein alone or as part of another group refers to a 5-, 6- or 7-membered saturated or partially unsaturated ring which includes 1 to 2 heteroatoms (such as nitrogen, oxygen and/or sulphur). Said cycloheteroalkyl groups may include 1 to 4 substituents, such as alkyl, halogen, oxo and/or any of alkyl susbstituents set out above. In addition, any of the cycloheteroalkyl rings can be fused to a cycloalkyl, aryl, heteroaryl or cycloheteroalkyl ring. A cycloheteroalkyl substituent can be linked with other groups through a carbon atom or a heteroatom.

The term "4-membered cycloheteroalkyl" as used herein alone or as part of another group refers to a 4-membered ring which includes 1 to 2 heteroatoms (such as nitrogen, oxygen or sulphur, and when the heteroatom is S, it can be S, SO or $SO_2$), such as

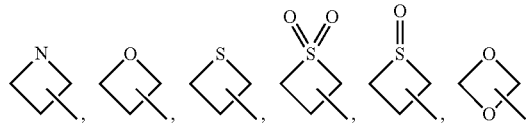

and the like. Said 4-membered cycloheteroalkyl groups may include 1 to 4 substituents, such as alkyl, halogen, oxo and/or any of alkyl susbstituents set out above. A 4-membered cycloheteroalkyl substituent can be linked with other groups through a carbon atom or a heteroatom.

In the present invention, the term "pharmaceutical composition" refers to a mixture of one or more aryl glycoside compounds described herein or a pharmaceutically acceptable salt or prodrug thereof and other chemical components such as pharmaceutically acceptable carriers and excipients. The purpose of the pharmaceutical composition is to facilitate administration of the compound on living organisms. The pharmaceutical composition may or may not contain another anti-diabetic agent and/or anti-hyperlipidemic agents, or other types of therapeutic agents.

Unless otherwise specified, the related materials and reagents in the present invention are commercially available.

The positive effect of the present invention is that: the aryl glycosides described in the present invention have excellent ability to inhibit SGLT2, and is a potent antidiabetic agent.

EMBODIMENTS

The following embodiments further illustrate the present invention, but the present invention is not limited thereto.

Example 1

4-(5-Bromo-2-chlorobenzyl)phenol

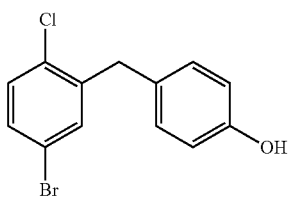 [SMILES: Oc1ccc(Cc2cc(Br)ccc2Cl)cc1]

At −78° C., to a stirred solution of 4-bromo-1-chloro-2-(4-ethoxybenzyl)benzene (8.47 g, 0.026 mol) (according to the synthesis procedure in the reference: *Journal of Medicinal Chemistry*, 2008, 51, 1145-1149) in dichloromethane (250 mL) was added slowly a solution of tribromoborane in dichloromethane (8 mL, 4 M) in drops, the mixture was stirred at −78° C. for further 30 minutes and then 1 hour at room temperature. Saturated aqueous sodium bicarbonate (200 mL) was added dropwise, the mixture was extracted for 3 times with ethyl acetate. The organic phases were combined and washed with saturated brine for one time, dried over anhydrous sodium sulfate. The solvent was evaporated under vacuum. The residue was purified by silica gel column chromatography (petroleum ether/ethyl acetate, 10:1) to afford the target compound.

Yield: 6.85 g (89% of theoretical value).
LC-MS (ESI): m/z=297/299 (Cl) [M+H]+.

Example 2

4-Bromo-1-chloro-2-(4-(methoxymethoxy)benzyl)-benzene

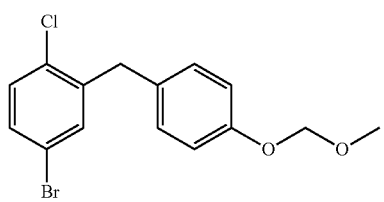 [SMILES: COCOc1ccc(Cc2cc(Br)ccc2Cl)cc1]

At 0° C., to a stirred solution of 4-(5-bromo-2-chlorobenzyl)phenol (6.85 g, 23 mmol) in dimethylformamide (100 mL) was added portionswise sodium hydride (60% in mineral oil, 1.01 g, 25.3 mmol), the mixture was stirred at 0° C. for further 30 minutes. Chloromethyl ether (2.02 g, 25.3 mmol) was slowly added in drops and when the addition finished, the mixture was stirred at room temperature for further 3 hours. Water (150 mL) was added, the mixture was extracted for two times with ethyl acetate, the combined organic phases were washed with saturated brine for one time and dried over anhydrous sodium sulfate. The solvent was evaporated under vacuum. The residue was purified by silica gel column chromatography (petroleum ether/ethyl acetate, 20:1) to afford the target compound.

Yield: 7.04 g (90% of theoretical value).
LC-MS (ESI): m/z=363/365 (Cl) [M+Na]+.

Example 3

1-Chloro-4-(1-methoxy-D-glucopyranose-1-yl)-2-(4-hydroxybenzyl)-benzene

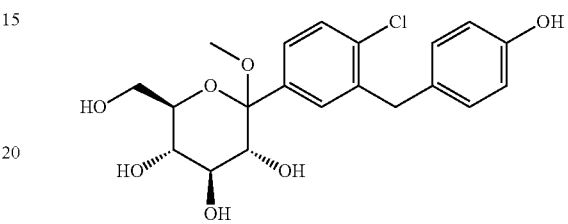

Under nitrogen, a solution of 4-bromo-1-chloro-2-(4-(methoxy-methoxy)benzyl)-benzene (1.17 g, 3.44 mmol) in anhydrous THF/toluene (2:1, 12 mL) was cooled to −78° C. n-BuLi (2.5 M in n-hexane, 1.5 mL) was added slowly in drops and when the addition finished, the mixture was stirred at −78° C. for further 30 minutes. The mixture was then transferred by cannule cooled by dry ice to a cooled (−78° C.) stirred solution of 2,3,4,6-tetra-O-(trimethylsilyl)-D-glucolactone (1.76 g, 3.78 mmol) in toluene (6 mL) at a rate that maintained the reaction temperature below −70° C. The mixture was stirred at −78° C. for further two hours. A solution of methanesulfonic acid in methanol (0.6 N, 6.3 mL) was added dropwise at −78° C., when the addition finished, the mixture was then stirred at room temperature for 16 hours. Saturated aqueous sodium bicarbonate (50 mL) was used to quench the reaction, the mixture was extracted for 3 times with ethyl acetate. The organic phases were combined, washed with saturated brine for one time and dried over anhydrous sodium sulfate. The solvent was evaporated under vacuum. The residue was used for the next step without further purification.

Yield: 1.06 g (75% of theoretical value).
LC-MS (ESI): m/z=433/435 (Cl) [M+Na]+.

Example 4

1-Chloro-4-(β-D-glycopyranose-1-yl)-2-(4-hydroxybenzyl)benzene

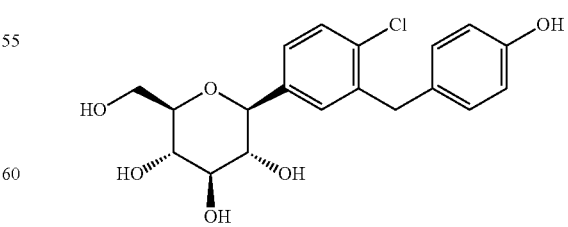

A solution of the 1-chloro-4-(1-methoxy-D-glucopyranose-1-yl)-2-(4-hydroxybenzyl)benzene (1.06 g, 2.83 mmol) in CH₂Cl₂/CH₃CN (1:1, 24 mL) gained above was cooled to −10° C. After addition of triethylsilane (660 mg, 5.66 mmol), BF₃.Et₂O (1.1 mL, 3.98 mmol) was added dropwise to the mixture at a rate that the reaction temperature was maintained below −5° C. When the addition finished, the mixture was stirred for 4 hours at 0° C. The reaction was then quenched by the addition of saturated aqueous sodium bicarbonate (50 mL). The organic phase was seperated and the aqueous phase was extracted for 3 times with ethyl acetate. The organic phases were combined, washed with saturated brine and dried over anhydrous sodium sulfate. The solvent was evaporated under vacuum. The residue was purified by silica gel column chromatography (dichloromethane/methanol, 15:1) to afford the target compound.

Yield: 0.37 g (38% of theoretical value).

¹HNMR (500 MHz, CD₃OD) δ: 7.16-7.25 (m, 3H), 6.91 (d, J=8.5 HZ, 2H), 6.58 (d, J=8.5 HZ, 2H), 3.97-4.01 (m, 1H), 3.89 (dd, J=15 Hz, 13 Hz, 2H), 3.77 (d, J=11 Hz, 1H), 3.57-3.60 (m, 1H), 3.28-3.35 (m, 3H), 3.17-3.21 (m, 1H).

LC-MS (ESI): m/z=403/405 (Cl) [M+Na]⁺.

Example 5

1-Chloro-4-(2,3,4,6-tetra-O-acetyl-β-D-glycopyranose-1-yl)-2-(4-acetoxy-benzyl)benzene

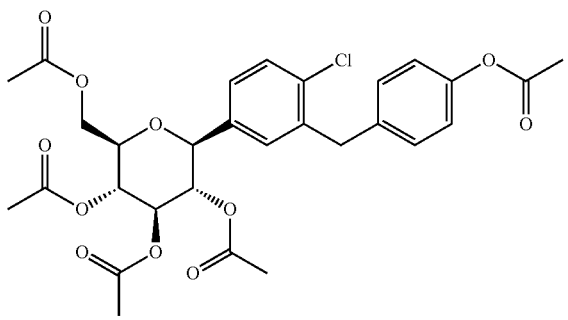 [SMILES: CC(=O)OC[C@H]1O[C@@H](c2ccc(Cl)c(Cc3ccc(OC(C)=O)cc3)c2)[C@H](OC(C)=O)[C@@H](OC(C)=O)[C@@H]1OC(C)=O]

A solution of 1-chloro-4-(β-D-glycopyranose-1-yl)-2-(4-hydroxy-benzyl)benzene (0.38 g, 1 mmol) in dichloromethane (10 mL) was cooled to 0° C., pyridine (790 mg, 10 mmol) was added, sequence followed by the addition of acetyl anhydride (1.02 g, 10 mmol) and DMAP (12 mg, 0.1 mmol). After stirred at room temperature for 30 minutes, the organic phase was washed in turn with water, hydrochloric acid (1 N), saturated aqueous sodium bicarbonate and saturated brine. The organic phase was dried over anhydrous sodium sulfate. The solvent was evaporated under vacuum to give white powder, which was used for the next step without further purification.

Yield: 0.56 g (95% of theoretical value).

¹HNMR (500 MHz, CDCl₃) δ: 7.29 (d, J=8.5 Hz, 1H), 7.13 (dd, J=2.0 Hz, 8.0 Hz, 1H), 7.08 (d, J=8.5 Hz, 2H), 7.05 (d, J=2.0 Hz, 1H), 6.93 (dd, J=2.0 Hz, 6.5 Hz, 2H), 5.22 (t, J=9.5 Hz, 1H), 5.13 (t, J=9.5 Hz, 1H), 4.99 (t, J=9.5 Hz, 1H), 4.26 (d, J=10.0 Hz, 1H), 4.18-4.22 (m, 2H), 4.07 (dd, J=2.5 Hz, 12.5 Hz, 1H), 4.01 (q, J=15.5 Hz, 2H), 2.21 (s, 3H), 2.01 (s, 3H), 1.97 (s, 3H), 1.92 (s, 3H), 1.62 (s, 3H).

LC-MS (ESI): m/z=613/615 (Cl) [M+Na]⁺.

Example 6

1-Chloro-4-(2,3,4,6-tetra-O-β-D-glycopyranose-1-yl)-2-(4-hydroxybenzyl)-benzene

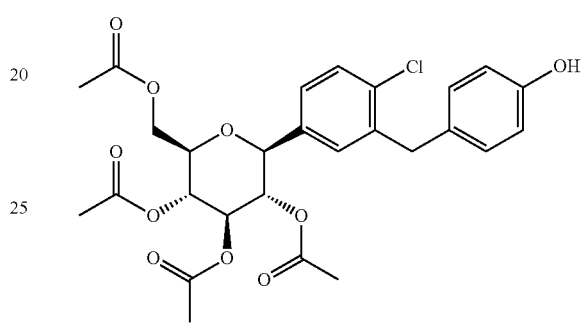

To a solution of 1-chloro-4-(2,3,4,6-tetra-O-acetyl-β-D-glycopyranose-1-yl)-2-(4-acetoxy-benzyl)benzene (0.56 g, 0.95 mmol) in THF/MeOH/H₂O (5:5:2, 12 mL) was added ammonium acetate (730 mg, 9.5 mmol). The mixture was stirred at 70° C. overnight, then the solvent was evaporated under vacuum. The residue was partitioned between water and ethyl acetate. The organic phase was washed with saturated brine for one time, dried over anhydrous sodium sulfate. The solvent was evaporated under vacuum. The residue was purified by silica gel column chromatography (petroleum ether/ethyl acetate, 1:5) to afford the target compound.

Yield: 0.35 g (67% of theoretical value).

LC-MS (ESI): m/z=571/573 (Cl) [M+Na]⁺.

¹HNMR (500 MHz, CDCl₃) δ: 7.35 (d, J=8.0 Hz, 1H), 7.18 (dd, J=2.0 Hz, 8.0 Hz, 1H), 7.07 (d, J=1.5 Hz, 1H), 7.02 (d, J=8.5 Hz, 2H), 6.75 (d, J=8.5 Hz, 2H), 5.26 (t, J=9.5 Hz, 1H), 5.20 (t, J=9.5 Hz, 1H), 5.05 (t, J=9.5 Hz, 1H), 4.81 (S, 1H), 4.31 (d, J=10.0 Hz, 1H), 4.22-4.28 (m, 2H), 4.14 (dd, J=1.5 Hz, 12.5 Hz, 1H), 4.00 (q, J=15.5 Hz, 2H), 2.07 (s, 3H), 2.05 (s, 3H), 1.99 (s, 3H), 1.71 (s, 3H).

Synthetical Route of Example 7 to Example 15 is Shown as Follows

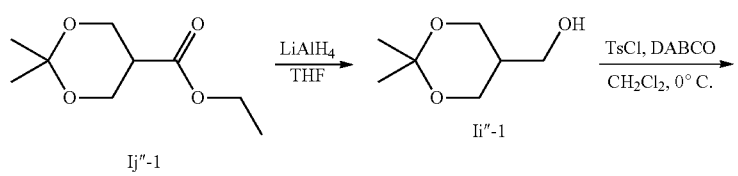

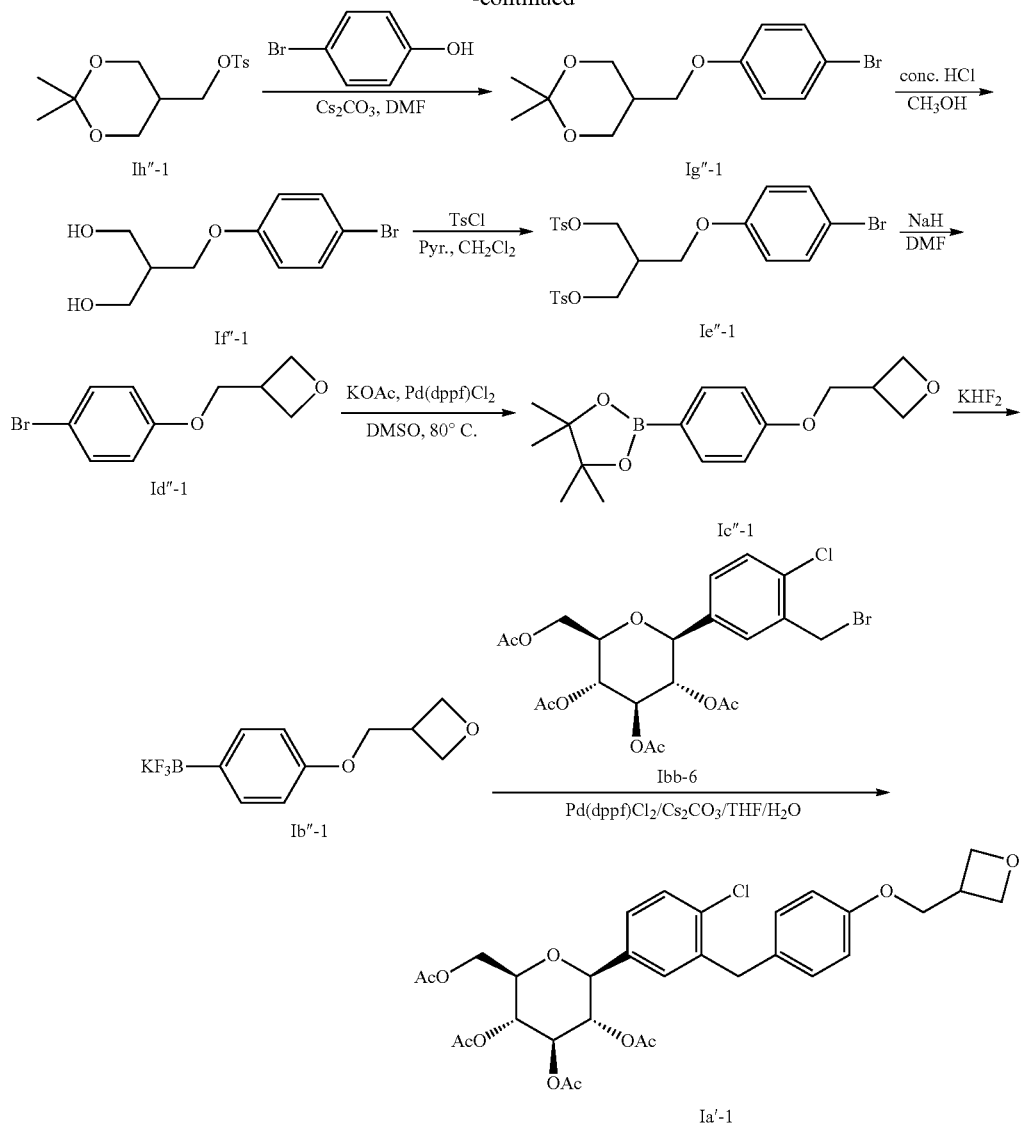

Example 7

Preparation of Compound Ii″-1

Under nitrogen, to a solution of LiAlH$_4$ (1.39 g, 36.58 mmol) in THF (40 mL) which was cooled to 0° C., compound Ij″-1 (5.29 g, 28.0 mmol) (according to the synthesis procedure in the patent WO 2008/0021032) was added dropwise. The mixture was stirred for 20 minutes at 0° C. and 2 hours at room temperature. When the reaction finished, the mixture was diluted with Et$_2$O (30 mL). With an ice bath, H$_2$O (0.14 mL) was added dropwise to the mixture, followed with NaOH solution (15%, 0.14 mL) and H$_2$O (0.42 mL) in sequence. After the mixture was stirred for 20 minutes at room temperature, appropriate amount of MgSO$_4$ was added to it and then another 20 minutes for stirring proceeded. After filtration, the filtrate was concentrated under vacuum to afford compound Ii″-1 (3.1 g, 75.2%).

$^1$HNMR (500 MHz, CDCl$_3$) δ: 3.93-3.96 (m, 2H), 3.65-3.72 (m, 4H), 1.73-1.79 (m, 1H), 1.35 (d, J=25.0 HZ, 6H).

Example 8

Preparation of Compound Ih″-1

To a dried 50 mL round bottom flask were added compound Ii″-1 (470 mg, 3.22 mmol), DABCO (721.9 mg, 6.43 mmol) and CH$_2$Cl$_2$ (15 mL). With an ice bath, TsCl (675.3 mg, 3.54 mmol) was added slowly to the solution. After the solution was stirred for 15 minutes, TLC showed the disappearance of the raw materials. The mixture was diluted with CH$_2$Cl$_2$ (20 mL) when the reaction finished, and after filtration, the filtrate was washed in turn with hydrochloric acid (1 N, 15 mL), saturated aqueous sodium bicarbonate (15 mL) and saturated brine (15 mL). The organic phase was dried over anhydrous sodium sulfate, the solvent was evaporated under vacuum to give compound Ih″-1 (665 mg, 68.8%).

LC-MS (ESI): m/z=301 [M+H]$^+$, 323 [M+Na]$^+$.

Example 9

Preparation of Compound Ig"-1

To a dried 25 mL round bottom flask were added compound Ih"-1 (500 mg, 1.67 mmol), p-bromophenol (286.7 mg, 1.67 mmol), $Cs_2CO_3$ (1.09 g, 3.33 mmol) and DMF (5.0 mL). After stirred for 3 hours at 80° C., the mixture was diluted with ethyl acetate (50 mL) and then washed with saturated brine (30 mL×3). The organic phase was dried over anhydrous sodium sulfate and concentrated, the residue was purified by preparative TLC (eluent: petroleum ether:ethyl acetate=10:1) to afford compound Ig"-1 (360 mg, 72%).

$^1$HNMR (500 MHz, $CDCl_3$) δ: 7.28-7.30 (m, 2H), 6.71-6.73 (m, 2H), 3.97-4.04 (m, 4H), 3.78-3.81 (m, 2H), 2.01-2.03 (m, 1H), 1.37 (d, J=25 HZ, 6H).

Example 10

Preparation of Compound If"-1

To a solution of compound Ig"-1 (320 mg, 1.07 mmol) in methanol (3.0 mL) was added dropwise concentrated hydrochloric acid (0.36 mL, 4.28 mmol), the mixture was stirred for 30 minutes at room temperature. The reaction was queched with saturated aqueous sodium bicarbonate (20.0 mL), the aqueous phase was extracted with ethyl acetate (30 mL×2). The organic phases were combined, dried over anhydrous sodium sulfate and concentrated to afford compound If"-1 (250 mg, 90.2%).

LC-MS (ESI): m/z=261 $[M+H]^+$, 283 $[M+Na]^+$.

Example 11

Preparation of Compound Ie"-1

To a dried 50 mL round bottom flask were added compound If"-1 (250 mg, 0.96 mmol), pyridine (304.3 mg, 3.85 mmol), DMAP (11.7 mg, 0.096 mmol) and THF (3.0 mL). With an ice bath, TsCl (238.3 mg, 1.25 mmol) was added slowly to the solution and then the solution was stirred for 15 minutes. When TLC showed the disappearance of the raw materials, water (20 mL) was added and the mixture was neutralized with hydrochloric acid (3.0 mL). The aqueous phase was extracted with ethyl acetate (30 mL×2) and the organic phases were combined, dried over anhydrous sodium sulfate and concentrated, the residue was purified by preparative TLC (eluent: petroleum ether:ethyl acetate=3:2) to afford compound Ie"-1 (120 mg, 30.2%).

LC-MS (ESI): m/z=417 $[M+H]^+$, 437 $[M+Na]^+$.

Example 12

Preparation of Compound Id"-1

With an ice bath, sodium hydride (0.225 g, 6.38 mmol) was added slowly to a solution of compound Ie"-1 (1.32 g, 3.19 mmol) in DMF (30 mL). The reaction was allowed to warm gradually to room temperature and stirred overnight. Water (20 mL) was added to quench the reaction. The mixture was diluted with ethyl acetate (60 mL). The organic phase was washed with saturated brine (30 mL×2), dried over anhydrous sodium sulfate and concentrated. The residue was purified by preparative TLC (eluent: petroleum ether:ethyl acetate=4:1) to afford compound Id"-1 (250 mg, 32.4%)

LC-MS (ESI): m/z=245 $[M+H]^+$..

Example 13

Preparation of Compound Ic"-1

Under nitrogen, to a dried 25 mL round bottom flask were added compound Id"-1 (156 mg, 0.64 mmol), potassium acetate (190 mg, 1.94 mmol), $Pd(dppf)Cl_2$ (47.2 mg, 0.064 mmol), bis(pinacolato)diboron (196.4 mg, 0.774 mmol) and DMSO (6.0 mL) and the mixture was stirred at 80° C. overnight. After dilution with ethyl acetate (50.0 mL), the organic phase was washed with saturated brine (25.0 mL×3), dried over anhydrous sodium sulfate and concentrated. The residue was purified by preparative TLC (eluent: petroleum ether: ethyl acetate=2:1) to afford compound Ic"-1 (46 mg, 24.7%).

LC-MS (ESI): m/z=291 $[M+H]^+$.

$^1$HNMR (500 MHz, $CDCl_3$) δ: 7.68 (d, J=8.5 HZ, 2H), 6.83-6.86 (m, 2H), 4.79-4.83 (m, 2H), 4.49-4.51 (m, 2H), 4.12-4.16 (m, 2H), 3.35-3.38 (m, 1H), 1.26 (s, 12H).

Example 14

Preparation of Compound Ib"-1

At room temperature, to a solution of compound Ic"-1 (40 mg, 0.138 mmol) in methanol (1 mL) was added a solution of $KHF_2$ (21.6 mg, 0.277 mmol) in water (0.3 mL). After stirred for 2 hours, the mixture was concentrated in vacuum. The residue was washed twice with diethyl ether and followed twice with dichloromethane. The residue was extracted twice with acetone. The organic phases were combined and evaporated to afford compound Ib"-1, which was used directly for the next step.

HRMS(ESI): calcd for $C_{10}H_{11}BF_3O_2$, 231.0801, found 231.0796.

Example 15

Preparation of Compound Ia'-1

Under nitrogen, to a flask were added compound Ib"-1 (0.138 mmol), compound Ibb-6 (according to the synthesis procedure in the patent WO 2008/034859) (96.8 mg, 0.184 mmol), $Cs_2CO_3$ (179 mg, 0.552 mmol), $Pd(dppf)Cl_2$ (6.8 mg, 0.0092 mmol) and the mixed solvent of $THF/H_2O$ (10/1, 3 mL). The oil bath was warmed to 70° C. and the reaction mixture was stirred overnight. After dilution with ethyl acetate, the mixture was washed with water and saturated brine, dried over anhydrous sodium sulfate. After filtration, the filtrate was evaporated, the residue was purified by preparative TLC (eluent: petroleum ether/ethyl acetate, 1:1) to afford compound Ia'-1 (20 mg, 23.5%).

LC-MS (ESI): m/z=641 $[M+Na]^+$.

Example 16

2-Oxetanylmethyl-4-methylbezenesulfonate

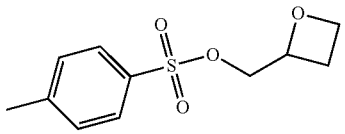 [SMILES: Cc1ccc(S(=O)(=O)OCC2CCO2)cc1]

At 0° C., to a solution of 2-oxetanyl methanol (212 mg, 2.41 mmol, commercially available) in $CH_2Cl_2$ (10 mL) was added DABCO (0.54 g, 4.82 mmol) and TsCl (528 mg, 2.77 mmol) was then added dropwise, the mixture was stirred for 10 minutes. After filtration, the filter cake was washed with $CH_2Cl_2$ and the filtrate was washed twice with water. The organic phase was dried over anhydrous sodium sulphate. The solvent was evaporated under vacuum to afford the residue (410 mg), which was used for the next step without further purification.

Example 17

3-Methyl-3-oxetanylmethyl-4-methylbenzene-sulfonate

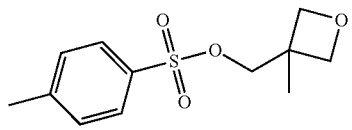 [SMILES: Cc1ccc(S(=O)(=O)OCC2(C)COC2)cc1]

At 0° C., to a solution of 3-methyl-3-oxetanyl methanol (507 mg, 4.97 mmol, commercially available) in $CH_2Cl_2$ (15 mL) was added DABCO (1.12 g, 9.94 mmol) and TsCl (1.09 g, 5.72 mmol) was then added dropwise, the mixture was stirred for 15 minutes. After filtration, the filter cake was washed with $CH_2Cl_2$ and the filtrate was washed twice with water. The organic phase was dries over anhydrous sodium sulphate. The solvent was evaporated under vacuum to afford the residue (1.05 g), which was used for the next step without further purification.

Example 18

2-(3-Oxetanyl)ethyl-4-methylbenzenesulfonate

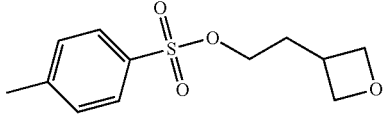 [SMILES: Cc1ccc(S(=O)(=O)OCCC2COC2)cc1]

At 0° C., to a solution of 2-(3-oxetanyl)ethanol (according to the synthesis procedure in the reference: *Journal of American Chemical Society,* 2009, 131, 2786-2787.) (193 mg, 1.89 mmol) in $CH_2Cl_2$ (15 mL) was added DABCO (847 mg, 7.56 mmol) and TsCl (1.43 g, 7.56 mmol) was then added dropwise, the mixture was stirred for 15 minutes. After filtration, the filter cake was washed with $CH_2Cl_2$ and the filtrate was washed twice with water. The organic phase was dries over anhydrous sodium sulphate. The solvent was evaporated under vacuum. The residue was purified by silica gel column chromatography (petroleum ether/ethyl acetate, 5:1) to afford the target compound.

Yield: 269 mg (56% of theoretical value).

LC-MS (ESI): m/z=257 $[M+H]^+$.

Synthetical Route of Example 19 to Example 23 is Shown as Follows

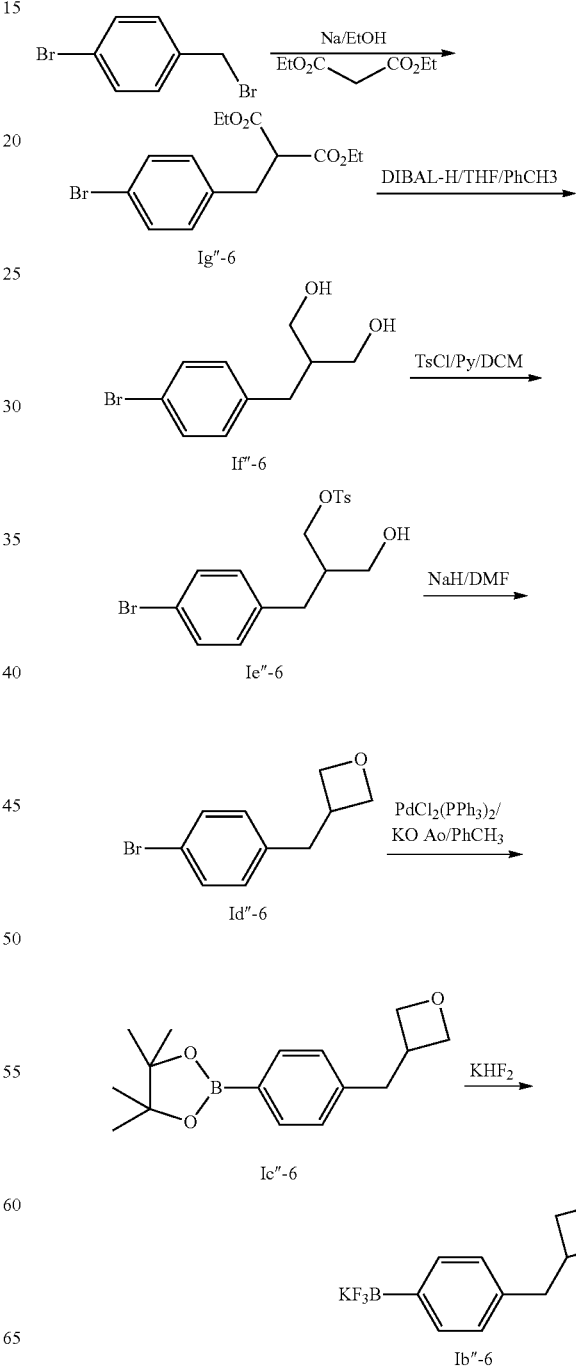

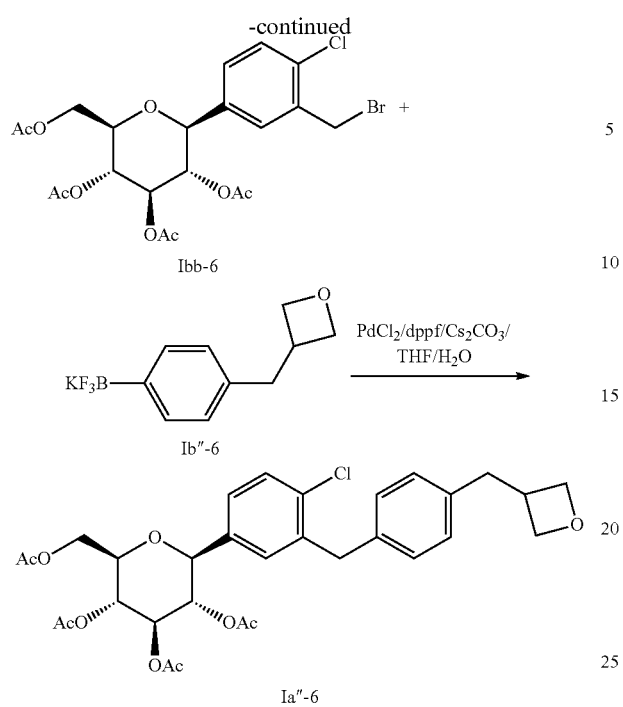

Example 19

Preparation of Compound Ie"-6

At room temperature, to a solution of compound If"-6 (according to the synthesis procedure in the reference: *J Med. Chem.*, 2005, 48 (19), 5980-5988.) (2 g, 8.16 mmol, 1.0 equiv) in CH$_2$Cl$_2$ (34 mL) were added pyridine (1.98 mL, 24.5 mmol, 3.0 equiv) and TsCl (1.71 g, 8.98 mmol, 1.1 equiv), the mixture was stirred overnight. The solvent was evaporated under vacuum. The residue was purified by silica gel column chromatography (eluent: petroleum ether:ethyl acetate=4:1 to 2:1) to afford compound Ie"-6 (2.3 g, 70%).

LC-MS (ESI): m/z=421 [M+Na]$^+$.

Example 20

Preparation of Compound Id"-6

With an ice bath, to a suspension of NaH (0.55 g, 13.7 mmol, 3.0 equiv) in DMF (24 mL) was added a solution of compound Ie"-6 (1.82 g, 4.57 mmol, 1.0 equiv) in DMF (3 mL). The mixture was then stirred for 1.5 hours at room temperature. After addition of ice water, the mixture was concentrated under vacuum and extracted with ethyl acetate. The combined organic phases were washed with water and saturated brine and dried over anhydrous sodium sulfate. After filteration, the solvent was evaporated under vacuum. The residue was purified by silica gel column chromatography (eluent: petroleum ether:ethyl acetate=4:1 to 2:1) to afford compound Id"-6 (0.61 g, 59%).

$^1$H-NMR (500 MHz, CDCl$_3$) δ: 7.40 (2H, d, J=8.0 Hz), 7.00 (2H, d, J=8.5 Hz), 4.78 (2H, dd, J=6.0, 7.5), 4.44 (2H, t, J=6.0 Hz), 3.18-3.31 (1H, m), 2.97 (2H, d, J=8.0 Hz).

Example 21

Preparation of Compound Ic"-6

Under nitrogen, to a flask were added compound Id"-6 (0.3 g, 1.32 mmol, 1.0 equiv), KOAc (0.26 g, 2.64 mmol, 2.0 equiv), bis(pinacolato)diboron (0.37 g, 1.45 mmol, 1.1 equiv), PdCl$_2$ (PPh$_3$)$_2$ (115 mg, 0.16 mmol, 0.12 equiv) and toluene (14 mL). The oil bath was gradually heated to 110° C. and the mixture was stirred overnight. After cooled to room temperature, the mixture was diluted with ethyl acetate. The organic phase was washed with water and saturated brine, dried over anhydrous sodium sulfate. After filteration, the solvent was evaporated under vacuum to afford compound Ic"-6 (631 mg), which was used directly for the next step.

LC-MS (ESI): m/z=275 [M+H]$^+$.

Example 22

Preparation of Compound Ib"-6

At room temperature, to a solution of compound Ic"-6 (631 mg, 2.3 mmol, 1.0 equiv) in methanol (3 mL) was added a solution of KHF$_2$ (0.36 g, 4.6 mmol, 2.0 equiv) in water (0.85 mL). After stirred for 2 hours, the mixture was concentrated under vacuum. The residue was washed twice with diethyl ether and followed by twice with dichloromethane. The residue was extracted twice with acetone, the organic phases were combined and concentrated to afford compound Ib"-6 (146 mg, 43% for two steps), which was used directly for the next step.

HRMS(ESI): calcd for C$_{10}$H$_{11}$BF$_3$O, 215.0852. found 215.0856.

Example 23

Preparation of Compound Ia'-6

Under nitrogen, to a flask were added compound Ib"-6 (146 mg, 0.57 mmol, 1.0 equiv), Ibb-6 (according to the synthesis procedure in the patent: WO2008/034859) (0.4 g, 0.76 mmol, 1.3 equiv), Cs$_2$CO$_3$ (0.74 g, 2.28 mmol, 4.0 equiv), Pd(dppf)Cl$_2$ (28 mg, 0.038 mmol, 0.07 equiv) and the mixed solvent of THF/H$_2$O (10/1, 8 mL). The oil bath was warmed to 80° C. and the reaction mixture was stirred overnight. After dilution with ethyl acetate, the mixture was washed with water and saturated brine, dried over anhydrous sodium sulfate. After filtration, the filtrate was evaporated, the residue was purified twice by preparative TLC (the eluent for the first time: petroleum ether/ethyl acetate, 2:1 and the eluent for the second time: petroleum ether/acetone 2:1) to afford compound Ia'-6 (100 mg, 29%).

LC-MS (ESI): m/z=603/605 (Cl) [M+H]$^+$.

Synthetical Route of Example 24 to Example 27 is Shown as Follows

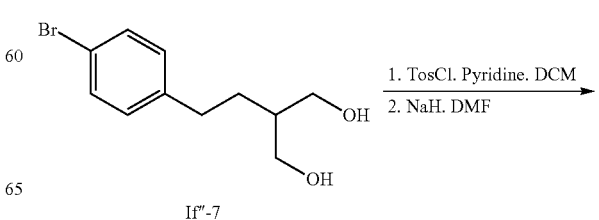

-continued

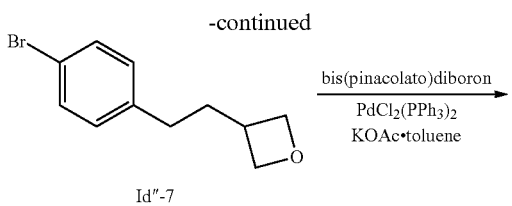

Id''-7

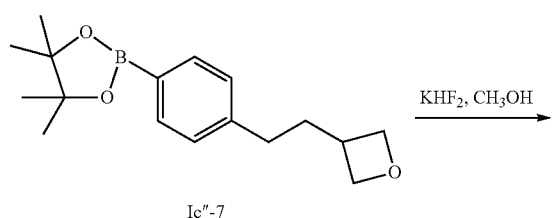

Ic''-7

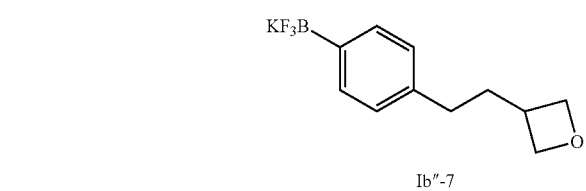

Ib''-7

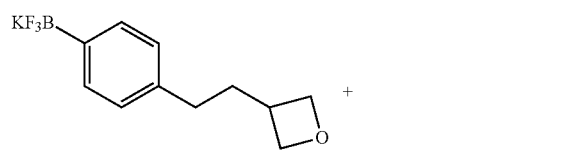

Ib''-7

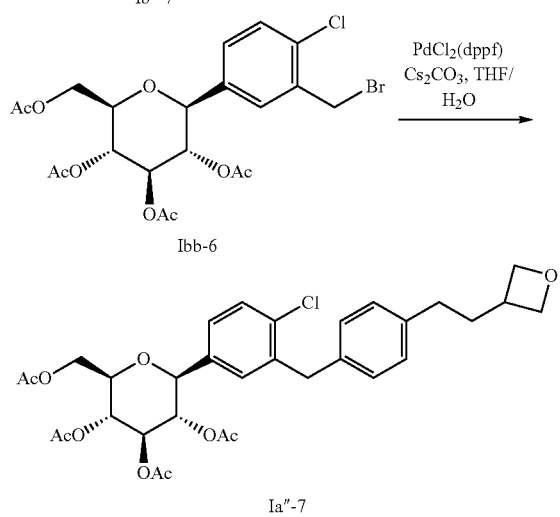

Ibb-6

Ia''-7

Example 24

Preparation of Compound Id''-7

At room temperature, to a solution of compound If''-7 (according to the synthesis procedure in the reference: *J. Org. Chem.* 1994, 59, 7038-7045.) (2.50 g, 9.69 mmol) in $CH_2Cl_2$ (30 mL) were added TsCl (2.02 g, 10.66 mmol) and pyridine (2.3 g, 29.07 mmol), the mixture was stirred for 8 hours. The reaction mixture was concentrated under vacuum. The residue was dissolved in DMF (5 mL). With an ice water bath, NaH (0.32 g, 8.00 mmol) was added to the solution and then the mixture was stirred for 1.5 hours at room temperature. Ice water was added to quench the reaction. The mixture was concentrated under vacuum and extracted with ethyl acetate. The organic phases were combined, washed with water and saturated brine, dried over anhydrous sodium sulfate. After filteration, the solvent was evaporated under vacuum. The residue was purified by silica gel column chromatography (eluent: petroleum ether:ethyl acetate=4:1) to afford compound Id''-7 (0.26 g, 11%).

LC-MS (ESI): m/z=242 $[M+H]^+$.

Example 25

Preparation of Compound Ic''-7

Under nitrogen, to a flask were added compound Id''-7 (0.26 g, 1.08 mmol), KOAc (0.45 g, 3.25 mmol), bis(pinacolato)diboron (0.33 g, 1.30 mmol), $PdCl_2 (PPh_3)_2$ (38 mg, 0.05 mmol) and toluene (10 mL). The oil bath was gradually heated to 110° C., the mixture was stirred overnight. After cooled to room temperature, the mixture was diluted with ethyl acetate. The organic phase was washed with water and saturated brine, dried over anhydrous sodium sulfate. After filteration, the solvent was evaporated under vacuum to afford compound Ic''-7, which was used directly for the next step.

LC-MS (ESI): m/z=289 $[M+H]^+$.

Example 26

Preparation of Compound Ib''-7

At room temperature, to a solution of compound Ic''-7 in methanol (3 mL) was added a solution of $KHF_2$ (85 mg, 1.08 mmol) in water (0.5 mL). After stirred for 2 hours, the mixture was concentrated under vacuum. The residue was washed twice with diethyl ether and followed by twice with dichloromethane. The residue was extracted twice with acetone, the organic phases were combined and evaporated to afford compound Ib''-7 (crude 0.18 g), which was used directly for the next step.

HRMS(ESI): calcd for $C_{11}H_{13}BF_3O$, 229.1008. found 229.1011.

Example 27

Preparation of Compound Ia'-7

Under nitrogen, to a flask were added crude compound Ib''-7, compound Ibb-6 (0.36 g, 0.67 mmol), $Cs_2CO_3$ (0.65 g, 2.01 mmol), Pd(dppf)$Cl_2$ (24 mg, 0.03 mmol) and the mixed solvent of THF/$H_2O$ (10/1, 8 mL). Refluxing at 77° C., the reaction mixture was stirred overnight. After cooling to room temperature, the mixture was filtrated through celite. The filtrate was evaporated under vacuum. The residue was purified by preparative TLC (petroleum ether:ethyl acetate=2:1) to afford compound Ia'-7 (crude 0.17 g).

LC-MS (ESI): m/z=617/619 (Cl) $[M+H]^+$.

Example 28 tert-Butyl 3-(tosyloxymethyl)azetidine-1-carboxylate

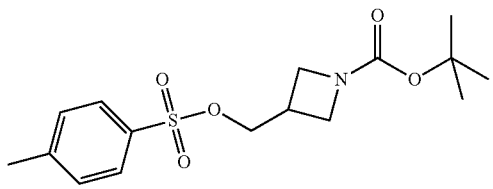 [SMILES: Cc1ccc(S(=O)(=O)OCC2CN(C(=O)OC(C)(C)C)C2)cc1]

At 0° C., to a stirred solution of tent-butyl 3-(hydroxymethyl)azetidine-1-carboxylate (250 mg, 1.34 mmol, commercially available) in $CH_2Cl_2$ (10 mL) was added DABCO (300.7 mg, 2.68 mmol) and TsCl (293.6 mg, 1.54 mmol) was then added dropwise. The mixture was stirred for 15 minutes at 0° C., and then filterted, washed with $CH_2Cl_2$. The filtrate was washed twice with water and dried over anhydrous sodium sulfate. The solvent was evaporated under vacuum. The residue was used for the next step without further purification.

Yield: 363 mg (79.6% of theoretical value).

LC-MS (ESI): m/z=364 [M+Na]$^+$.

Example 29

Preparation of Compound Ia'-9

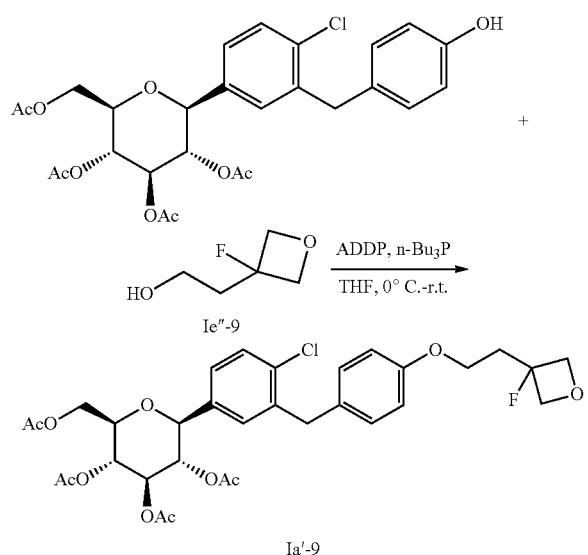

To a round bottom flask were added compound Ie''-9 (according to the synthesis procedure in the reference: *J. Am. Chem. Soc.* 2009, 131, 2786-2787.) (60 mg, 0.109 mmol), 1-chloro-4-(2,3,4,6-tetra-O-acetyl-β-D-glucopyranose-1-yl)-2-(4-hydroxy-benzyl)benzene (52 mg, 0.436 mmol), ADDP (165 mg, 0.654 mmol) and THF (6 mL). With an ice water bath, tri-n-butyl phosphine (0.16 mL, 0.654 mmol) was added. The mixture was allowed to warm to room temperature and stirred overnight. After starting materials disappeared (monitored by TLC), the mixture was concentrated. The residue was purified by silica gel column chromatography (eluent: petroleum ether:ethyl acetate=4:1) to afford compound Ia'-9 (42 mg, 59%).

LC-MS (ESI): m/z=673 [M+Na]$^+$.

Synthetical Route of Example 30 to Example 33 is Shown as Follows

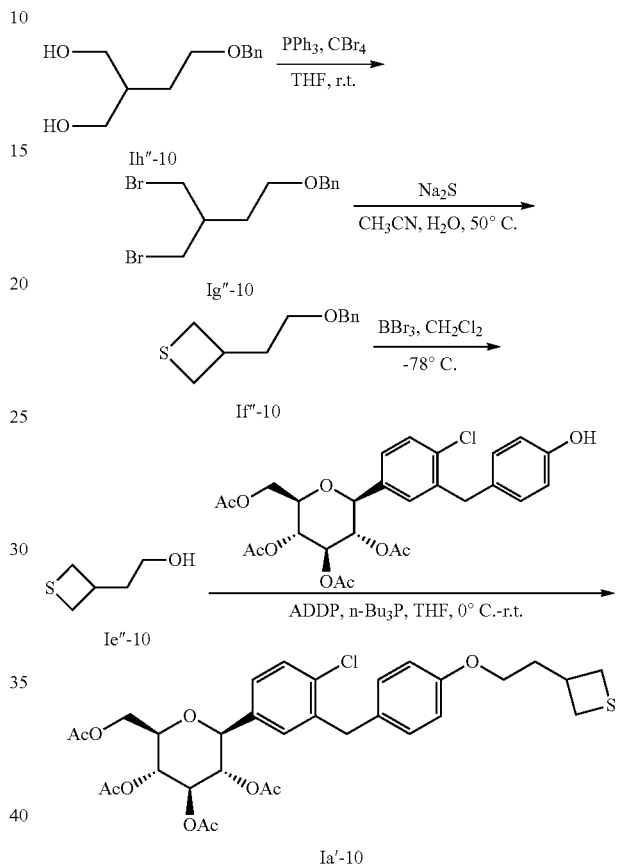

Example 30

Preparation of Compound Ig''-10

To a dried round bottom flask were added $PPh_3$ (8.32 g, 31.4 mmol), $CBr_4$ (10.3 g, 31.4 mmol) and THF (100 mL) and after the solution was stirred for 5 minutes, compound Ih''-10 (according to the synthesis procedure in the reference: *J. Am. Chem. Soc.* 2009, 131, 2786-2787.) (2.20 g, 10.46 mmol) was added. Two hours later, starting materials disappeared (monitored by TLC), the mixture was then filterted through celite. The filtrate was concentrated, the residue was purified by silica gel column chromatography (eluent: petroleum ether: diethyl ether=100:1) to afford compound Ig''-10 (1.7 g, 70%).

$^1$H-NMR (500 MHz, $CDCl_3$) δ: 7.28-7.22 (m, 5H), 4.43 (s, 2H), 3.56 (dd, J=3.6, 10.0 Hz, 2H), 3.46 (t, J=5.9 Hz, 2H), 3.41 (dd, J=6.7, 10.4 Hz, 2H), 2.00-2.15 (m, 1H), 1.70 (q, J=6.5 Hz, 2H).

Example 31

Preparation of Compound If''-10

To a flask were added compound Ig''-10 (500 mg, 1.50 mmol), $Na_2S$ (234 mg, 3.0 mmol), acetonitrile (15 mL) and water (2 mL), and then the mixture was stirred for 2 hours at 50° C. When starting materials disappeared (monitored by TLC), the solvent was evaporated under vacuum. The residue was purified by silica gel column chromatography (eluent: petroleum ether:diethyl ether=100:1) to afford compound If''-10 (283 mg, 91%).

MS(ESI) m/z=209 [M+H]$^+$.

$^1$H-NMR (500 MHz, CDCl$_3$) δ: 7.36-7.28 (m, 5H), 4.46 (s, 2H), 3.50-3.44 (m, 1H), 3.41 (t, J=6.0 Hz, 2H), 3.15 (t, J=9.0 Hz, 2H), 3.06 (t, J=8.0 Hz, 2H), 1.86 (q, J=6.0 Hz, 2H).

Example 32

Preparation of Compound Ie''-10

At −78° C., to a solution of compound If''-10 (374 mg, 1.80 mmol) in CH$_2$Cl$_2$ (15 mL) was added BBr$_3$ (4 N, 0.54 mL, 2.16 mmol), and the mixture was stirred for 15 minutes under this condition. When starting materials disappeared (monitored by TLC), saturated aqueous NaHCO$_3$ (10 mL) was added to quench the reaction. The mixture was then extracted with CH$_2$Cl$_2$ (20 mL×3), the organic phase was dried over anhydrous sodium sulfate. The solvent was evaporated under vacuum to afford crude compound Ie''-10, which was used directly for the next step.

Example 33

Preparation of Compound Ia'-10

To a flask were added crude compound Ie''-10, which was obtained from the last step, 1-chloro-4-(2,3,4,6-tetra-O-acetyl-β-D-glucopyranose-1-yl)-2-(4-hydroxy-benzyl)benzene (200 mg, 0.36 mmol), ADDP (544 mg, 2.16 mmol) and THF (30 mL). With an ice water bath, tri-n-butyl phosphine (0.48 mL, 2.16 mmol) was added and the mixture was stirred overnight at room temperature. After starting materials disappeared (monitored by TLC), solvent was evaporated under vacuum. The residue was purified by silica gel column chromatography (eluent: petroleum ether:ethyl acetate=4:1) to afford compound Ia'-10 (112 mg, 48%).

LC-MS (ESI): m/z=671 [M+Na]$^+$.

Example 34

Preparation of Compound Id''-12

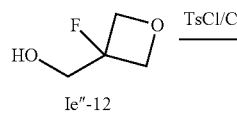
Ie''-12

TsCl/CH$_2$Cl$_2$/DABCO

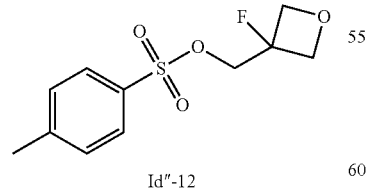
Id''-12

A solution of compound Ie''-12 (according to the synthesis procedure in the reference: US2005/0215599) (159 mg, 1.5 mmol) in CH$_2$Cl$_2$ (15 mL) was cooled to 0° C. After DABCO (672 mg, 6.0 mmol) was added, TsCl (1.135 g, 6.0 mmol) was added dropwise. And then the mixture was stirred for 15 minutes. After filtration, the filter cake was washed with CH$_2$Cl$_2$. The filtrate was washed twice with water and dried over anhydrous sodium sulfate. The solvent was evaporated under vacuum. The residue was purified by silica gel column chromatography (petroleum ether/ethyl acetate, 6:1) to afford compound Id''-12 (203 mg, 52%).

LC-MS (ESI): m/z=261 [M+H]$^+$.

Synthetical Route of Example 35 to Example 41 is Shown as Follows

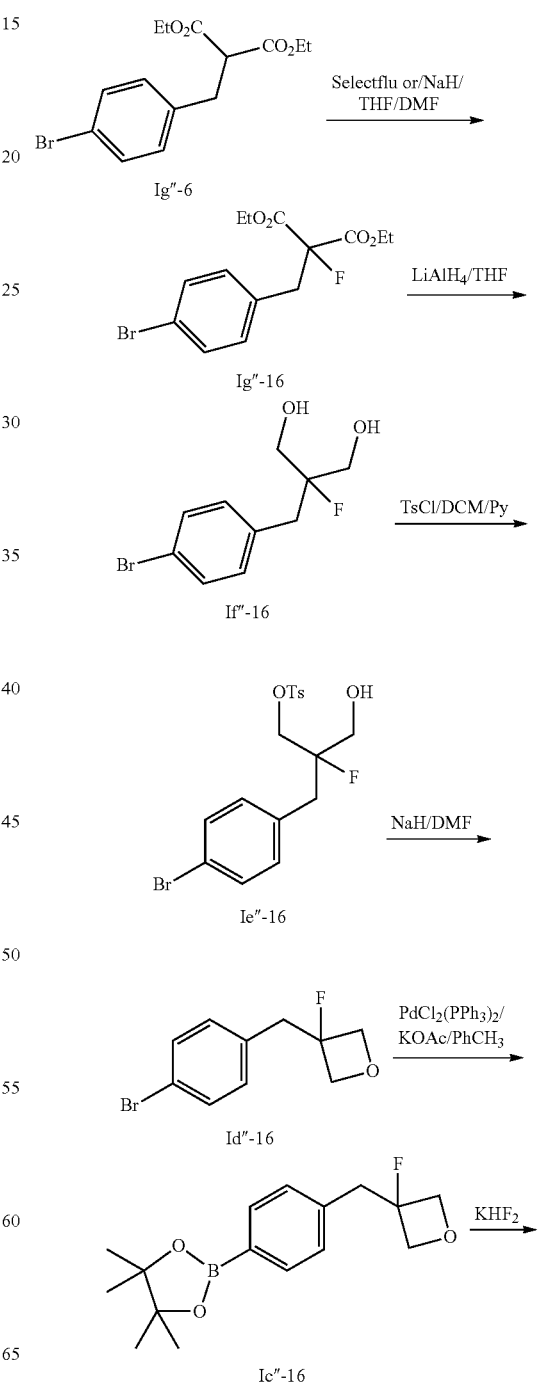

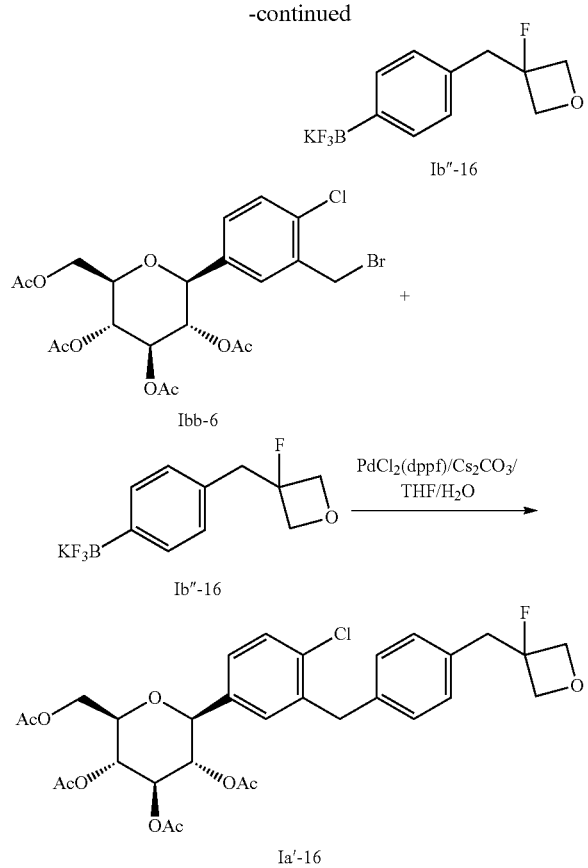

Example 35

Preparation of Compound Ig"-16

At room temperature, to a suspension of NaH (146 mg, 3.65 mmol) in THF (5 mL) was added compound 2 (according to the synthesis procedure in the references: *J. Org. Chem.*, 1984, 49 (22), 4226-4237; *Tetrahedron Asymm.*, 2001, 12 (4), 585-596.) (1.0 g, 3.04 mmol). The mixture was stirred for 1.5 hours at 70° C. After cooling to room temperature, the mixture was diluted with THF (16 mL) and DMF (16 mL). After cooling again with an ice water bath, Selectfluor® (1.18 g, 3.34 mmol) was added. The mixture was stirred at room temperature overnight. Water was added to quench the reaction. After extraction with diethyl ether, the organic phase was washed with water and saturated brine, dried over anhydrous sodium sulfate. After filteration, the filtrate was evaporated to give compound Ig"-16 (1.07 g, 100%).

LC-MS (ESI): m/z=347 [M+H]$^+$.
$^1$H-NMR (500 MHz, CDCl$_3$) δ: 7.41 (2H, d, J=8.0 Hz), 7.12 (2H, d, J=8.0 Hz), 4.24 (4H, q, J=7.0 Hz), 3.42 (2H, d, J=25.0 Hz), 1.25 (6H, t, J=7.0 Hz) ppm.

Example 36

Preparation of Compound If"-16

With an ice water bath, to a suspension of LiAlH$_4$ (0.13 g, 3.42 mmol) in THF (6 mL) was added a solution of compound Ig"-16 (0.59 g, 1.71 mmol) in THF (5 mL) slowly. The mixture was stirred for 2 hours at 30° C. After cooling with ice water, NaSO$_4$.10 H$_2$O was added slowly and followed by diethyl ether. The mixture was on standing for a while, filtered through celite. The filter cake was washed with ethyl acetate. The organic phases were combined, and dried over anhydrous sodium sulfate. After filteration, the solvent was evaporated to give compound If"-16 (0.386 g, 86%), which was used directly for the next step.

LC-MS (ESI): m/z=285 [M+Na]$^+$.

Example 37

Preparation of Compound Ie"-16

At room temperature, to a solution of compound If"-16 (0.385 g, 1.47 mmol) in CH$_2$Cl$_2$ (8 mL) were added pyridine (0.36 mL, 4.41 mmol) and TsCl (0.31 g, 1.61 mmol). After stirred overnight at room temperature, the mixture was diluted with ethyl acetate, washed in turn with water, hydrochloric acid (1 N), water and saturated brine. The organic phase was dried over anhydrous sodium sulfate. After filteration, the solvent was evaporated under vacuum. The residue was purified by silica gel column chromatography (eluent: petroleum ether:ethyl acetate=4:1) to afford compound Ie"-16 (0.26 g, 43%).

LC-MS (ESI): m/z=439 [M+Na]$^+$.

Example 38

Preparation of Compound Id"-16

With an ice water bath, to a suspension of NaH (72 mg, 1.8 mmol) in DMF (1.5 mL) was added a solution of compound Ie"-16 (0.25 g, 0.6 mmol) in DMF (1.5 mL). The mixture was stirred for 1.5 hours at room temperature. Then the mixture was diluted with ethyl acetate, washed with water and saturated brine. The organic phase was dried over anhydrous sodium sulfate. After filteration, the solvent was evaporated under vacuum. The residue was purified by silica gel column chromatography (eluent: petroleum ether:ethyl acetate=2:1) to afford compound Id"-16 (54 mg, 37%).

LC-MS (ESI): m/z=246 [M+H]$^+$.
$^1$H-NMR (500 MHz, CDCl$_3$) δ: 7.45 (2H, d, J=8.5 Hz), 7.13 (2H, d, J=8.5 Hz), 4.74 (2H, dd, J=8.5, 19.5 Hz), 4.55 (2H, t, J=8.5, 19.0 Hz), 3.21 (2H, d, J=25.0 Hz).

Example 39

Preparation of Compound Ic"-16

Under nitrogen, to a flask were added compound Id"-16 (52 mg, 0.21 mmol), KOAc (42 mg, 0.42 mmol), bis(pinacolato)diboron (60 mg, 0.23 mmol), PdCl$_2$ (PPh$_3$)$_2$ (5 mg, 0.007 mmol) and toluene (3 mL). The oil bath was gradually heated to 110° C., and the mixture was stirred overnight. After cooled to room temperature, the mixture was diluted with ethyl acetate. The organic phase was washed with water and saturated brine, dried over anhydrous sodium sulfate. After filteration, the solvent was evaporated under vacuum to afford compound Ic"-16 (99 mg), which was used directly for the next step.

LC-MS (ESI): m/z=293 [M+H]$^+$.

Example 40

Preparation of Compound Ib"-16

At room temperature, to the solution of compound Ic"-16 (98 mg, 0.33 mmol) in methanol (2.5 ml) was added a solution of KHF$_2$ (52 mg, 0.67 mmol) in water (0.15 ml). The mixture was stirred at r.t. for 2 hours, and then concentrated under vacuum. The residue was washed with CH$_2$Cl$_2$ twice followed by extraction with acetone twice. The solvent was evaporated and the residue of compound Ib"-16 (62 mg) was used for the next step directly.

HRMS(ESI): calcd for C$_{10}$H$_{10}$BF$_4$O, 233.0758. found 233.0755.

Example 41

Preparation of Compound Ia'-16

To a flask were added compound Ib"-16 (62 mg, 0.228 mmol), compound Ibb-6 (100 mg, 0.187 mmol), cesium carbonate (0.295 g, 2.28 mmol), PdCl$_2$ (dppf) (20 mg, 0.027 mmol), the mixed solvent of THF/water (3 ml, 10:1). The mixture was stirred overnight under nitrogen while the oil bath was warm to 80° C. The mixture was diluted with ethyl acetate, washed with water and saturated brine, dryed over anhydrous Na$_2$SO$_4$. After filteration, the solvent was evaporated under vacuum, the residue was purified by preparative TLC (eluent: petroleum ether/ethyl acetate, 2:1) to afford compound Ia'-16 (12 mg, 9% for 3 steps). LC-MS (ESI): m/z=643 [M+Na]$^+$.

Example 42

Preparation of Compound 1

To a solution of compound Ia'-1 (20 mg, 0.032 mmol) in methanol (2.0 ml) and water (0.4 mL) was added LiOH.H$_2$O (5.4 mg, 0.13 mmol). The mixture was stirred overnight at room temperature. The mixture was filtered and concentrated. The residue was purified by HPLC to afford compound 1 (5 mg, 34.3%).

$^1$HNMR (500 MHz, MeOD) δ: 7.22-7.25 (m, 2H), 7.17-7.19 (m, 1H), 7.02 (d, J=8.5 HZ, 2H), 6.74-6.76 (m, 2H), 4.74-4.78 (m, 2H), 4.48 (t, J=6.5 HZ, 2H), 4.06 (d, J=6.5 HZ, 2H), 3.90-4.00 (m, 3H), 3.76-3.78 (m, 1H), 3.57-3.60 (m, 1H), 3.25-3.35 (m, 4H), 3.17-3.18 (m, 1H).

LC-MS (ESI): m/z=451 [M+H]$^+$, 473 [M+Na]$^+$.

Example 43

Preparation of Compounds 2, 3 and 4

The mixture of 1-chloro-4-(β-D-glucopyranose-1yl)-2-(4-hydroxy benzyl)benzene (80 mg, 0.21 mmol), 4-methylbenzenesulfonate 2-oxetane methyl ester (65.3 mg, 0.27 mmol) and Cs$_2$CO$_3$ (171 mg, 0.52 mmol) in 3 mL of DMF was heated to 80° C. and stirred for 2 hours. The mixture was cooled down to room temperature, and filtered. The solvent was evaporated, and the residue was purified by silica gel column chromatography (AcOEt/MeOH, 10:1) to afford compound 2. Compound 2 was then resolved via preparative HPLC [chiral column, CHIRALCEL® OJ-H, mobile phase: n-Hexane:EtOH (0.1% NH(C$_2$H$_5$OH)$_2$)=7:3; speed: 1 mL/1 min. Temp: 40° C. injection volume: 10 μL] to provide isomer 3 (retention time: 12.84 min) which has a shorter retention time and isomer 4 (retention time: 20.35 min).

Compound 2:

Yield: 60 mg (63.2% of theoretical value).

$^1$HNMR (500 MHz, CD$_3$OD) δ: 7.28-7.37 (m, 3H), 7.14 (d, J=9 HZ, 2H), 6.89-6.91 (m, 2H), 5.12-5.17 (m, 1H), 4.63-4.75 (m, 2H), 4.01-4.16 (m, 5H), 3.88-3.90 (m, 1H), 3.69-3.72 (m, 1H), 3.37-3.48 (m, 4H), 2.67-2.82 (m, 2H).

LC-MS (ESI): m/z=473/475 (Cl) [M+Na]$^+$.

Compound 3:

$^1$HNMR (500 MHz, CD$_3$OD) δ: 7.34-7.37 (m, 2H), 7.28-7.30 (m, 1H), 7.14 (d, J=8.5 HZ, 2H), 6.89 (d, J=8.5 HZ, 2H), 5.14 (brs, 1H), 4.83-4.74 (m, 2H), 4.01-4.15 (m, 5H), 3.88-3.90 (m, 1H), 3.69-3.72 (m, 1H), 3.37-3.48 (m, 3H), 3.29-3.32 (m, 1H), 2.68-2.80 (m, 2H).

LC-MS (ESI): m/z=473/475 (Cl) [M+Na]$^+$.

Compound 4:

$^1$HNMR (500 MHz, CD$_3$OD) δ: 7.23-7.25 (m, 2H), 7.17-7.19 (m, 1H), 7.02 (d, J=8.5 HZ, 2H), 6.78 (d, J=8.5 HZ, 2H), 5.02 (brs, 1H), 4.51-4.61 (m, 2H), 3.89-4.04 (m, 5H), 3.76-3.78 (m, 1H), 3.57-3.60 (m, 1H), 3.28-3.36 (m, 3H), 3.17-3.21 (m, 1H), 2.58-2.66 (m, 2H).

LC-MS (ESI): m/z=473/475 (Cl) [M+Na]$^+$.

Example 44

Preparation of Compound 5

A mixture of 1-chloro-4-(β-D-glucopyranosyl-1-yl)-2-(4-hydroxybenzyl)-benzene (80 mg, 0.21 mmol), 3-methyl-3-oxetanyl butane methyl 4-methyl benzenesulfonate (69.1 mg, 0.27 mmol) and cesium carbonate (171 mg, 0.52 mmol) in 3 mL of dimethylformamide was heated to 80° C. and stirred for 2 hours. The mixture was cooled down to room temperature, and filtered. The solvent was evaporated, and the residue was purified by silica gel column chromatography (AcOEt/MeOH, 10:1) to afford compound 5 (58 mg, yield; 59.4%).

$^1$HNMR (500 MHz, CD$_3$OD) δ: 7.29-7.37 (m, 3H), 7.14 (d, J=8.5 HZ, 2H), 6.89 (d, J=6.5 HZ, 2H), 4.66 (d, J=6 HZ, 2H), 4.45 (d, J=6 HZ, 2H), 4.01-4.11 (m, 5H), 3.88-3.90 (q, 1H), 3.69-3.72 (q, 1H), 3.39-3.47 (m, 3H), 3.29-3.31 (m, 1H), 1.43 (s, 3H).

LC-MS (ESI): m/z=487/489 (Cl) [M+Na]$^+$.

Example 45

Preparation of Compound 6

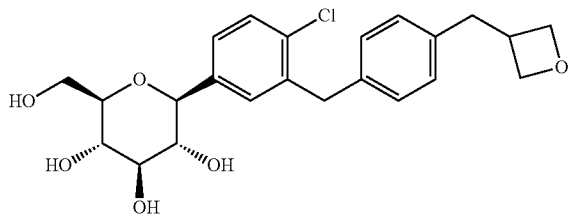 [SMILES: OC[C@H]1O[C@@H](c2ccc(Cl)c(Cc3ccc(CC4COC4)cc3)c2)[C@H](O)[C@@H](O)[C@@H]1O]

To a flask was added compound Ia'-6 (100 mg, 0.17 mmol), THF (5 mL), and H₂O (2.5 mL). To the mixture was added LiOH.H₂O (40 mg, 0.95 mmol, 5.6 equiv), and stirred for 2 hours at room temperature. The mixture was then diluted with AcOEt and washed with water and saturated brine, dried over anhydrous Na₂SO₄, filtrated. The solvent was evaporated. The residue was purified by preparative TLC (eluent: CH₂Cl₂/MeOH 10:1) to afford compound 6 (60 mg, yield; 83%).

¹HNMR (500 MHz, CD₃OD) δ: 7.31-7.38 (2H, m), 7.28 (1H, dd, J=2.0, 8.5 Hz), 7.12 (2H, d, J=8.0 Hz), 7.06 (2H, d, J=8.0 Hz), 4.75 (2H, dd, J=6.0, 8.0 Hz), 4.45 (2H, t, J=6.0 Hz), 3.99-4.11 (3H, m), 3.82-3.91 (1H, m), 3.69 (1H, dd, J=5.0, 12.0 Hz), 3.45 (1H, t, J=8.0 Hz), 3.35-3.43 (2H, m), 3.23-3.29 (2H, m), 2.95 (2H, d, J=7.5 Hz).

LC-MS (ESI): m/z=435 [M+H]⁺, 457 [M+Na]⁺.

Example 46

Preparation of Compound 7

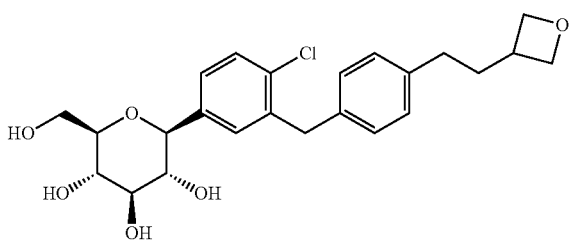 [SMILES: OC[C@H]1O[C@@H](c2ccc(Cl)c(Cc3ccc(CCC4COC4)cc3)c2)[C@H](O)[C@@H](O)[C@@H]1O]

To a flask was added compound Ia'-7 (170 mg, 0.276 mmol), THF (5 mL), and H₂O (1 mL). To the mixture was added LiOH.H₂O (65 mg, 1.54 mmol), and stirred for 1 hour at room temperature. The mixture was then diluted with AcOEt and washed with water and saturated brine, dried over anhydrous Na₂SO₄, filtrated. The solvent was evaporated. The residue was purified by preparative TLC (eluent: CH₂Cl₂/MeOH 10:1) to afford compound 7 (12 mg).

¹HNMR (500 MHz, CD₃OD) δ: 7.20-7.26 (m, 3H), 7.01 (d, J=8.0 Hz, 2H), 6.97 (d, J=8.0 Hz, 2H), 4.60 (t, J=7.0 Hz, 2H), 4.19 (t, J=6.0 Hz, 2H), 3.92-4.01 (m, 3H), 3.77 (d, J=12.0 Hz, 1H), 3.58 (dd, J=5.0, 12.0 Hz, 1H), 3.34 (dd, J=8.5 Hz, 17.5 Hz, 1H), 3.16-3.29 (m, 3H), 2.87-2.92 (m, 1H), 2.43 (t, J=7.5 Hz, 2H), 1.87 (q, J=7.5 Hz, 2H).

LC-MS (ESI): m/z=471 [M+Na]⁺.

Example 47

Preparation of Compound 8

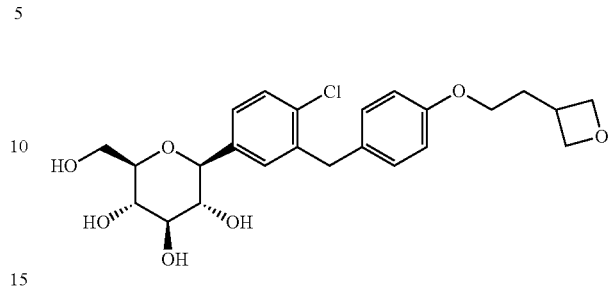

The mixture of 1-chloro-4-(β-D-glucopyranosyl-1-yl)-2-(4-hydroxybenzyl)-benzene (80 mg, 0.21 mmol), 2-(3-oxetane)ethyl 4-methylbenzene sulfonate (75 mg, 0.29 mmol) and cesium carbonate (137 mg, 0.42 mmol) in 3 mL of dimethylformamide was heated to 80° C. for 2 hours, and cooled down to room temperature, filtered. The solvent was evaporated and the residue was purified by silical gel chromatography (AcOEt/MeOH 20:1) to afford compound 8 (51 mg, yield; 52%).

¹HNMR (500 MHz, CD₃OD) δ: 7.37-7.28 (m, 3H), 7.11 (d, J=9.0 Hz, 2H), 6.79 (d, J=8.5 Hz, 2H), 4.84 (dd, 1=8 Hz, 6 Hz, 2H), 4.53 (t, J=6.0 Hz, 2H), 4.11-3.88 (m, 6H), 3.72-3.69 (m, 1H), 3.48-3.22 (m, 5H), 2.17-2.13 (m, 2H).

LC-MS (ESI): m/z=465/467 (Cl) [M+H]⁺.

Example 48

Preparation of Compound 9

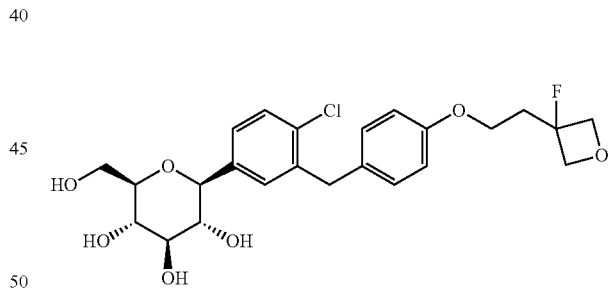

To a flask were added Ia'-9 (21 mg, 0.032 mmol), LiOH.H₂O (10 mg, 0.256 mmol), THF (3 mL), MeOH (1 mL) and H₂O (1 mL). The mixture was stirred for 2 hours at r.t. When starting materials disappeared (monitored by TLC), the solvent was evaporated. The residue was purified by silica gel chromatography (eluent: AcOEt:MeOH=20:1) to afford compound 9 (9 mg yield; 58%).

¹H-NMR (500 MHz, CD₃OD) δ: 7.35-7.26 (m, 3H), 7.10 (d, J=8.5 Hz, 2H), 6.80 (d, J=9.0 Hz, 2H), 4.81-4.71 (m, 4H), 4.12-3.98 (m, 5H), 3.85-3.88 (m, 1H), 3.68 (dd, J=5.5 Hz, 12.5 Hz, 2H), 3.46-3.38 (m, 3H), 2.38 (dt, J=6.1 Hz, 21.4 Hz, 2H).

LC-MS (ESI): m/z=505/507 (Cl) [M+Na]⁺.

Example 49

Preparation of Compound 10

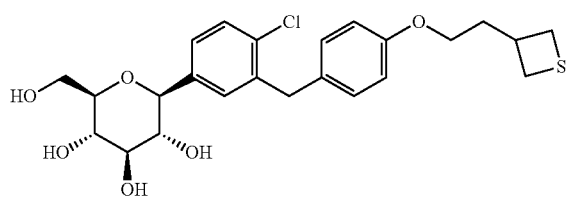 [SMILES: OC[C@H]1O[C@@H](c2ccc(Cl)c(Cc3ccc(OCCC4CSC4)cc3)c2)[C@H](O)[C@@H](O)[C@@H]1O]

To a solution of compound Ia'-10 (31 mg, 0.048 mmol) in the mixed solvent of THF (3 mL) and MeOH (1 mL) was added the solution of LiOH.H₂O (0.48 mmol) in water (1 mL). The mixture was stirred for 2 hours at r.t. When starting materials disappeared (monitored by TLC), the solvent was evaporated. The residue was purified by silica gel chromatography (eluent: AcOEt:MeOH=20:1) to afford compound 10 (21 mg, yield; 91%).

$^1$H-NMR (500 MHz, CD$_3$OD) δ: 7.34-7.26 (m, 3H), 7.08 (d, J=8.6 Hz, 2H), 6.77 (d, J=8.8 Hz, 2H), 4.10-3.97 (m, 3H), 3.88-3.86 (m, 3H), 3.68 (dd, J=5.4, 11.9 Hz, 1H), 3.53-3.26 (m, 5H), 3.15 (t, J=8.7 Hz, 2H), 3.10 (t, J=7.9 Hz, 2H), 1.97 (q, J=7.2 Hz, 2H).

LC-MS (ESI): m/z=503 [M+Na]$^+$.

Example 50

Preparation of Compound 11

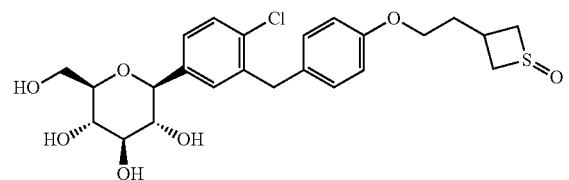 [SMILES: O=S1CC(CCOc2ccc(Cc3cc([C@@H]4O[C@H](CO)[C@@H](O)[C@H](O)[C@H]4O)ccc3Cl)cc2)C1]

To a solution of compound 10 (22 mg, 0.046 mmol) in AcOH (1 mL) was added H$_2$O$_2$ (30% in water, 6 μL, 0.055 mmol). The mixture was stirred for 30 minutes at room temperature. When starting materials disappeared (monitored by TLC), the solvent was evaporated. The residue was purified by silica gel chromatography (eluent: AcOEt:MeOH=15:1) to afford compound 11 (16 mg, 70%).

$^1$H-NMR (500 MHz, CD$_3$OD) δ: 7.34-7.26 (m, 3H), 7.10 (d, J=9.0 Hz, 2H), 6.81 (d, J=8.5 Hz, 2H), 4.26-4.21 (m, 2H), 4.26-4.21 (m, 2H), 4.10-3.98 (m, 6H), 3.94-3.83 (m, 3H), 3.68 (dd, J=5.2, 11.9 Hz, 1H), 3.46-3.26 (m, 4H), 2.15-2.12 (m, 2H).

LC-MS (ESI): m/z=535 [M+K]$^+$.

Example 51

Preparation of Compound 12

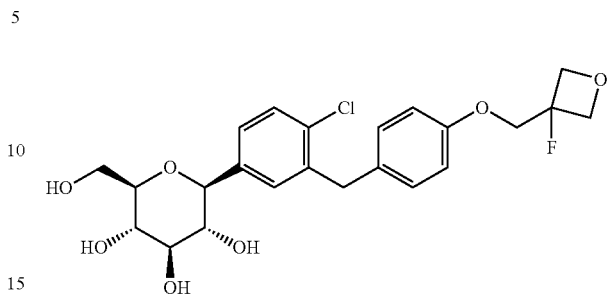

The mixture of 1-chloro-4-(β-D-glucopyranosyl-1-yl)-2-(4-hydroxybenzyl)-benzene (122 mg, 0.32 mmol), compound Id''-12 (83 mg, 0.32 mmol) and cesium carbonate (209 mg, 0.64 mmol) in 5 mL of dimethylformamide was heated to 50° C. and stirred for 4 hours. The reaction mixture was cooled down to room temperature, filtered. The solvent was evaporated and the residue was purified by silical gel chromatography (AcOEt:MeOH=20:1) to afford compound 12 (69 mg, 46%).

$^1$H-NMR (500 MHz, CD$_3$OD) δ: 7.30-7.37 (2H, m), 7.28 (1H, dd, J=2.0, 8.0 Hz), 7.14 (2H, d, J=8.5 Hz), 6.89 (2H, d, J=8.5 Hz), 4.78 (2H, dd, J=8.5, 28.0 Hz), 4.74 (2H, dd, J=8.5, 27.5 Hz), 4.32 (2H, d, J=20.0 Hz), 4.09 (1H, d, J=9.5 Hz), 4.07 (1H, d, J=15.0 Hz), 4.02 (1H, d, J=15.0 Hz), 3.87 (1H, dd, J=2.0, 12.0 Hz), 3.69 (1H, dd, J=5.5, 12.0 Hz), 3.45 (1H, t, J=8.5 Hz), 3.34-3.42 (2H, m), 3.24-3.29 (1H, m).

LC-MS (ESI): m/z=491 [M+Na]$^+$.

Example 52

Preparation of Compound 13

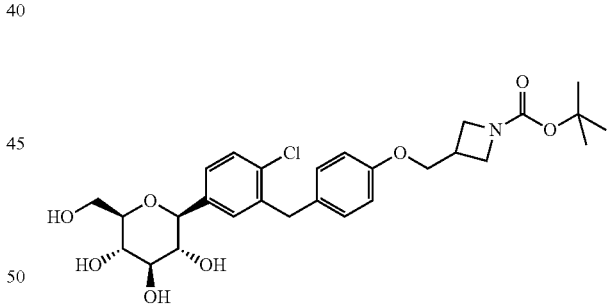

The mixture of 1-chloro-4-(β-D-glucopyranosyl-1-yl)-2-(4-hydroxybenzyl)-benzene (256.6 mg, 0.75 mmol), 4-methylbenzenesulfonate 1-carboxylic t-butyl-azetidine-3-methyl ester (220 mg, 0.58 mmol) and cesium carbonate (470 mg, 1.45 mmol) in 3 mL of dimethylformamide was heated to 80° C. for 2 hours, and cooled down to room temperature, filtered. The solvent was evaporated and the residue was purified by silical gel chromatography (10:1 CH$_2$Cl$_2$/MeOH).

Yield: 170 mg (53.5% of theoretical value).

$^1$H NMR (500 MHz, CD$_3$OD) δ: 7.28-7.37 (m, 3H), 7.13 (d, J=7.5 HZ, 2H), 6.86 (d, J=7.5 HZ, 2H), 4.04-4.11 (m, 7H), 3.89 (d, J=12 HZ, 2H), 3.80 (s, 2H), 3.71-3.72 (m, 1H), 3.40-3.47 (m, 3H), 3.28-3.32 (m, 2H), 1.46 (s, 9H).

LC-MS (ESI): m/z=572/574 (Cl) [M+Na]$^+$.

Example 53

Preparation of Compound 14

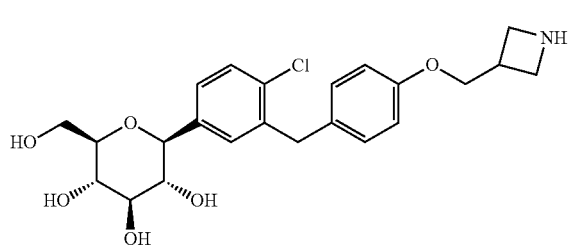 [SMILES: OC[C@H]1O[C@@H](c2ccc(Cl)c(Cc3ccc(OCC4CNC4)cc3)c2)[C@H](O)[C@@H](O)[C@@H]1O]

To a solution of compound 13 (150 mg, 0.27 mmol) in MeOH (4 mL) was added concentrated HCl (36%, 0.6 ml) dropwise, and stirred at r.t. for 1.5 hours. The solvent was evaporated and the residue was purified by HPLC to provide the target compound.

Yield: 80 mg (65.3% of theoretical value).

$^1$HNMR (500 MHz, CD$_3$OD) δ: 7.29-7.37 (m, 3H), 7.16 (d, J=8.5 HZ, 2H), 6.94 (d, J=10.0 HZ, 2H), 4.23 (t, J=10.0, 2H), 4.02-4.13 (m, 7H), 3.88-3.90 (m, 1H), 3.39-3.72 (m, 1H), 3.40-3.47 (m, 3H), 3.46 (s, 2H).

LC-MS (ESI): m/z=450/452 (Cl) [M+H]$^+$.

Example 54

Preparation of Compound 15

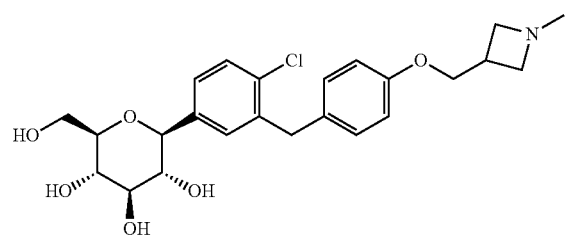 [SMILES: CN1CC(COc2ccc(Cc3cc([C@@H]4O[C@H](CO)[C@@H](O)[C@H](O)[C@H]4O)ccc3Cl)cc2)C1]

The mixture of compound 14 (10 mg, 0.022 mmol) in EtOH (3 mL), paraformaldehyde (1.32 mg, 0.44 mmol) and acetic acid (0.02 mL) was stirred at r.t., NaBH$_3$CN (2.8 mg, 0.044 mmol) was slowly added, and then the resulting mixture was stirred overnight. The mixture was filtered and the solvent was evaporated. The residue was purified by HPLC to provide the target compound.

Yield: 5 mg (48% of theoretical value).

$^1$HNMR (500 MHz, CD$_3$OD) δ: 7.28-7.37 (m, 3H), 7.12 (d, J=8.5 HZ, 2H), 6.83-6.86 (m, 2H), 4.00-4.11 (m, 5H), 3.87-3.90 (m, 1H), 3.69-3.72 (m, 1H), 3.38-3.50 (m, 5H), 3.32-3.33 (m, 1H), 3.18 (t, J=7.5, 2H), 2.84-2.92 (m, 1H), 2.36 (s, 3H).

LC-MS (ESI): m/z=464 [M+H]$^+$.

Example 55

Preparation of Compound 16

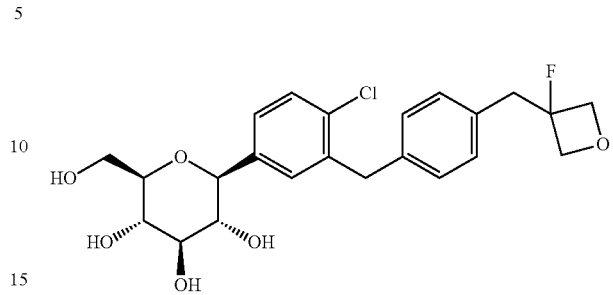

To a mixture of compound Ia'-16 (11 mg, 0.018 mmol), H$_2$O (1 mL) in THF (2 mL) was added LiOH.H$_2$O (6 mg, 0.143 mmol), and then the mixture was stirred at 25° C. for one hour. The reaction mixture was diluted with AcOEt, washed by water and saturated brine, dried over anhydrous Na$_2$SO$_4$. After filteration, the solvent was evaporated under vacuum, the residue was purified by HPLC to afford compound 16 (4 mg, 50%).

$^1$H-NMR (500 MHz, CD$_3$OD) δ: 7.33-7.38 (2H, m), 7.29 (1H, dd, J=2.0, 8.5 Hz), 7.18 (2H, d, J=8.5 Hz), 7.15 (2H, d, J=8.0 Hz), 4.64 (4H, d, J=20.0 Hz), 4.04-4.12 (3H, m), 3.84-3.90 (1H, m), 3.69 (1H, dd, J=5.0, 12.0 Hz), 3.45 (1H, t, J=8.5 Hz), 3.36-3.43 (2H, m), 3.25-3.30 (1H, m), 3.20 (2H, d, J=24.5 Hz).

LC-MS (ESI): m/z=475 [M+Na]$^+$.

Example 56

Preparation of Compound 17

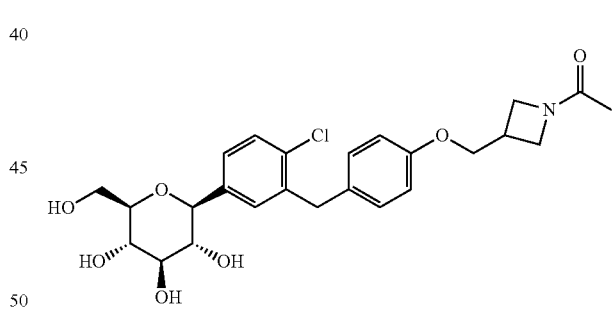

The solution of compound 14 (20 mg, 0.0445 mmol), Ac$_2$O (45.4 mg, 0.445 mmol), 4-dimethylaminopyridine (0.54 mg, 0.00445 mmol), Et$_3$N (9.07 mg, 0.089 mmol) in CH$_2$Cl$_2$ (3 mL) was stirred overnight at room temperature. CH$_2$Cl$_2$ (8 mL) was added, and the organic phase was washed by saturated aqueous solution of NaHCO$_3$ twice, then dried over anhydrous Na$_2$SO$_4$. The solvent was evaporated and the residue was dissolved in THF (3 mL), and a solution of LiOH (19.15 mg, 0.455 mmol) in water (1 mL) was added slowly in drops. The mixture was stirred for half an hour at room temperature, filtered, and evaporated under vacuum. The residue was purified by HPLC to provide the target compound.

Yield: 10 mg (44.7% of theoretical value).

$^1$HNMR (500 MHz, CD$_3$OD) δ: 7.34-7.37 (2H, m), 7.28-7.30 (m, 1H), 7.13 (d, J=8.5 HZ, 2H), 6.86 (d, J=8.5 HZ, 2H), 4.34 (t, J=9.0 HZ, 1H), 4.01-4.12 (m, 7H), 3.84-3.90 (m, 2H), 3.69-3.72 (m, 1H), 3.40-3.49 (m, 3H), 3.29-3.33 (m, 2H), 3.06-3.07 (m, 1H), 1.88 (s, 3H).

LC-MS (ESI): m/z=492/494 (Cl) [M+H]+.

Example 57

Preparation of Compound 18

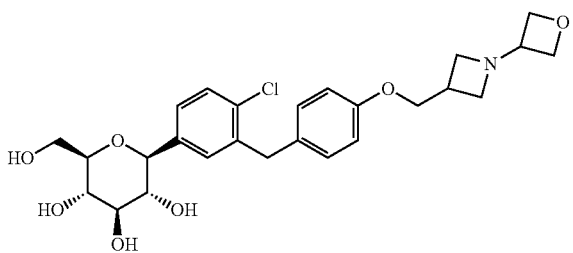 [SMILES: OC[C@H]1O[C@@H](c2ccc(Cl)c(Cc3ccc(OCC4CN(C5COC5)C4)cc3)c2)[C@H](O)[C@@H](O)[C@@H]1O]

To a solution of compound 14 (10 mg, 0.022 mmol), 3-Oxetanone (6.23 mg, 0.44 mmol) and AcOH (0.02 mL) in ethanol (3 mL) was added NaBH₃(CN) (2.8 mg, 0.044 mmol) slowly while stirring at room temperature, and then the resulting mixture was stirred overnight. The reaction mixture was filtered and the solvent was evaporated under vacuum. The residue was purified by HPLC to provide the target compound.

Yield: 5 mg (44.4% of theoretical value).

$^1$HNMR (500 MHz, CD$_3$OD) δ: 7.16-7.25 (m, 3H), 7.00 (d, J=9.0 HZ, 2H), 6.73 (d, J=9.0 HZ, 2H), 4.62 (t, J=6.5, 2H), 4.40-4.42 (m, 2H), 3.88-3.99 (m, 5H), 3.70-3.78 (m, 2H), 3.57-3.60 (m, 1H), 3.26-3.41 (m, 5H), 3.13-3.21 (m, 3H), 2.83-2.87 (m, 1H).

LC-MS (ESI): m/z=506 [M+H]+.

Example 58

Preparation of Compound 19

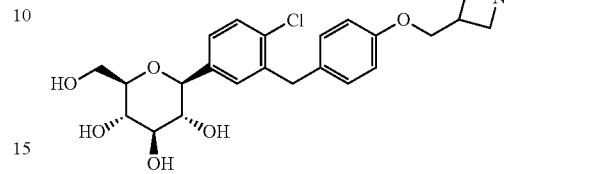

To a solution of compound 14 (20 mg, 0.0445 mmol) in DMSO (1 mL) were successively added 4-fluoro-bromobenzen (11.6 mg, 0.067 mmol), CuI (0.84 mg, 0.00445 mmol), L-Proline (1 mg, 0.0088 mmol) and K$_2$CO$_3$ (60.72 mg, 0.44 mmol). Then, the mixture was heated to 80° C. under nitrogen and stirred overnight. The mixture was cooled down to room temperature and filtered. The filtrate was purified by HPLC to provide the target compound.

Yield: 2 mg (16.5% of theoretical value).

$^1$HNMR (500 MHz, CD$_3$OD) δ: 7.34-7.37 (m, 2H), 7.28-7.30 (m, 1H), 7.12 (d, J=8.5 HZ, 2H), 6.94 (t, J=9.0 HZ, 2H), 6.86 (d, J=9.0 HZ, 2H), 6.47-6.50 (m, 2H), 4.17 (d, J=7.0 HZ, 2H), 3.96-4.11 (m, 5H), 3.87-3.90 (m, 1H), 3.69-3.72 (m, 3H), 3.40-3.46 (m, 3H), 3.28-3.30 (m, 1H), 3.11-3.15 (m, 1H).

LC-MS (ESI): m/z=544 [M+H]+.

Example 59

Synthetical Route of Compound 20

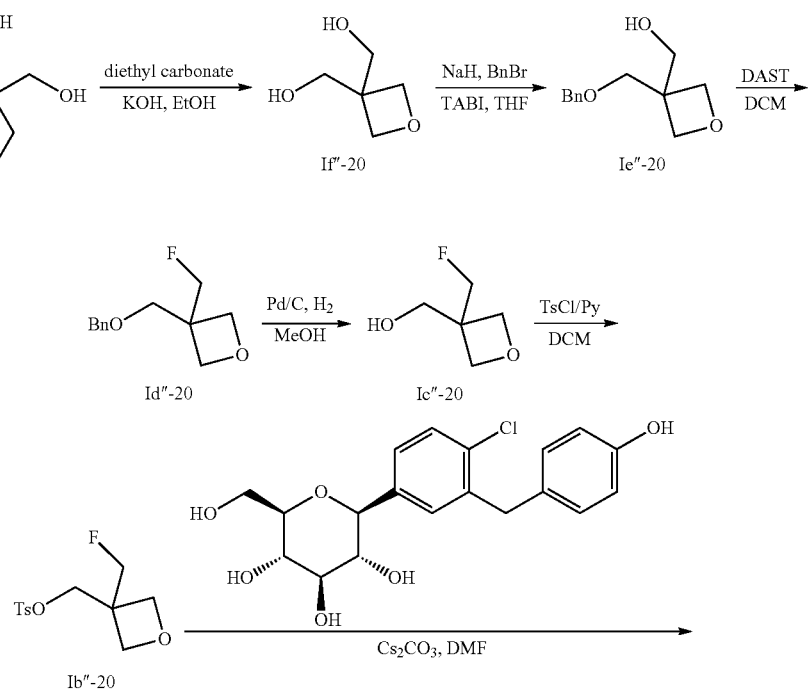

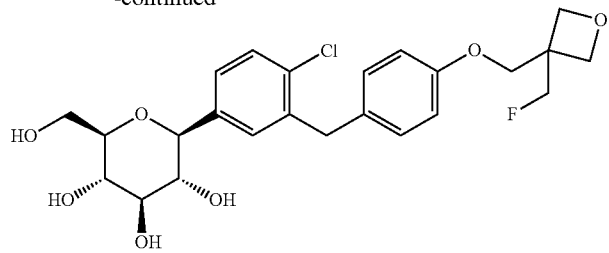

20

Preparation of Compound If"-20

To a 100 mL round bottom flask was added Pentaerythritol (25 g, 183.6 mmol), diethyl carbonate (27.7 mL), a catalytic amount of KOH (50 mg, 0.89 mmol) and ethanol (3 mL). The mixture was heated to 135° C. and stirred for 4 hours. Additional catalytic amount of KOH (50 mg, 0.89 mmol) was added to the reaction mixture. The ethanol was evaporated under atmosphere. The mixture was then slowly heated to 170° C. and maintained for one hour, then heated to 190° C. and maintained for one hour. When the reaction mixture became clear, the mixture was distilled under reduced pressure (0.5 mmHg, 190° C.) to afford compound If"-20 (13.1 g, 60.5%). $^1$H-NMR (500 MHz, d$_6$-DMSO) δ: 4.76 (t, J=5.5 Hz, 2H), 4.27 (s, 4H), 3.54 (d, J=5.0 Hz, 4H).

Preparation of Compound Ie"-20

The compound If"-20 (8 g, 67.7 mmol) was dissolved in THF (250 mL), cooled with an ice water bath, and then NaH (60%, 2.85 g, 71.1 mmol) was added under nitrogen. The mixture was stirred for 1 hour, and then tetra-butyl ammonium iodide (1.25 g, 3.39 mmol) was added followed by benzyl bromide slowly at 0° C. The reaction mixture was stirred overnight at room temperature, cooled down by an ice water bath. Water was slowly added, and the tetrahydrofuran was removed by distillation under reduced pressure. The residue was extracted by ethyl acetate. The organic phase was washed with water and saturated brine in sequence, dried over anhydrous sodium sulfate, and concentrated under vacuum. The residue was purified by column chromatography (petroleum ether/ethyl acetate=2:1 to 1:2) to afford compound Ie"-20 (3.2 g, 23%).

$^1$H-NMR (500 MHz, CDCl$_3$) δ: 7.28-7.41 (m, 5H), 4.56 (s, 2H), 4.49 (d, J=6.5 Hz, 2H), 4.43 (d, J=6.0 Hz, 2H), 3.92 (s, 2H), 3.79 (s, 2H), 2.44 (brs, 1H).

Preparation of Compound Id"-20

Compound Ie"-20 (1 g, 4.8 mmol) was dissolved in CH$_2$Cl$_2$ (10 mL). The solution was cooled to −70° C. with ethanol-dry ice under nitrogen, and DAST (0.8 mL, 6 mmol) was added dropwise slowly. The reaction solution was warmed to room temperature and stirred for 4 days. The reaction solution was diluted with methylene chloride, added a saturated aqueous sodium bicarbonate solution. The organic phase was separated and the aqueous phase was extracted with dichloromethane. The organic phases were combined, washed with water and brine in sequence, dried over anhydrous sodium sulfate, and purified by column chromatography (petroleum ether/ethyl acetate=5:1) to afford compound Id"-20 (0.8 g, 79%).

$^1$H-NMR (500 MHz, CDCl$_3$) δ: 7.27-7.40 (m, 5H), 4.67 (d, J=7.0 Hz, 2H), 4.57 (s, 2H), 4.53 (d, J=6.5 Hz, 2H), 4.50 (dd, J=2.0 Hz, 6.0 Hz, 2H), 3.72 (s, 2H).

Preparation of Compound Ic"-20

The compound Id"-20 (40 mg, 0.19 mmol) was dissolved in methanol (3 mL). To the solution was added Pd/C (10%). The mixture was stirred under hydrogen atmosphere at room temperature overnight. The mixture was filtered and concentrated to afford crude compound Ic"-20 which was used directly in the next step.

Preparation of Compound Ib"-20

The compound Ic"-20 (64 mg, 0.53 mmol) was dissolved in CH$_2$Cl$_2$ (3 mL). To the solution was added pyridine (51 mg, 0.64 mmol) and p-toluenesulfonyl chloride (113 mg, 0.59 mmol). The mixture was stirred at room temperature overnight, diluted with CH$_2$Cl$_2$, washed with water and saturated brine successively, dried over anhydrous Na$_2$SO$_4$, concentrated. The residue was purified by preparative HPLC (petroleum ether/ethyl acetate=2:1) to afford compound Ib"-20 (25 mg, 17%).

$^1$H-NMR (500 MHz, CDCl$_3$) δ: 7.73 (d, J=8.0 Hz, 2H), 7.31 (d, J=8.0 Hz, 2H), 4.54 (d, J=46.5 Hz, 2H), 4.39 (d, J=6.5 Hz, 2H), 4.33 (dd, J=2.5 Hz, 6.5 Hz, 2H), 4.20 (s, 2H), 2.40 (s, 3H).

Preparation of Compound 20

The mixture of 1-chloro-4-(β-D-glucopyranosyl-1-yl)-2-(4-hydroxybenzyl)-benzene (35 mg, 0.091 mmol), compound Ib"-20 (25 mg, 0.091 mmol) and cesium carbonate (36 mg, 0.11 mmol) in dimethylformamide (2.5 mL) was heated to 60° C. and stirred overnight. The reaction mixture was cooled down to room temperature, filtered. The solvent was evaporated and the residue was purified by HPLC-MS to afford compound 20 (25 mg, 57%).

$^1$H-NMR (500 MHz, CD$_3$OD) δ: 7.31-7.34 (m, 2H), 7.27 (dd, J=2.0 Hz, 8.5 Hz, 1H), 7.12 (d, J=8.5 Hz, 2H), 6.87 (d, J=8.5 Hz, 2H), 4.75 (s, 1H), 4.66 (s, 1H), 4.57-4.61 (m, 4H), 4.16 (s, 2H), 3.98-4.08 (m, 3H), 3.87 (dd, J=1.5 Hz, 12.0 Hz, 1H), 3.69 (dd, J=5.0 Hz, 12.0 Hz, 1H), 3.37-3.46 (m, 2H), 3.26-3.30 (m, 2H). LC-MS (ESI): m/z=505 [M+Na]$^+$.

Example 60

Synthetical Route of Compound 21

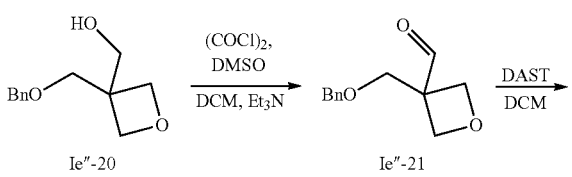

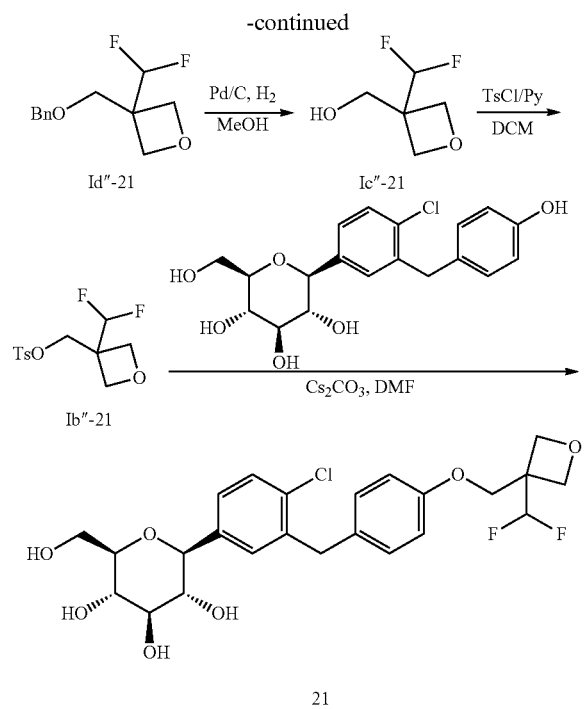

Preparation of Compound Ie"-21

The mixture of oxalyl chloride (0.69 mL, 7.2 mmol) and dichloromethane (13 mL) was cooled to −78° C. To the mixture was added dropwise dimethyl sulfoxide (1.1 mL, 15.8 mmol), stirred for 15 minutes at −78° C. After a solution of compound Ie"-20 (1 g, 4.8 mmol) in dichloromethane (10 mL) was added, the mixture was stirred for another two hours at low temperature. Triethyl amine (3.4 mL, 24 mmol) was added slowly. After a 30-minutes stirring, the mixture was warmed to room temperature. Water was added to the mixture, the organic phase was separated and the aqueous phase was extracted with dichloromethane. The organic layers were combined and washed with water and saturated brine in sequence, dried over anhydrous sodium sulfate and concentrated to afford crude compound Ie"-21 which was used directly in the next reaction.

$^1$H-NMR (500 MHz, CDCl$_3$) δ: 9.89 (s, 1H), 7.26-7.40 (m, 5H), 4.82 (d, J=6.5 Hz, 2H), 4.57 (s, 2H), 4.55 (d, J=6.5 Hz, 2H), 3.94 (s, 2H).

Preparation of Compound Id"-21

Compound Ie"-21 (0.5 g, 2.42 mmol) was dissolved in CH$_2$Cl$_2$ (15 mL). Under nitrogen, cooled by an ice-water bath, to the solution was added DAST (1.3 mL, 9.84 mmol) slowly. The reaction solution was warmed to room temperature and stirred overnight. Saturated aqueous sodium bicarbonate was added to the mixture, the organic phase was separated and the aqueous phase was extracted by dichloromethane. The organic layers were combined and washed with water and saturated brine in sequence, dried over anhydrous sodium sulfate and concentrated. The residue was purified by preparative HPLC (petroleum ether/ethyl acetate=5:1) to afford compound Id"-21 (271 mg, 49%).

$^1$H-NMR (500 MHz, CDCl$_3$) δ: 7.28-7.41 (m, 5H), 6.04 (t, J=56.5 Hz, 1H), 4.74 (d, J=6.5 Hz, 2H), 4.57 (s, 2H), 4.44 (d, J=6.5 Hz, 2H), 3.81 (s, 2H).

(500 MHz, CDCl$_3$) δ: 7.28-7.38 (m, 5H), 4.79 (d, J=8.0 Hz, 1H), 4.75 (d, J=7.5 Hz, 1H), 4.55 (d, J=8.5 Hz, 1H), 4.51 (d, J=6.5 Hz, 1H), 4.52 (s, 2H), 3.52 (t, J=6.5 Hz, 2H), 2.01-2.09 (m, 2H), 1.70-1.76 (m, 2H).

Preparation of Compound Ic"-23

Compound Id"-23 (3.0 g, 13.39 mmol) was dissolved in methanol (60 mL). To the solution was added Pd/C (1.5 g). The mixture was stirred under hydrogen atmosphere (3 atm) at 30° C. for 16 h. When starting materials disappeared (monitored by TLC), the mixture was filtered and concentrated to afford crude compound Ic"-23 (1.58 g, 88%).

Preparation of Compound Ib"-23

Compound Ic"-23 (1.58 g, 11.8 mmol) was dissolved in CH$_2$Cl$_2$ (50 mL). To the solution was added DABCO (2.64 g, 23.6 mmol). With an ice-water bath, TsCl (3.14 g, 16.5 mmol) was added portionwise and then the mixture was stirred for one hour. When starting materials disappeared (monitored by TLC), the mixture was diluted with ethyl acetate, washed with water and brine successively. The organic phase was dried over anhydrous Na$_2$SO$_4$, filtered, concentrated to afford compound Ib"-23 (3.29 g, 97%). LC-MS (ESI): m/z=311 [M+Na]$^+$.

Preparation of Compound 23

The mixture of 1-chloro-4-(β-D-glucopyranosyl-1-yl)-2-(4-hydroxybenzyl)-benzene (2.90 g, 7.64 mmol), compound Ib"-23 (2.20 g, 7.64 mmol) and cesium carbonate (7.47 g, 22.92 mmol) in dimethylformamide (50 mL) was heated to 80° C. and stirred overnight. When starting materials were consumed (monitor by LC/MS), the solvent was evaporated under vacuum. The residue was dissolved in ethyl acetate. The organic phase was washed with water, dried over anhydrous sodium sulphate, filtered, concentrated. The residue was purified by preparative HPLC to afford compound 23 (1.5 g 40%).

$^1$H-NMR (500 MHz, CD$_3$OD) δ: 7.30-7.38 (m, 2H), 7.28 (dd, J=2.0 Hz, 8.0 Hz, 1H), 7.10 (d, J=8.5 Hz, 2H), 6.82 (d, J=8.5 Hz, 2H), 4.73 (dd, J=8.0 Hz, 20.0 Hz, 2H), 4.59 (dd, J=8.0 Hz, 20.0 Hz, 2H), 4.00-4.17 (m, 3H), 3.97 (t, J=6.5 Hz, 2H), 3.83-3.91 (m, 1H), 3.69 (dd, J=5.0 Hz, 10.5 Hz, 1H), 3.42-3.49 (m, 1H), 3.36-3.42 (m, 2H), 3.25-3.30 (m, 1H), 2.05-2.19 (m, 2H), 1.78-1.91 (m, 2H). LC-MS (ESI): m/z=519 [M+Na]$^+$.

Example 63

Synthetical Route of Compound 24

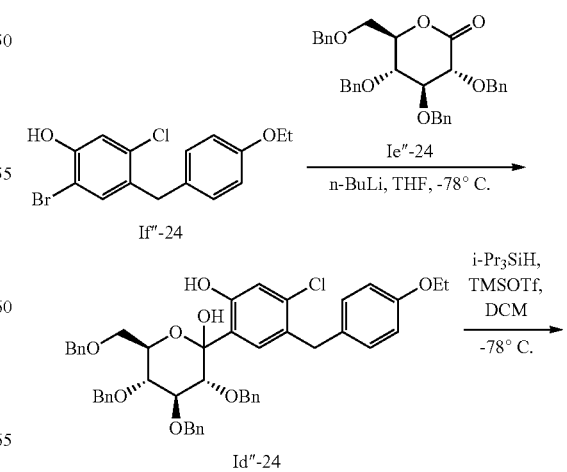

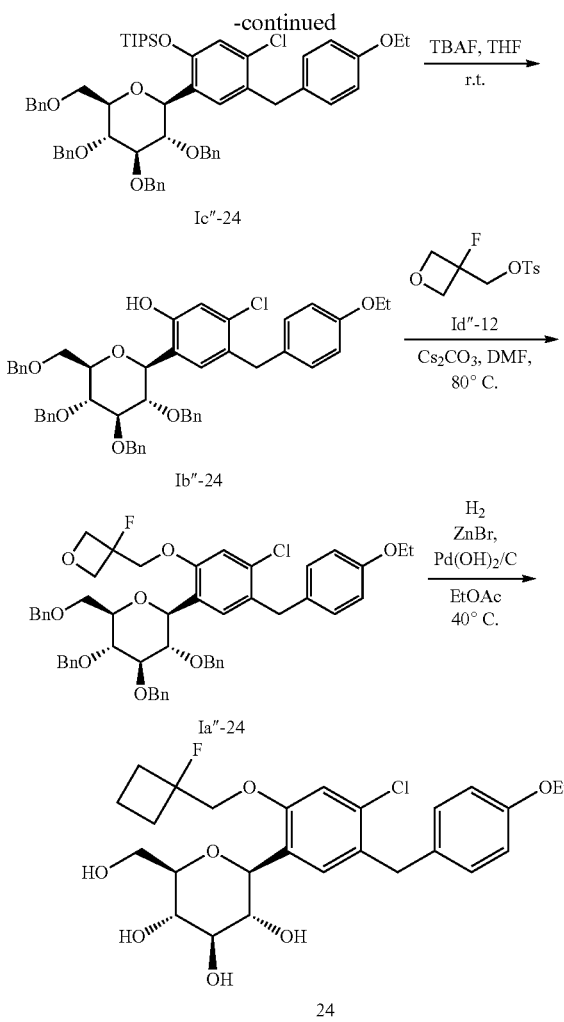

Preparation of compound Id″-24

At 0° C., to a solution of compound If″-24 (according to the synthesis procedure in reference: *Bioorg. Med. Chem.*, 2011, 19, 5468-5479.) (2.55 g, 7.47 mmol, 1.0 equiv) in THF (16 mL) was added NaH (60% in mineral oil, 0.45 g, 11.21 mmol, 1.5 equiv). After stirred at 0° C. for 30 minutes, the mixture was cooled to −78° C. A solution of n-BuLi in hexane (3.92 mL, 8.22 mol, 1.1 equiv) was added and the resulting mixture was stirred for further 30 minutes at −78° C. The mixture was treated with a solution of compound Ie″-24 (according to the synthesis procedure in reference: *J. Org. Chem.*, 1967, 32 (8), 2531-2534.) (4.02 g, 7.47 mmol, 1.0 equiv) in THF (12 mL) at −78° C., and was stirred for further 2 hours. Saturated aqueous NH$_4$Cl was added to quench the reaction. After the mixture was warmed to room temperature, ethyl acetate was added and the organic phase was washed with saturated aqueous NaHCO$_3$ and saturated brine successively. The organic phase was dried over anhydrous sodium sulphate, filtered, concentrated. The residue was purified by silica gel column chromatography (petroleum ether/ethyl acetate=15:1) to afford compound Id″-24 (2.4 g, 40%) as white solid.

Preparation of compound Ic″-24

At −78° C., a solution of triisopropyl silane (0.178 mL, 1.65 mmol, 1.5 equiv) in CH$_2$Cl$_2$ (1 mL) and a solution of TMSOTf (0.198 mL, 1.10 mmol, 1.0 equiv) in CH$_2$Cl$_2$ (1 mL) were added to a solution of compound Id″-24 (883 mg, 1.1 mmol, 1.0 equiv) in CH$_2$Cl$_2$ (40 mL) contained in a 100 mL round bottom flask, the mixture was stirred for one hour. Saturated aqueous NaHCO$_3$ was used to quench the reaction. After the mixture was warmed to room temperature, ethyl acetate was added and the organic phase was washed with saturated aqueous NaHCO$_3$ and saturated brine successively. The organic phase was dried over anhydrous sodium sulfate, filtered, concentrated. The residue was purified by silica gel column chromatography (petroleum ether/ethyl acetate=30:1) to afford compound Ic″-24 (595 mg, 58%).

$^1$H-NMR (500 MHz, CDCl$_3$) 7.22-7.07 (19H, m), 6.93 (2H, d, J=8.0 Hz), 6.87 (2H, brs), 6.76 (1H, s), 6.61 (2H, d, J=8.0 Hz), 4.81-4.74 (4H, m), 4.55-4.50 (2H, m), 4.40 (1H, d, J=12.5 Hz), 4.29 (1H, d, J=11.0 Hz), 3.94-3.90 (2H, m), 3.84-3.77 (3H, m), 3.67-3.61 (4H, m), 3.46 (2H, brs), 1.27 (3H, t, J=7.0 Hz), 1.22-1.16 (3H, m), 1.04-0.97 (18H, m).

Preparation of Compound Ib″-24

To a solution of compound Ic″-24 (595 mg, 0.63 mmol, 1.0 equiv) in THF (5 mL) was added a solution of tetrabutyl ammonium fluoride in THF (1.0 M, 0.95 mL, 0.95 mmol, 1.5 equiv) and the mixture was stirred for 30 minutes at room temperature, then diluted with ethyl acetate. The organic phase was washed with water and saturated brine successively, dried over anhydrous sodium sulfate, filtered and concentrated. The residue was purified by preparative TLC (petroleum ether/ethyl acetate=5:1) to afford compound Ib″-24 (434 mg, 88%).

$^1$H-NMR (500 MHz, CDCl$_3$) 7.68 (1H, s), 7.27-7.15 (15H, m), 7.09-7.08 (2H, m), 6.93-6.87 (5H, m), 6.82 (1H, s), 6.65 (2H, d, J=8.5 Hz), 4.85-4.75 (3H, m), 4.51-4.45 (2H, m), 4.40-4.37 (2H, m), 4.24 (1H, d, J=9.5 Hz), 3.94-3.77 (5H, m), 3.71-3.58 (5H, m), 3.47-3.46 (1H, m), 1.31 (3H, t, J=7.0 Hz).

Preparation of Compound Ia″-24

A mixture of compound Ib″-24 (100 mg, 0.127 mmol, 1.0 equiv), Id″-12 (99 mg, 0.381 mmol, 3.0 equiv), Cs$_2$CO$_3$ (83 mg, 0.254 mmol, 2.0 equiv) and DMF (5 mL) was heated to 80° C. overnight. After the removal of the solvent under vacuum, the residue was diluted with ethyl acetate and the organic phase was washed with water and saturated brine successively. The organic phase was dried over anhydrous sodium sulfate, filtered, concentrated. The residue was purified by preparative TLC (petroleum ether/ethyl acetate=5:1) to afford compound Ia″-24 (109 mg, 98%) as colorless oil.

$^1$H-NMR (500 MHz, CDCl$_3$) 7.24-7.19 (14H, m), 7.11-7.06 (5H, m), 6.98 (2H, d, J=8.5 Hz), 6.77 (1H, s), 6.74 (2H, d, J=7.0 Hz), 6.67 (2H, d, J=8.0 Hz), 4.85-4.77 (3H, m), 4.70-4.40 (9H, m), 4.01-3.85 (7H, m), 3.68-3.63 (5H, m), 3.49-3.48 (1H, brs), 1.30 (3H, t, J=7.0 Hz).

Preparation of Compound 24

Under hydrogen (charged for 3 times), to a flask were added compound Ia″-24 (103 mg, 0.118 mmol, 1.0 equiv), EtOAc (5 mL), ZnBr$_2$ (0.01 M in EtOAc, 0.118 mL, 0.00118 mmol, 0.01 equiv) and Pd(OH)$_2$/C (20% (dry), 21 mg, 0.029 mmol, 0.24 equiv), the mixture was stirred overnight at 40° C. After filtration through celite, the filter cake was washed with ethyl acetate and the filtrate was concentrated, the residue was purified by preparative HPLC to give compound 24 (32 mg, 53%) as white solid.

LC-MS (ESI): m/z=535 [M+Na]$^+$.

$^1$H-NMR (500 MHz, MeOD) 7.23 (1H, s), 7.00 (1H, s), 6.98 (2H, d, J=9.0 Hz), 6.69 (2H, d, J=8.5 Hz), 4.78-4.66 (4H, m), 4.42 (1H, d, J=10.0 Hz), 4.24 (2H, d, J=18.0 Hz), 3.90-3.84 (4H, m), 3.74 (1H, d, J=12.0 Hz), 3.55-3.46 (2H, m), 3.35-3.31 (1H, m), 3.28-3.23 (2H, m), 1.25 (3H, t, J=7.0 Hz).

Example 64

Synthetical Route of Compound 25 is Shown as Follows

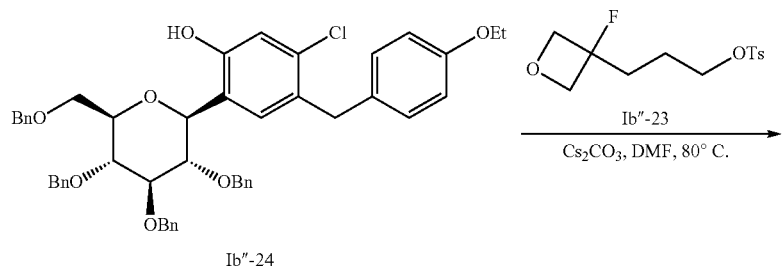

Ib"-24

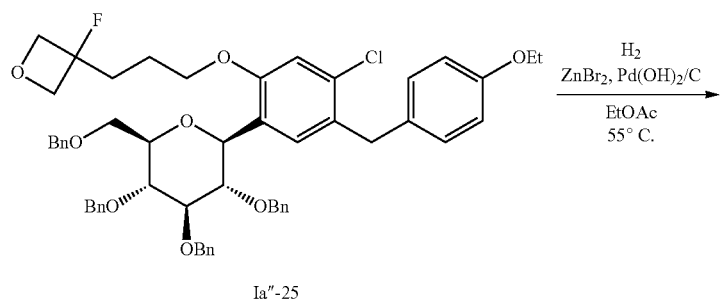

Ia"-25

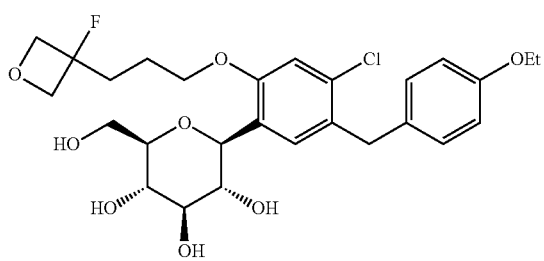

25

Preparation of Compound Ia"-25

A mixture of compound Ib"-24 (100 mg, 0.127 mmol, 1.0 equiv), Ib"-23 (110 mg, 0.381 mmol, 3.0 equiv), Cs$_2$CO$_3$ (83 mg, 0.254 mmol, 2.0 equiv) and DMF (5 mL) was stirred at 80° C. overnight. The solvent was evaporated under vacuum. The residue was diluted with ethyl acetate, washed in turn with water and saturated brine. The organic phase was dried over anhydrous sodium sulfate, filtered, concentrated. The residue was purified by preparative TLC (petroleum ether/ethyl acetate=5:1) to afford compound Ia"-25 (100 mg, 87%) as colorless oil.

$^1$H-NMR (500 MHz, CDCl$_3$) 7.25-7.19 (14H, m), 7.13-7.07 (5H, m), 6.97 (2H, d, J=9.0 Hz), 6.77-6.76 (3H, m), 6.65 (2H, d, J=8.5 Hz), 4.86-4.78 (3H, m), 4.75-4.61 (3H, m), 4.56-4.31 (7H, m), 4.16-4.12 (1H, m), 3.95-3.82 (6H, m), 3.70-3.64 (5H, m), 3.50-3.49 (1H, m), 1.75-1.68 (2H, m), 1.29 (3H, t, J=7.0 Hz).

Preparation of Compound 25

Under hydrogen (charged for 3 times), to a flask were added compound Ia"-25 (92 mg, 0.102 mmol, 1.0 equiv), EtOAc (5 mL), ZnBr$_2$ (0.01 M in EtOAc, 0.102 mL, 0.00102 mmol, 0.01 equiv) and Pd(OH)$_2$/C (20% (dry), 21 mg, 0.029 mmol, 0.28 equiv), the mixture was stirred at 55° C. overnight. After filtration through celite, the filter cake was washed with ethyl acetate, the filtrate was concentrated. The residue was purified by preparative HPLC to give compound 25 (18 mg, 33%) as white solid.

LC-MS (ESI): m/z=563 (M+Na)$^+$.

¹H-NMR (500 MHz, MeOD) 7.20 (1H, s), 6.97 (2H, d, J=8.5 Hz), 6.89 (1H, s), 6.68 (2H, d, J=8.5 Hz), 4.63 (2H, dd, J=8.0, 20 Hz), 4.54-4.46 (3H, m), 3.92-3.82 (6H, m), 3.74 (1H, d, J=11.5 Hz), 3.56-3.48 (2H, m), 3.38-3.34 (1H, m), 3.28-3.27 (2H, m), 2.11-2.02 (2H, m), 1.82-1.76 (2H, m), 1.25 (3H, t, J=7.0 Hz).

Example 65

Synthetical Route of Compound 65 is Shown as Follows

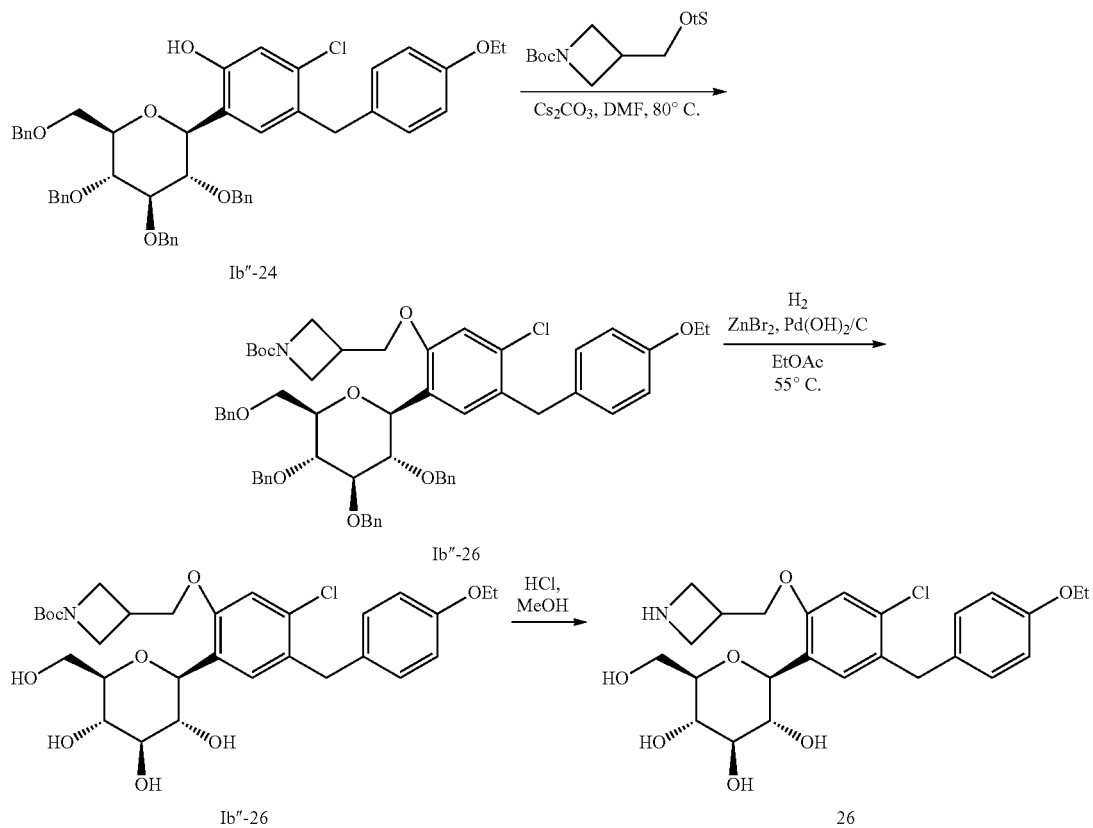

Preparation of Compound Ib"-26

A mixture of compound Ib"-24 (100 mg, 0.127 mmol, 1.0 equiv.), tert-butyl 3-(tosyloxymethyl)azitidine-1-carboxylate (130 mg, 0.381 mmol, 3.0 equiv.), Cs₂CO₃ (83 mg, 0.254 mmol, 2.0 equiv.) and DMF (5 mL) was stirred at 80° C. overnight. The solvent was evaporated under vacuum. The residue was diluted with ethyl acetate, washed in turn with water and saturated brine. The organic phase was dried over anhydrous sodium sulfate, filtered, concentrated. The residue was purified by preparative TLC (petroleum ether/ethyl acetate=3:1) to afford compound Ib"-26 (115 mg, 95%) as colorless oil.

¹H-NMR (500 MHz, CDCl₃) 7.31-7.25 (14H, m), 7.20-7.14 (5H, m), 7.04 (2H, d, J=9.0 Hz), 6.84-6.82 (3H, m), 6.73 (2H, d, J=8.5 Hz), 4.94-4.85 (3H, m), 4.63-4.47 (514, m), 4.02-3.91 (8H, m), 3.76-3.69 (7H, m), 3.56-3.54 (11-1, m), 2.84-2.78 (1H, m), 1.43 (911, s), 1.36 (3H, t, J=7.0 Hz).

Preparation of Compound Ia"-26

Under hydrogen (charged for 3 times), to a flask were added compound Ib"-26 (107 mg, 0.112 mmol, 1.0 equiv.), EtOAc (5 mL), ZnBr₂ (0.01 M in EtOAc, 0.112 mL, 0.00112 mmol, 0.01 equiv.) and Pd(OH)₂/C (20% (dry), 21 mg, 0.059 mmol, 0.53 equiv.), the mixture was stirred at 55° C. overnight. After filtration through celite, the filter cake was washed with ethyl acetate and the filtrate was concentrated. The residue was purified by preparative TLC (ethyl acetate/methanol=20:1) to give compound Ia"-26 (39 mg, 59%) as white solid.

LC-MS m/z=616 (M+Na)⁺.

Preparation of Compound 26

To a flask were added compound Ia"-26 (39 mg, 0.066 mmol, 1.0 equiv.), methanol (5 mL) and concentrated hydrochloric acid (0.055 mL, 0.66 mmol, 10 equiv.) respectively, the mixture was stirred at room temperature overnight. After starting materials disappeared (monitored by LC-MS), the mixture was neutralized by an addition of aqueous ammonia. The solvent was evaporated under vacuum, the residue was purified by preparative HPLC to afford compound 26 (17 mg, 52%).

LC-MS (ESI): m/z=494 (M+H)⁺.

¹H-NMR (500 MHz, MeOD) 7.23 (1H, s), 6.97 (2H, d, J=8.5 Hz), 6.94 (1H, s), 6.68 (2H, d, J=8.5 Hz), 4.47 (1H, d, J=9.5 Hz), 4.02-3.99 (2H, m), 3.90-3.82 (4H, m), 3.75-3.68 (3H, m), 3.62-3.53 (3H, m), 3.47-3.43 (1H, m), 3.38-3.35 (1H, m), 3.29-3.24 (2H, m), 3.12-3.04 (1H, m), 1.24 (3H, t, J=7.5 Hz).

Biological Effect Example 1

Uptake Assay of [$^{14}$C]-AMG in Flp-In CHO Cell Line Stably Expressing Human Sodium-Dependent Glucose Absorption Ion Channels I and II (Test of the Activity of SGLT2 and SGLT1)

A cDNA clone expressing human SGLT1/SGLT2 was bought from GenerScript. Having the sequence information, it was built into pcDNA5 carrier by using traditional molecular biology methods, and then the expression plasmids were transfected into Flp-in CHO cells by using Lipofetamin 200 liposomal transfection method. The transfected cells were screened for hygromycin resistance, and the single-cell clone was screened out through the process of gradient dilution. Having obtained the single-cell clone, the uptake assay of $^{14}$C-AMG in FLP-in CHO cells stably expressing SGLT1/SGLT2 was evaluated.

Cells were seeded at a density of $3\times10^4$ cells per well, uptake assay was carried out after adherent cells were cultured overnight. At least 12 hours later of culture, cells were washed once by 150 microliters per well of the absorption solution KRH-NMG (120 mM NMG, 4.7 mM KCl, 1.2 mM MgCl$_2$, 2.2 mM CaCl$_2$, 10 mM HEPES, pH 7.4 with HCl). To every well that was cleaned with buffer KRH-Na$^+$ and KRH-NMG, 45 μL buffer KRH-Na$^+$ which contained 2.5 μCi/ml [$^{14}$C]-AMG solution was added. A 5 μL solution of corresponding test compound which was dissolved in DMSO (concentration of DMSO: 1%), was added immediately to each well. The plate was incubated for one hour at 37° C. 150 μL ice cooled Wash Buffer (120 mM NaCl, 4.7 mM KCl, 1.2 mM MgCl$_2$, 2.2 mM CaCl$_2$, 10 mM HEPES, 0.5 mM phlorizin, pH 7.4 with Tris) was added immediately to each well in order to terminate the assay. Wash each well three times with Wash Buffer, and finally try to absorb all the liquid. During the process of washing, try the best to avoid exfoliation of cells. 20 μL Lysis Buffer (0.1 mM NaOH) was added to every well, the reaction plate was oscillated at a speed of 900 rpm for 5 minutes. 80 μL scintillation solution Microsint40 was added to every well, the reaction plate was then shaken for 5 minutes at a speed of 900 rpm. Finally, the plate was sent to the MicroBeta Trilux (PerkinElmer Co., Ltd.) to measure radioactivity. Analyze the data and calculate the IC$_{50}$ of each compound with XL-fit software.

Test results of the selected compounds are shown in table 1:

TABLE 1

| Compound Number | SGLT2 IC$_{50}$ nM (n = 1-4) | SGLT1 IC$_{50}$ nM (n = 1-4) | Selectivity (SGLT1/SGLT2) |
|---|---|---|---|
| DAPAGLIFLOZIN (BMS-512148) | 3.0 | 803 | 268 |
| EMPAGLIFLOZIN (BI-10773) | 3.1 | 3235 | 1044 |
| 1 | 5.6 | 2638 | 471 |
| 2 | 8.7 | 1638 | 188 |
| 3 | 11.4 | 2286 | 201 |
| 4 | 4.9 | 1447 | 295 |
| 5 | 8.3 | 792 | 95 |
| 6 | 9.6 | 2996 | 312 |
| 7 | 8.5 | 1055 | 124 |
| 8 | 1.7 | 930 | 547 |
| 9 | 7.5 | 1193 | 159 |
| 10 | 7.4 | 1302 | 176 |
| 11 | 6.8 | 1020 | 150 |
| 12 | 6.5 | 2080 | 320 |
| 13 | 28.7 | 2755 | 96 |
| 14 | 8.4 | 785 | 93 |
| 15 | 23.6 | 1464 | 62 |
| 16 | 8.1 | 2478 | 306 |
| 17 | 6.4 | 469 | 73 |
| 18 | 22 | 2451 | 111 |
| 19 | 97.2 | 1994 | 21 |
| 20 | 3.7 | 2553 | 690 |
| 21 | 3.5 | 3622 | 1035 |
| 22 | 1.7 | 4948 | 2911 |
| 23 | 1.1 | 1198 | 1089 |
| 24 | 12.0 | 17074 | 1424 |
| 25 | 12.3 | 18782 | 1559 |
| 26 | 69.4 | 1946 | 28 |

Wherein, the compound Dapagliflozin (BMS-512148, CAS No.: 461432-26-8) and compound EMPAGLIFLOZIN (BI-10773) are two known SGLT2 inhibitors. The structures are shown as follows:

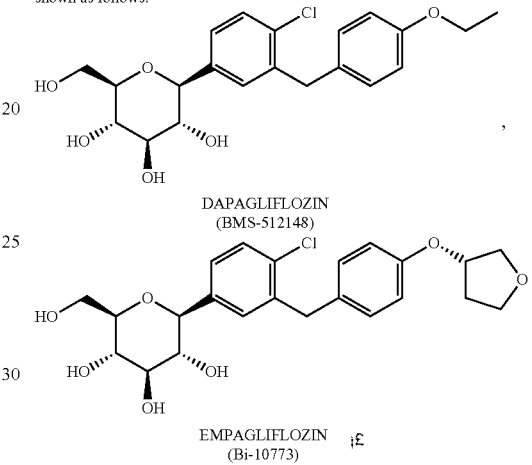

DAPAGLIFLOZIN (BMS-512148)

EMPAGLIFLOZIN (Bi-10773)

Biological Effect Example 2

Urinary Glucose Excretion Test

Adult C57 mice administered the test compound (10 mg/kg) were placed in metabolism cages for 24-hours urine collection, and measure the total volume of urine. When the urine samples had been collected, they were immediately frozen in a −20° C. refrigerator, followed by detecting the glucose concentration in urine. Finally, the total glucose in animal urine was calculated according to the total urine volume. It was then converted into urinary glucose excretion (mg) per 200 g of body weight within 24 hours according to the weight of mice. Results (average of 6 mice) are shown in Table 2:

TABLE 2

| Compound Number | Urine Glucose Excretion (mg/200 g BW/24 h) |
|---|---|
| EMPAGLIFLOZIN (BI-10773) | 1197 |
| 1 | 1333 |
| 5 | 1050 |
| 6 | 735 |
| 9 | 1079 |
| 10 | 740 |
| 12 | 1323 |
| 16 | 1441 |
| 17 | 180 |
| 20 | 751 |
| 23 | 1198 |

As shown in Table 1 and Table 2, the aryl glucoside compounds of the present invention, both in vitro and in vivo, are very good SGLT2 inhibitors, and this kind of compounds is a potential drug for treating or preventing diabetes.

The invention claimed is:

1. An aryl glucoside compound of formula I or formula I', or a pharmaceutically acceptable salt, optical isomer, or prodrug thereof:

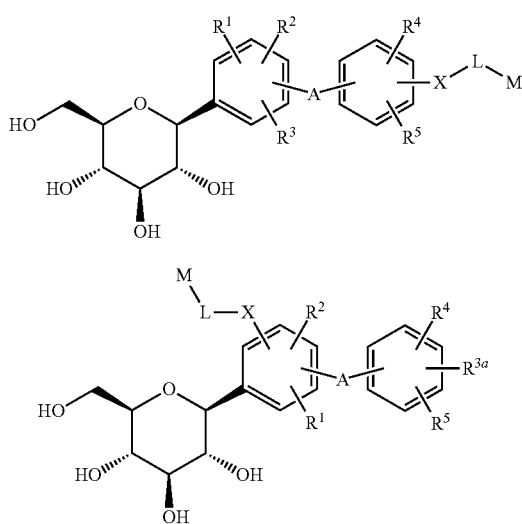

wherein,
- X is O, S, SO, $SO_2$, CO, $CONR^6$, NHCO, $NHSO_2$ or a single bond;
- L is $C_1$-$C_6$ alkylene, ($C_1$-$C_6$ alkylene)-($C_3$-$C_{10}$ cycloalkylene) or ($C_1$-$C_6$ alkylene)-($C_3$-$C_{10}$ cycloalkylene)-($C_1$-$C_6$ alkylene), and each methylene group in said cycloalkylene is optionally replaced by O, N, or S;
- M is 4-membered cycloheteroalkyl; with the proviso that when M is azetidinyl and L is linked with the nitrogen atom of M, then X-L is not $O(CH_2)_m CH(OR^{6f})CH_2$ where m is 1 to 3 and $R^{6f}$ is hydrogen, alkyl or alkylcarbonyl;
- $R^1$, $R^2$ and $R^3$ are independently selected from hydrogen, OH, $-OR^7$, alkyl, $-SR^{5i}$ or halogen, or two of $R^1$, $R^2$ and $R^3$ together with the carbons to which they are attached can form an annelated five, six or seven membered carbocycle or heterocycle which may contain 1 to 4 heteroatoms in the ring which are N, O, S, SO and/or $SO_2$;
- $R^{3a}$, $R^4$ and $R^5$ are independently selected from hydrogen, OH, $-OR^{5a}$, $-O$-Aryl, $-OCH_2$-Aryl, alkyl, cycloalkyl, halogen, $-CN$, $-CO_2R^{5b}$, $-CO_2H$, $COR^{6b}$, $-CH(OH)R^{6c}$, $-CH(OR^{5h})R^{6d}$, $-CONR^{6a}R^{6e}$, $-NHCOR^{5c}$, $-NHSO_2R^{5d}$, $-NHSO_2$-Aryl, Aryl, $-SR^{5e}$, $-SOR^{5f}$, $-SO_2R^{5g}$, $-SO_2$-Aryl, or a five, six or seven membered heterocycle which may contain 1 to 4 heteroatoms in the ring which are N, O, S; SO and/or $SO_2$; or $R^4$ and $R^5$ together with the carbons to which they are attached form an annelated five, six or seven membered carbocycle or heterocycle which may contain 1 to 4 heteroatoms in the ring which are N, O, S, SO and/or $SO_2$;
- $R^7$, $R^{5a}$, $R^{5b}$, $R^{5c}$, $R^{5d}$, $R^{5e}$, $R^{5f}$, $R^{5g}$, $R^{5h}$, and $R^{5i}$ are independently selected from alkyl;
- $R^6$, $R^{6a}$, $R^{6b}$, $R^{6c}$, $R^{6d}$ and $R^{6e}$ are independently selected from hydrogen, alkyl, aryl, alkylaryl or cycloalkyl, or $R^{6a}$ and $R^{6e}$ together with the nitrogen to which they are attached form an annelated five, six or seven membered heterocycle which may contain 1 to 4 heteroatoms in the ring which are N, O, S, SO and/or $SO_2$;
- A is O, S, 1,1-cyclopropylidene, CHF, $CF_2$ or $(CH_2)_n$ where n is 1 to 3.

2. The aryl glucoside compound or pharmaceutically acceptable salt, optical isomer, or prodrug thereof as defined in claim 1, wherein where $R^1$, $R^2$ and $R^3$ are independently halogen, said halogen is Cl;
and/or where L is $C_1$-$C_6$ alkylene, said $C_1$-$C_6$ alkylene is methylene, ethylene or n-propylene.

3. The aryl glucoside compound or pharmaceutically acceptable salt, optical isomer, or prodrug thereof as defined in claim 1,
wherein the substitution position of group A in said formula I is shown as follows:

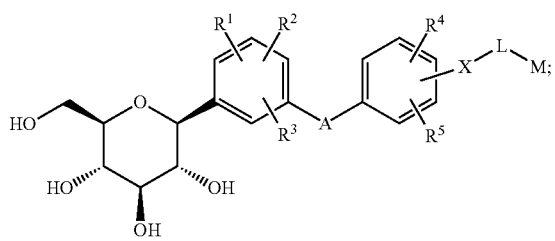

the substitution position of group A in said formula I' is shown as follows:

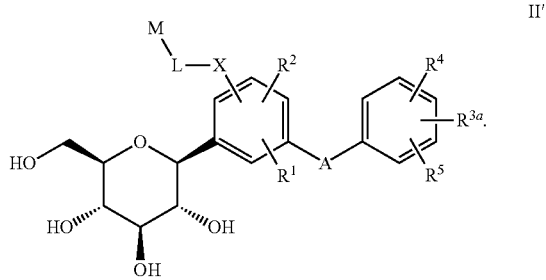

4. The aryl glucoside compound or pharmaceutically acceptable salt, optical isomer, or prodrug thereof as defined in claim 3, wherein the substitution position of group X in said formula I, I', II or II' is para to group A.

5. The aryl glucoside compound or pharmaceutically acceptable salt, optical isomer, or prodrug thereof as defined in claim 1, wherein said compound I has following structure IIA:

IIA

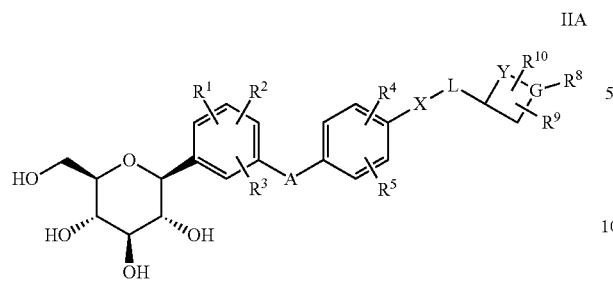

wherein Y is carbon or oxygen, G is carbon, O, N, S, or SO, and Y and G can not be carbon at the same time wherein when G is O, S or SO, $R^8$ is none; and wherein when G is N, $R^8$ is H, $C_1$-$C_3$ alkyl, carbonyl linked with $C_1$-$C_3$ alkyl, carbonyl linked with $C_1$-$C_6$ alkyloxy, $C_6$-$C_{10}$ aryl substituted by halogen, 4-membered cycloheteroalkyl having oxygen as the only one heteroatom, or $SO_2$ linked with $C_1$-$C_3$ alkyl;

$R^9$ and $R^{10}$ are independently selected from hydrogen, $C_1$-$C_6$ alkyl, halogen, OH, cycloalkyl, $C_1$-$C_6$ alkoxy, $C_1$-$C_6$ alkylcarbonyloxy, amino, $C_1$-$C_3$ alkyl substituted by halogen, $C_1$-$C_6$ alkylamino, or $C_1$-$C_6$ alkylcabonylamino; and $R^1$, $R^2$, $R^3$, $R^4$, $R^5$, A, X and L are as defined in formula said compound I' has following structure II'A:

II'A

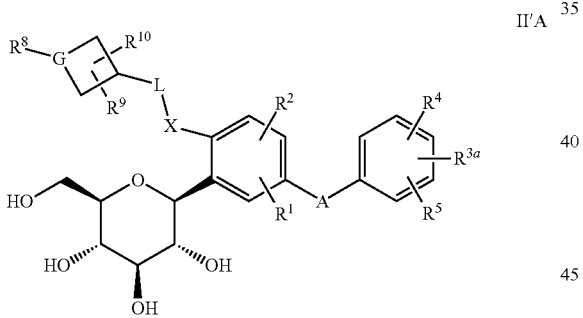

wherein G is carbon, O, N, S, or SO, wherein when G is O, S or SO, $R^8$ is none; and wherein when is N, $R^8$ is H, $C_1$-$C_3$ alkyl, carbonyl linked with $C_1$-$C_3$ alkyl, carbonyl linked with $C_1$-$C_6$ alkoxy or $SO_2$ linked with $C_1$-$C_3$ alkyl;

$R^9$ and $R^{10}$ are independently selected from hydrogen, $C_1$-$C_6$ alkyl, halogen, OH, cycloalkyl, $C_1$-$C_6$ alkoxy, $C_1$-$C_6$ alkylcarbonyloxy, amino, $C_1$-$C_3$ alkyl substituted by halogen, $C_1$-$C_6$ alkylamino, or $C_1$-$C_6$ alkylcabonylamino; and $R^1$, $R^2$, $R^{3a}$, $R^4$, $R^5$, A, X and L are as defined in formula I'.

6. The aryl glucoside compound or pharmaceutically acceptable salt, optical isomer, or prodrug thereof as defined in claim 5, wherein said compound IIA has following structure IIAa or IIAb:

IIAa

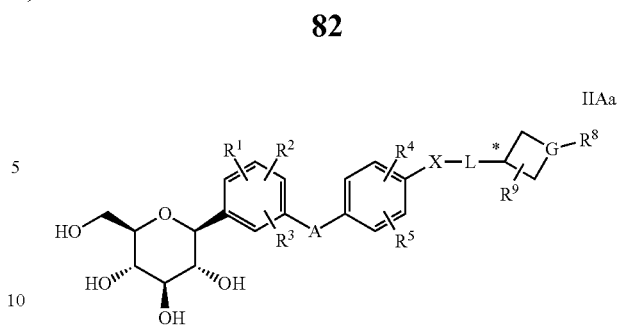

wherein G is O, N, S, or SO; * denotes racemic, or the absolute configuration of R or S; and $R^1$, $R^2$, $R^3$, $R^4$, $R^5$, $R^8$, $R^9$, A, X and L are as defined in formula IIA;

IIAb

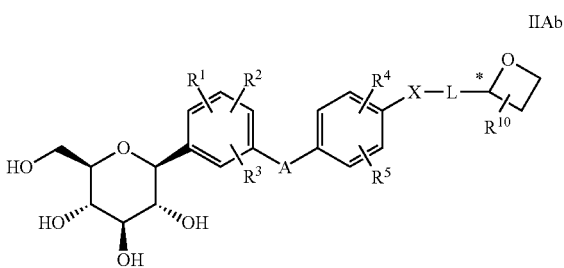

wherein * denotes racemic, or the absolute configuration of R or S; and $R^1$, $R^2$, $R^3$, $R^4$, $R^5$, $R^{10}$, A, X and L are as defined in formula IIA.

7. The aryl glucoside compound or pharmaceutically acceptable salt, optical isomer, or prodrug thereof as defined in claim 1, wherein said compound I is selected from any one of the following compounds:

1

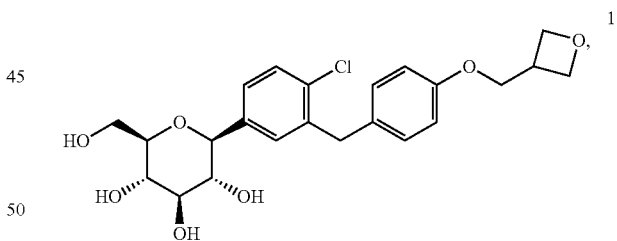

2

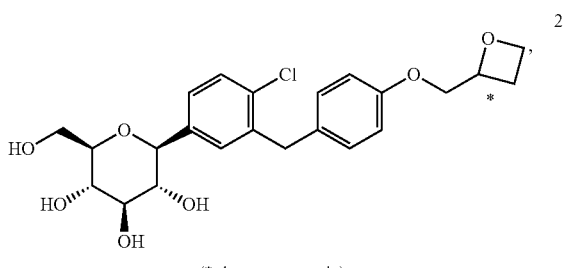

(* denotes racemic)

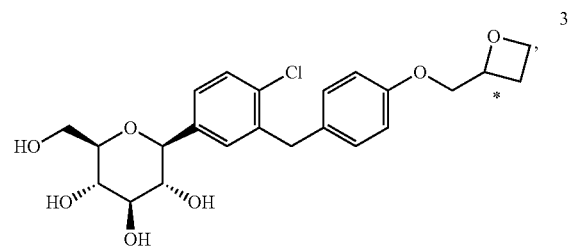
3
(* denotes optical isomerism)
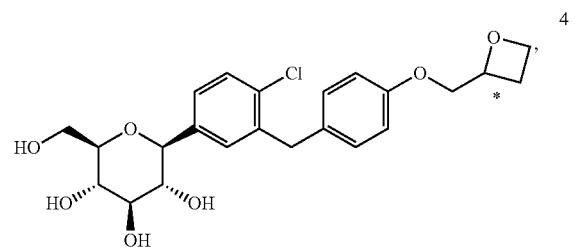
4
(* denotes optical isomerism)
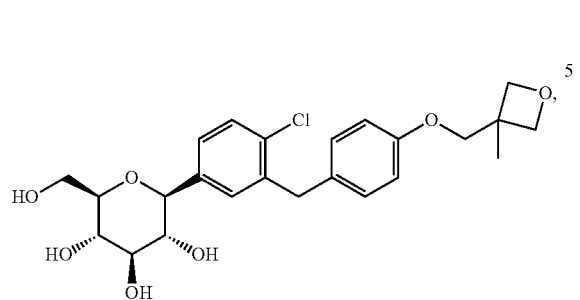
5
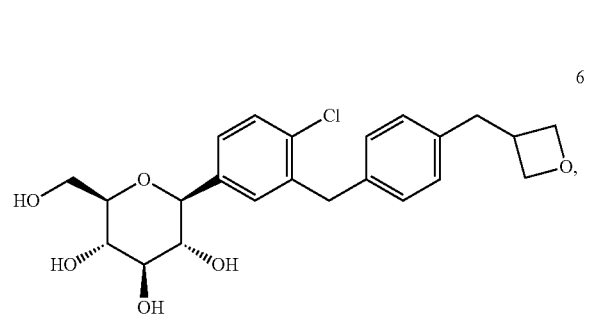
6
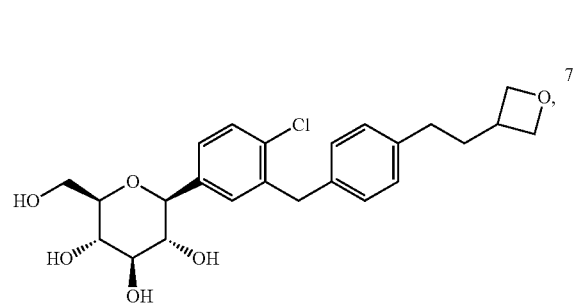
7
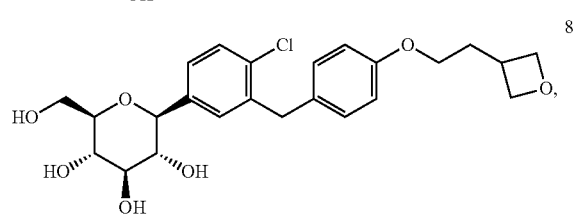
8
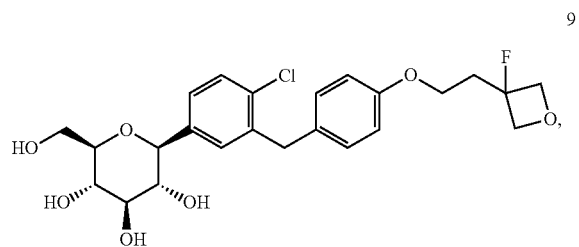
9
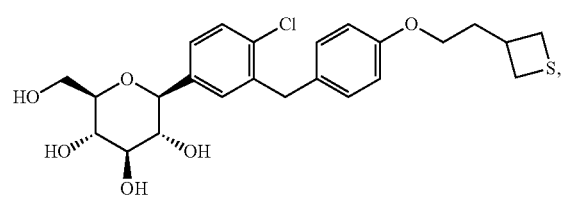
10
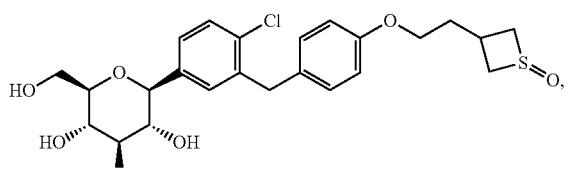
11
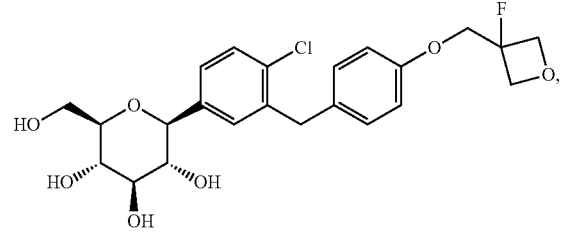
12
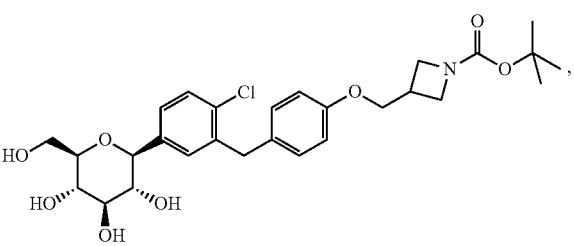
13
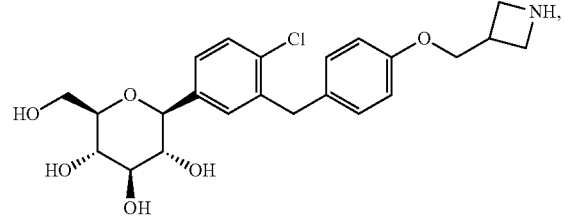
14

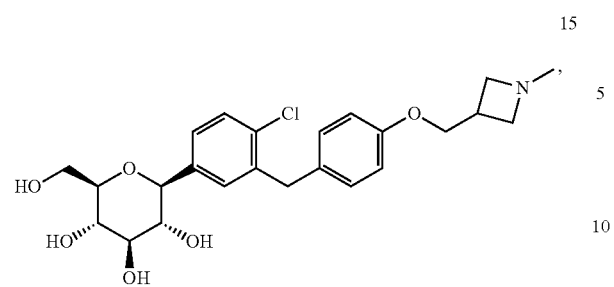
15
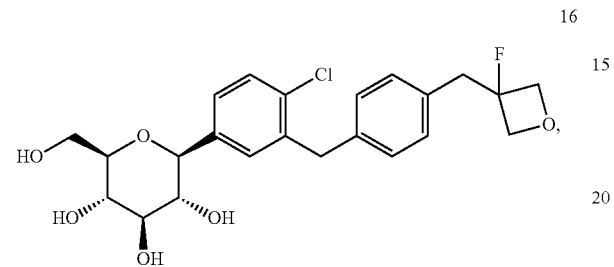
16
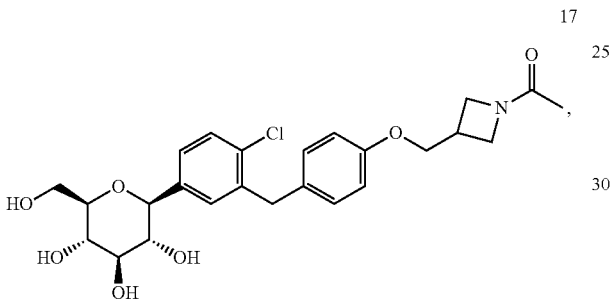
17
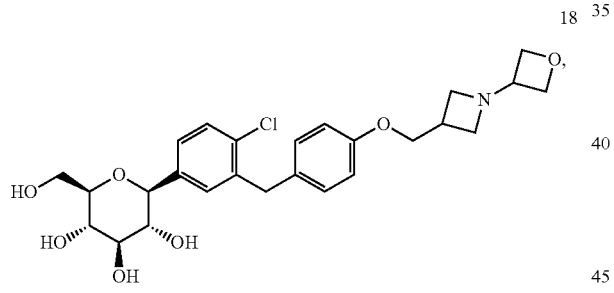
18
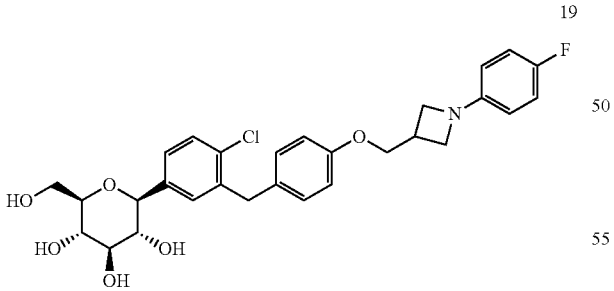
19
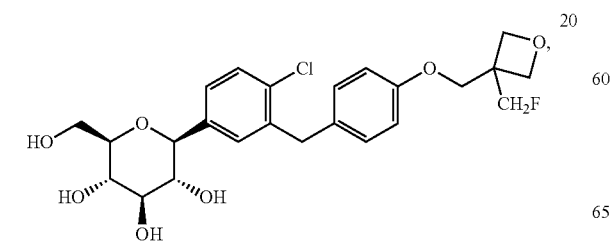
20
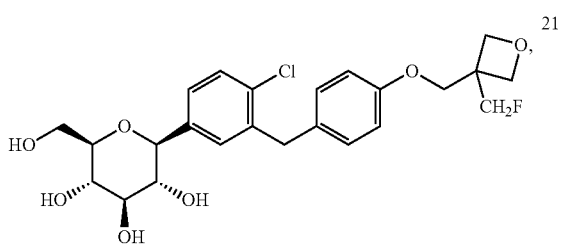
21
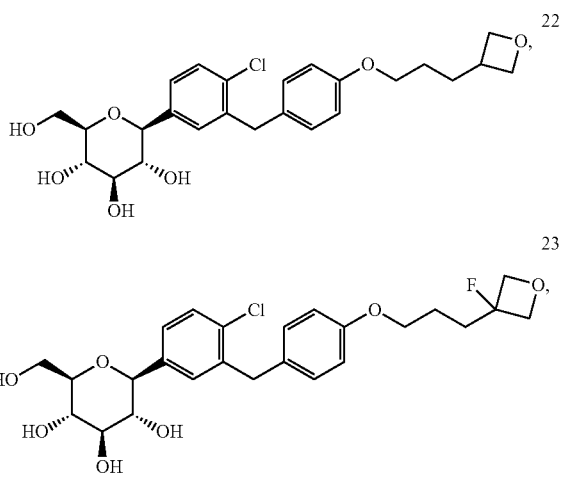
22
23
wherein, the absolute configurations of the carbon atoms labelled with * in compounds 3 and 4 have enantiomeric relationship, and compound 3 and compound 4 are both optical isomers of compound 2;
wherein said compound I' is selected from any one of the following compounds:
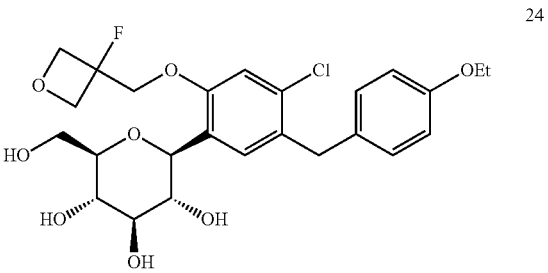
24
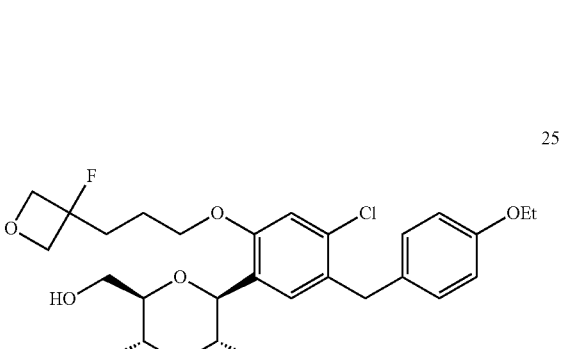
25

-continued

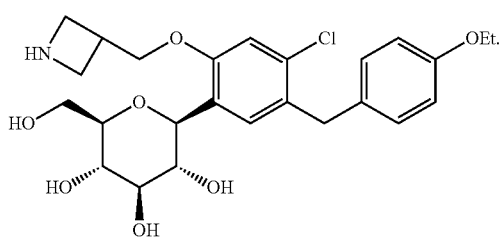
26

8. A process for preparing aryl glucosides according to claim 1, wherein said process is any one of the following three methods:

Method 1: compound Ia reacting with compound R'OTs or R'OMs to obtain compound I via a nucleophilic substitution reaction;

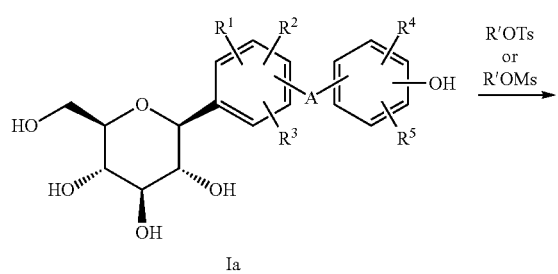

wherein R'OTs is TsO-L-M, R'OMs is MsO-L-M, and wherein $R^1$, $R^2$, $R^3$, $R^4$, $R^5$, A, L and M are as defined in formula I;

Method 2: deprotecting the acetyl protecting groups of hydroxyl groups of compound Ia' to obtain compound I;

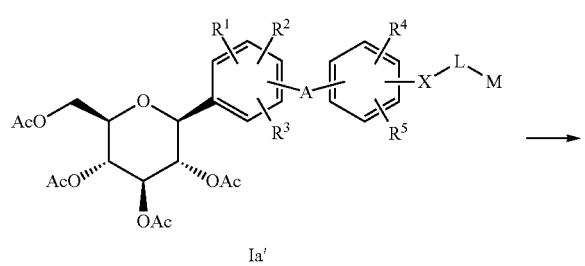

-continued

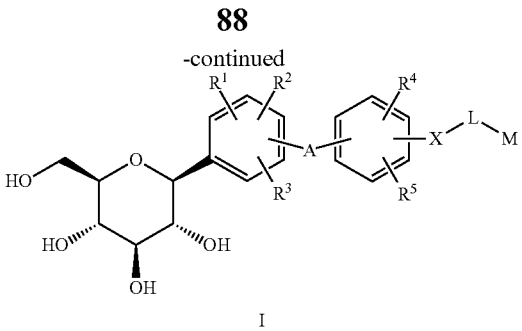

wherein $R^1$, $R^2$, $R^3$, $R^4$, $R^5$, A, X, L and M are as defined in formula I;

Method 3: compound I' a reacting with compound R'OTs or R'OMs via a nucleophilic substitution reaction followed by deprotecting the benzyl protecting groups of hydroxyl groups to obtain compound I';

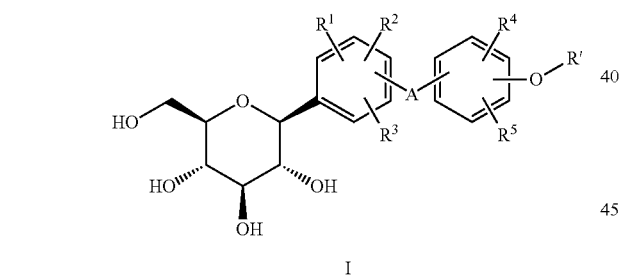

wherein, R'—OTs is

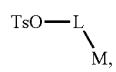

R'—OMs is

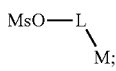

and wherein $R^1$, $R^2$, $R^{3a}$, $R^4$, $R^5$, A, L and M are as defined in formula I'.

9. The process for preparing aryl glucosides according to claim 8, wherein said compound Ia' is prepared by any one of the following methods:

(1) performing ether-forming reaction between compound Ib' and R'OH;

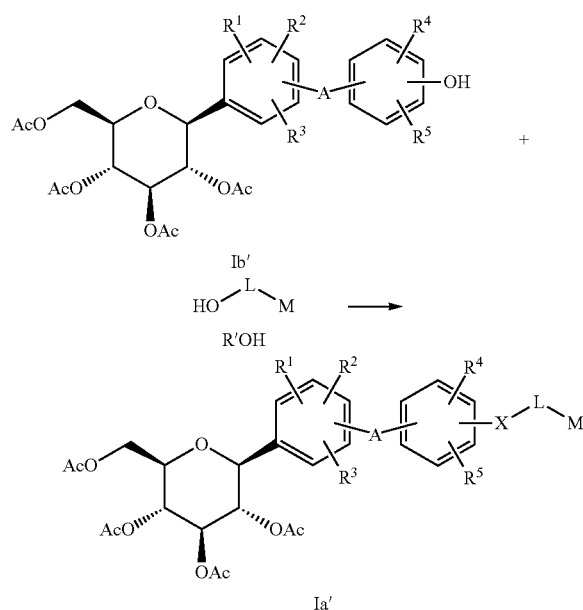

wherein X is O and $R^1$, $R^2$, $R^3$, $R^4$, $R^5$, A, L and M are as defined in formula Ia'; or (2) performing coupling reaction between compound Ibb and Ib''

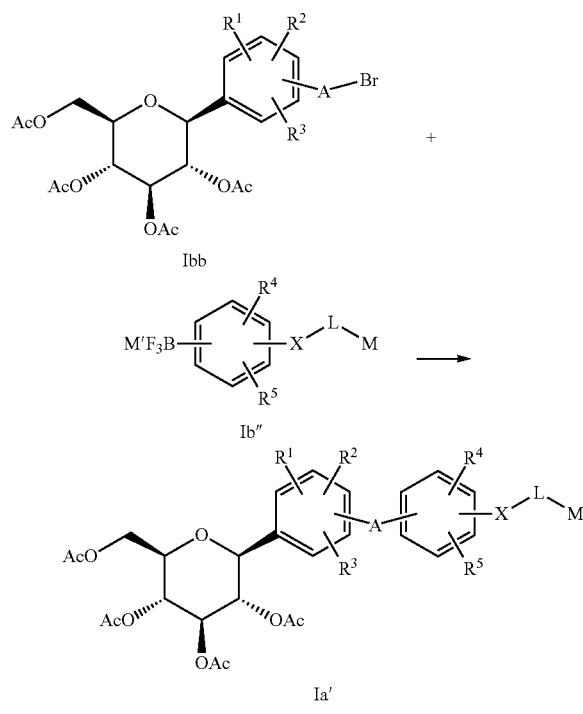

wherein M' is alkali metal and $R^1$, $R^2$, $R^3$, $R^4$, $R^5$, A, X, L and M are as defined in formula Ia';

said compound I'a is prepared by following method: the reaction to remove the silyl ether protecting group of compound I'b is carried out;

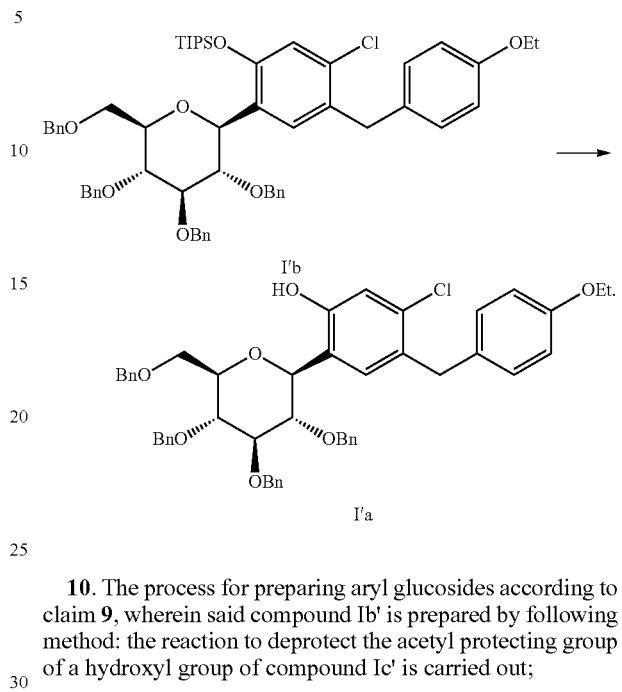

10. The process for preparing aryl glucosides according to claim 9, wherein said compound Ib' is prepared by following method: the reaction to deprotect the acetyl protecting group of a hydroxyl group of compound Ic' is carried out;

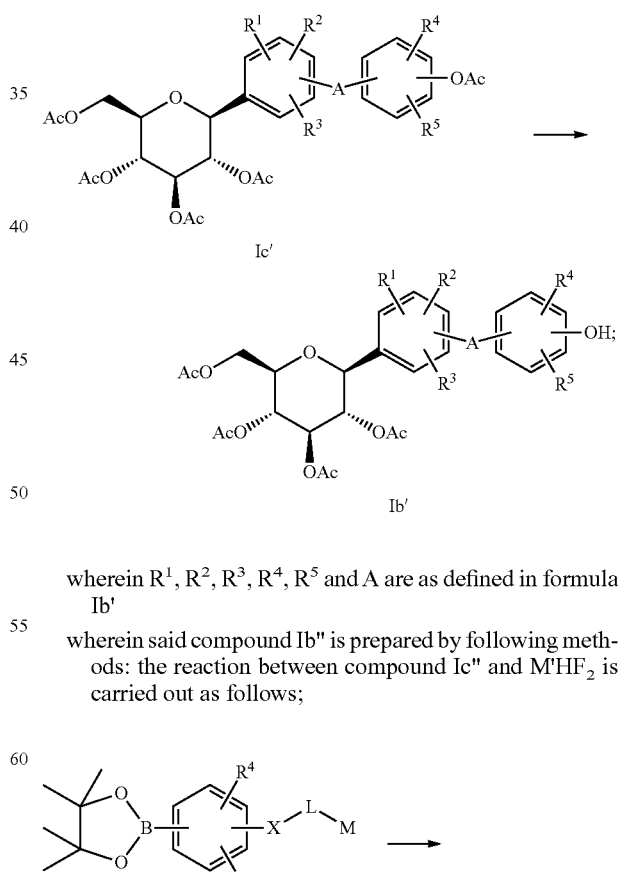

wherein $R^1$, $R^2$, $R^3$, $R^4$, $R^5$ and A are as defined in formula Ib' wherein said compound Ib'' is prepared by following methods: the reaction between compound Ic'' and M'HF$_2$ is carried out as follows;

-continued

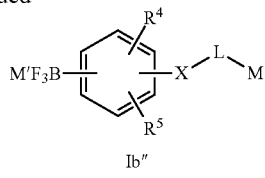

wherein R⁴, R⁵, X, L, M and M' are as defined in formula Ib'' wherein said compound I'b is prepared by following methods: the reduction reaction between compound I'c and silane is carried out;

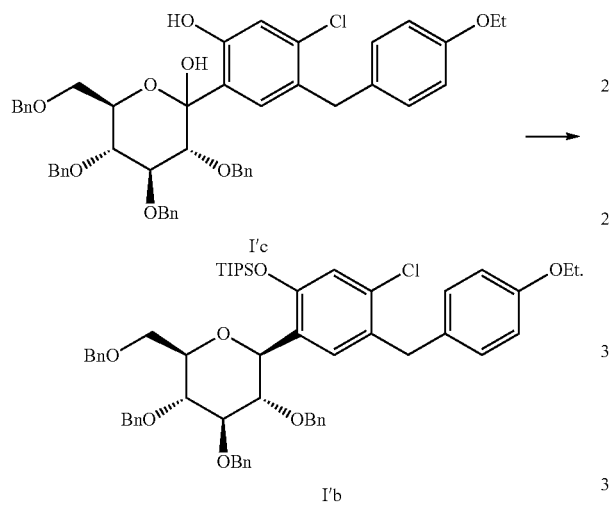

11. The process for preparing aryl glucosides according to claim 10, wherein said compound Ic' is prepared by following method: a hydroxyl acetylation reaction is carried out with compound Id';

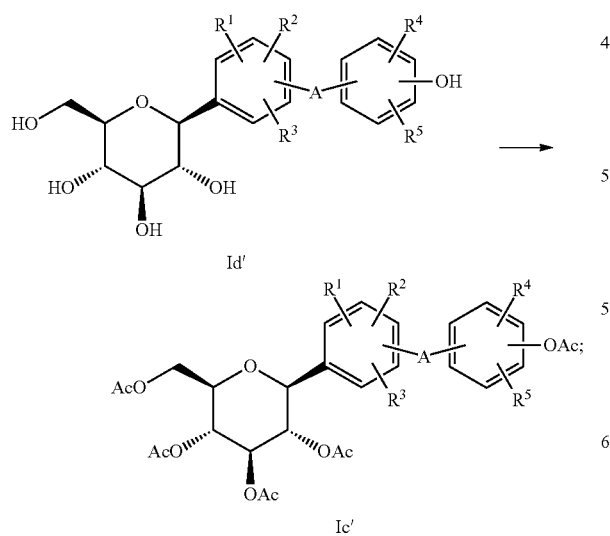

wherein $R^1$, $R^2$, $R^3$, $R^4$, $R^5$ and A are as defined in formula Ic';

wherein said compound Ic'' is prepared by following method: the reaction between compound Id'' and bis(pinacolato)diboron is carried out;

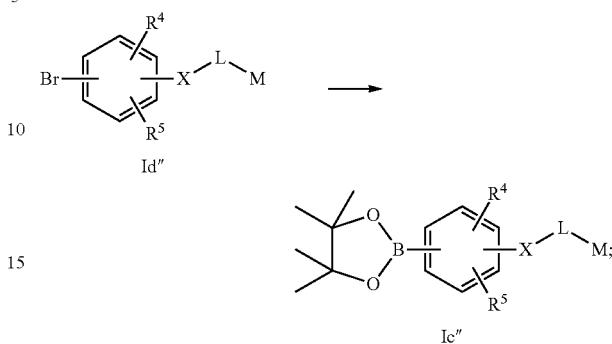

wherein $R^4$, $R^5$, X, L and M are as defined in formula Ic'';

said compound I'c is prepared by following method: the condensation reaction between compound I'd and compound I'e is carried out;

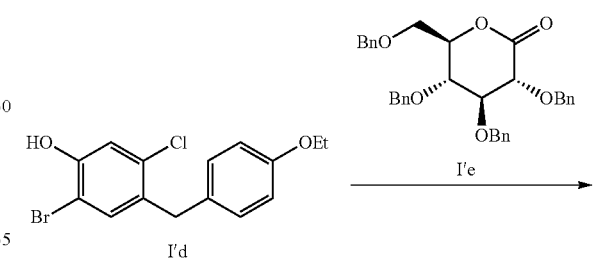

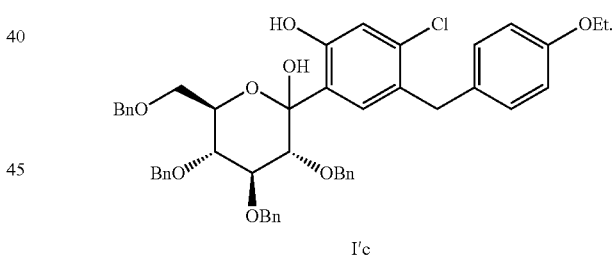

12. The process for preparing aryl glucosides according to claim 11, wherein said compound Id' is prepared by following method: a reaction to remove the methoxy group is carried out with compound Ie';

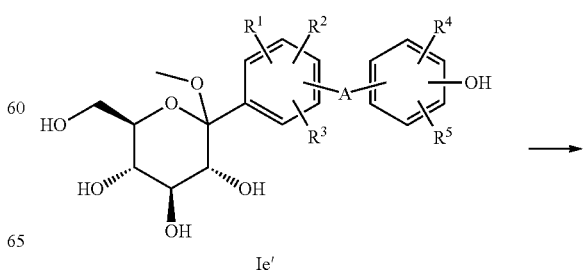

-continued

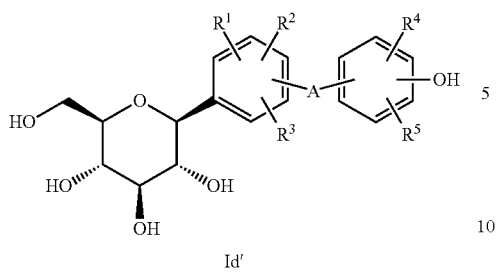
Id' wherein $R^1$, $R^2$, $R^3$, $R^4$, $R^5$ and A are as defined in formula Id'.

13. The process for preparing aryl glucosides according to claim 12, wherein said compound Ie' is prepared by following method: a condensation reaction between compound If' and f' followed by a methylation reaction between the resulting material and the methanol solution of methanesulphonic acid, a reaction to deprotect the trimethylsilyl groups of the hydroxyl groups and a reaction to remove the methoxymethyl group of the phenolic hydroxyl group is carried out;

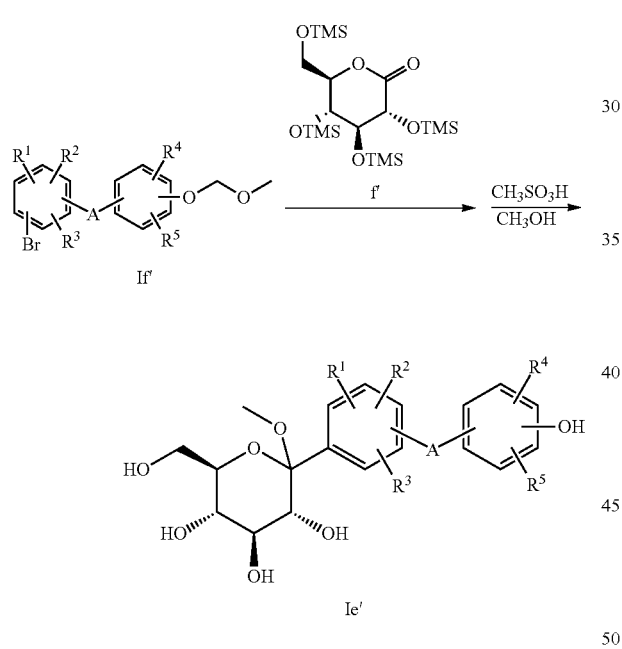

wherein $R^1$, $R^2$, $R^3$, $R^4$, $R^5$ and A are as defined in formula Ie'.

14. The process for preparing aryl glucosides according to claim 13, wherein said compound If' is prepared by following method: a nucleophilic substitution reaction between compound Ig' and chloromethyl ether is carried out;

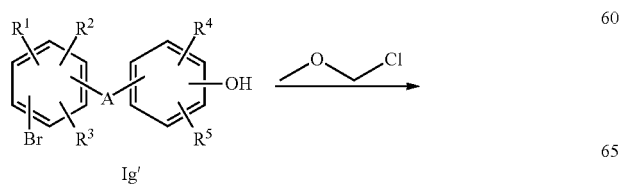

-continued

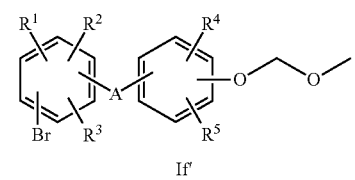
If' wherein $R^1$, $R^2$, $R^3$, $R^4$, $R^5$ and A are as defined in formula If'.

15. The intermediates shown as any one of the following structures used for preparing aryl glucosides according to claim 1;

Id''-1

Ic''-1

Ib''-1

Id''-6

Ic''-6

Ib''-6

Id''-7

-continued

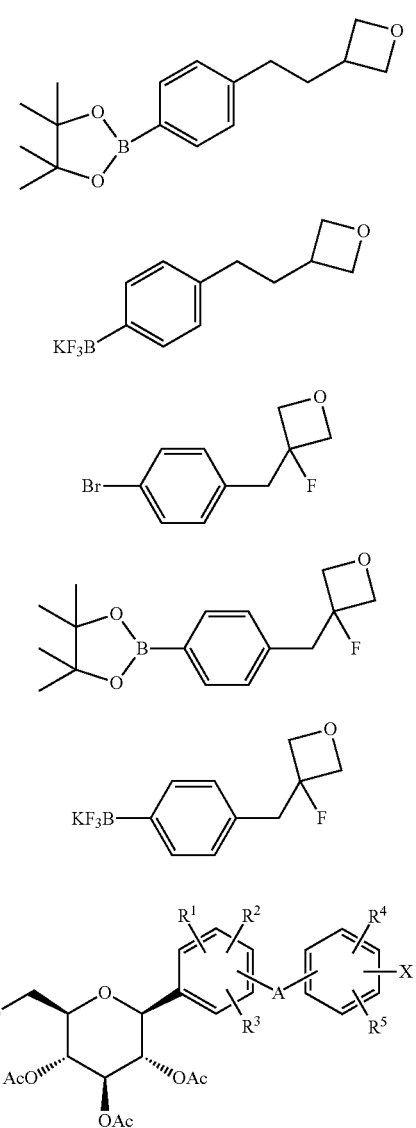

wherein $R^1$, $R^2$, $R^3$, $R^4$, $R^5$, A, X, L and M are as defined in claim 1.

16. A sodium-dependent glucose cotransporter inhibitor comprising the aryl glucoside compound, pharmaceutically acceptable salt, optical isomer, or prodrug thereof according to claim 1.

17. A method for treating or delaying the development of, or attack of, a disease, and/or a method for increasing the level of high density lipoprotein, wherein the method comprises administering the aryl glucoside compound, pharmaceutically acceptable salt, optical isomer, or prodrug thereof according to claim 1 to a subject in need thereof, wherein the disease is selected from the group consisting of diabetes, diabetic retinopathy, diabetic neuropathy, diabetic nephropathy, delayed wound healing, insulin resistance, hyperglycemia, hyperinsulinemia, an increase of the levels of fatty acid or glycerol in blood, hyperlipidemia, obesity, hypertriglyceridemia, syndrome X, artery atherosclerosis, and hypertension.

18. A method according to claim 17, wherein said disease is type II diabetes mellitus.

19. A pharmaceutical composition comprising an effective dose of the aryl glucoside compound or pharmaceutically acceptable salt, optical isomer, or prodrug thereof according to claim 1, and a pharmaceutically acceptable carrier or excipient.

20. The pharmaceutical composition according to claim 19, wherein the composition further comprises one or more following agents: an antidiabetic agent, an agent for treating the complications of diabetes, an anti-obesity agent, an antihypertensive agent, an antiplatelet agent, an antiatherosclerosis agent and a lipid-lowering agent which are non sodium-dependent glucose cotransporter inhibitors.

21. The pharmaceutical composition according to claim 20, wherein said antidiabetic agent is one or more selected from the following: metformin, glyburide, glimepiride, glipizide, gliclazide, glipyride, pioglitazone, troglitazone, rosiglitazone, acarbose, miglitol, chlorpropamide, nateglinide, repaglinide, insulin, AC2993, AJ7677, AR-H039242, GI-262570, isaglitazone, JTT-501, KAD1129, KRP297, LY315902, NN-2344, NVP-DPP-728A, R-119702 and YM-440.

\* \* \* \* \*